United States Patent [19]
Wang

[11] Patent Number: 5,912,176
[45] Date of Patent: Jun. 15, 1999

[54] ANTIBODIES AGAINST A HOST CELL ANTIGEN COMPLEX FOR PRE AND POST EXPOSURE PROTECTION FROM INFECTION BY HIV

[75] Inventor: Chang Yi Wang, Cold Spring Harbor, N.Y.

[73] Assignee: United Biomedical, Inc., Hauppuage, N.Y.

[21] Appl. No.: 08/867,149

[22] Filed: Jun. 2, 1997

Related U.S. Application Data

[63] Continuation-in-part of application No. 08/808,374, Feb. 28, 1997, which is a continuation-in-part of application No. 08/657,149, Jun. 3, 1996, abandoned.

[51] Int. Cl.[6] .................. C12N 15/08; A61K 39/395; C07K 16/28
[52] U.S. Cl. .................. 435/452; 424/133.1; 424/154.1; 424/173.1; 435/69.6; 435/70.21; 435/343.2; 530/387.3; 530/388.75; 530/389.6
[58] Field of Search .................. 424/133.1, 139.1, 424/148.1, 154.1, 160.1, 173.1; 435/69.6, 70.21, 172.2, 172.3, 328, 331, 339.1, 343.2, 320.1, 451, 452; 530/387.3, 387.9, 388.35, 388.75, 389.4, 389.6

[56] References Cited

U.S. PATENT DOCUMENTS

| | | | |
|---|---|---|---|
| 4,381,295 | 4/1983 | Kung et al. | 424/85 |
| 4,816,397 | 3/1989 | Boss et al. | 435/68 |
| 5,171,838 | 12/1992 | Chiba | 530/326 |

FOREIGN PATENT DOCUMENTS

| | | |
|---|---|---|
| 0 018 794 B1 | 7/1985 | European Pat. Off. . |
| WO 90/02199 | 3/1990 | WIPO . |
| WO 92/09305 | 6/1992 | WIPO . |
| WO 93/12227 | 6/1993 | WIPO . |

OTHER PUBLICATIONS

Arthos et al., (1989) "Identification of the Residues in Human CD4 Critical for the Binding of HIV" *Cells* 57:469–481.
Arthur et al. (1991) "Cellular Proteins Bound to Immunodeficiency Viruses: Implications for Pathogenesis and Vaccines" *Science* 258:1935–1938.
Attanasio et al. (1993) "Monoclonal Anti–CD4 as Immunoprophylactic Agents for Human Immunodeficiency Virus Infection" *J. Infect. Dis.* 168:515–516.
Baltimore (1995) "The Enigma of HIV Infection" *Cell* 82:175–176.
Belshe et al. (1994) "Neutralizing Antibodies to HIV–1 in Seronegative Volunteers Immunized with Recombinant gp120 from the MN Strain of HIV–1" *JAMA* 272:475–480.
Brady et al. (1993) "Crystal Structure of Domains 3 and 4 of Rat CD4: Relation to the $NH_2$–Terminal Domains" *Science* 260:979–983.
Burkly et al. (1992) "Inhibition of HIV Infection by a Novel CD4 Domain 2–Specific Monoclonal Antibody" *J. Immunol.* 149:1779–1787.

Burton et al. (1994) "Effective Neutralization of Primary Isolates of HIV–1 by a Recombinant Human Monoclonal Antibody" *Science* 266:1024–1027.
Camerini et al. (1990) "A CD4 Domain Important for HIV–Mediated Syncytium Formation Lies outside the Virus Binding Site" *Cell* 60:747–754.
Clayton et al. (1988) "Substitution of Murine for Human CD4 Residues Identifies Amino Acids Critical for HIV–gp120 Binding" *Nature* 335:363–366.
Cocchi et al. (1995) "Identification of RANTES, MIP–1α, and MIP–1β as the Major HIV–Suppressive Factors Produced by $CD8^+T$ Cells" *Science* 270:1811–1815.
Corbeau et al. (1993) "Ig CDR3–Like Region of the CD4 Molecule is Involved in HIV–Induced Syncytia Formation but not in Viral Entry" *J. Immunol.* 150:290–301.
Daar et al. (1990) "High Concentrations of Recombinant Soluble CD4 are Required to Neutralize Primary Human Immunodeficiency Virus Type 1 Isolates" *Proc. Nat'l Accad. Sci. U.S.A.* 87:6574–6578.
Dalgleish et al. (1984) "The CD4 (T4) Antigen is an Essential Component of the Receptor for the AIDS Retrovirus" *Nature* 312:763–766.
Davis et al. (1992) "Antibody and HIV–1 gp120 Recognition of CD4 Undermines the Concept of Mimicry between Antibodies and Receptors" *Nature* 358:76–79.
Desrosiers et al. (1989) "Vaccine Protection Against Simian Immunodeficiency Virus Infection" *Proc. Nat'l. Accad. Sci. U.S.A.* 86:6353–6357.
Dimitrov (1996) "Fusin—a place for HIV–1 and T4 Cells to Meet" *Nature Medicine* 2:640–641.
Emini et al. (1992) "Prevention of HIV–1 Infection in Chimpanzees by gp120 V3 Domain–Specific Monoclonal Antibody" 355:728–730.

(List continued on next page.)

*Primary Examiner*—Robert D. Budens
*Attorney, Agent, or Firm*—Morgan & Finnegan LLP

[57] ABSTRACT

This invention is directed to monoclonal antibodies produced by using CD4-expressing T lymphocytes, such as peripheral blood mononuclear T cells, thymocytes, splenocytes and leukemia or lymphoma derived T cell line cells such as HPB-ALL or SUP-T as the immunogen in accordance with the protocols and screening procedures described. The monoclonal antibodies of the present invention are characterized by their ability to neutralize in vitro and in vivo primary isolates of Human Immunodeficiency Virus (HIV) and related immunodeficiency viruses. The antibodies are directed against a host cell antigen complex comprising CD4 protein in association with domains from chemokine receptors and have broad neutralizing activities against primary isolates from all clades of HIV type 1 (HIV-1) and primary isolates of HIV type 2 (HIV-2) and Simian Immunodeficiency Virus (SIV). The present invention is also directed to a method of selecting and producing such antibodies, hybridomas which secrete such antibodies, pharmaceutical compositions comprising such antibodies and methods for pre- and post-exposure prevention of immunodeficiency virus infection in primates, including humans, by such antibodies whose primary targets are CD4 expressing lymphocytes.

94 Claims, 5 Drawing Sheets

OTHER PUBLICATIONS

Emini et al. (1990) "Antibody–Mediated In Vitro Neutralization of Human Immunodeficiency Virus Type 1 Abolishes Infectivity for Chimpanzees" *J. Virol.* 64:3674–3678.

Feng et al. (1996) "HIV–1 Entry Cofactor: Functional cDNA Cloning of a Seven–Transmembrane, G Protein–Coupled Receptor" *Science* 272:873–877.

Gardner et al. (1995) "Passive Immunization of Rhesus Macaques against SIV Infection and Disease" *AIDS Research and Human Retroviruses* 11:843–854.

Gauduin et al. (1995) "Pre–and Postexposure Protection against Human Immunodeficiency Virus Type 1 Infection Mediated by a Monoclonal Antibody" *J. of Infectious Diseases* 171:1203–1209.

Hanson et al. (1990) "Application of a Rapid Microplaque Assay for Determination of Human Immunodeficiency Virus Neutralizing Antibody Titers" *J. of Clinical Microbiology* 28(9):2030–2034.

Hanson (1994) "Measuring Vaccine–Induced HIV Neutralization: Report of a Workshop" *AIDS Research and Human Retroviruses* 10:645–648.

Hasunuma et al. (1992) "Regions of the CD4 Molecule not involved in Virus Binding or Syncytia Formation are Required for HIV–1 Infection of Lymphocytes" *J. of Immunology* 148:1841–1846.

Ho et al. (1989) "Quantitation of Human Immunodeficiency Virus Type 1 in the Blood of Infected Persons" *The New England Journal of Medicine* 321:1621–1625.

Ho et al. (1991) "Conformational Epitope on gp120 Important in CD4 Binding and Human Immunodeficiency Virus Type 1 Neutralization Identified by a Human Monoclonal Antibody" *J. of Virology* 65:489–493.

Jameson et al. (1988) "Location and Chemical Synthesis of a Binding Site for HIV–1 on the CD4 Protein" *Science* 240:1335–1339.

Jones et al. (1986) "Replacing the Complementarily–Determining Regions in a Human Antibody with those from a Mouse" *Natural* 321:522–525.

Kalyanaraman et al. (1990) "Evidence by Peptide Mapping that the Region CD4 (81–92) is Involved in gp120/CD4 Interaction Leading of HIV Infection and HIV–Induced Syncytium Formation" *J. of Immunology* 145:4072–4078.

Keefer et al. (1994) "Studies of High Doses of a Human Immunodeficiency Virus Type 1 Recombinant Glycoprotein 160 Candidate Vaccines in HIV Type 1–Seronegative Humans" *AIDS Research and Human Retroviruses* 10:1713–1723.

Kennett et al. (1980) "Method for Production and Characterization of Monoclonal Antibodies" *Monoclonal Antibodies, Hybridomas: A New Dimension in Biological Analyses,* pp. 363–419.

Knapp et al. eds. *Immunofluorescence and Related Staining Techniques,* Elsevier/North Holland Biomedical Press, 1978 p. 215.

Koff et al., ed., (1993) "High–Titer Neutralization of Multiple HIV–1 Isolates by Radially Branched Immunogens" *AIDS Research Reviews,* Chapter 18, Marcel Dekker: New York pp. 345–361.

Köhler et al. (1975) "Continuous Cultures of Fused Cells Secreting Antibody of Predefined Specificity" *Nature* 256:495–497.

Landau et al. (1988) "The Envelope Glycoprotein of the Human Immunodeficiency Virus Binds to the Immunoglobulin–Like Domain of CD4" *Nature* 334:159–162.

Lewis et al. (1993) "Passively Transferred Antibodies Directed Against Conserved Regions of SIV Envelope Protect Macaques from SIV Infection" *Vaccine* 11:1347–1355.

Loetscher et al. (1994) "Cloning of a Human Seven–Transmembrane Domain Receptor, LESTR, That Is Highly Expressed in Leukocytes" *J. of Biological Chemistry* 264:232–237.

Mascola et al. (1996) "Immunization with Envelope Subunit Vaccine Products Elicits Neutralizing Antibodies against Laboratory–Adapted but Not Primary Isolates of Human Immunodeficiency Virus Type 1" *J. of Infectious Diseases* 173:340–348.

Meloen et al. (1991) "The Use of Peptides to Reconstruct Conformational Determinants; a Brief Review" *Ann. Biol. Clin.* 49:231–242.

Morrison et al. (1984) "Chimeric Human Antibody Molecules: Mouse Antigen–Binding Domains with Human Constant Region Domains" *Proc. Nat'l Acad. Sci, U.S.A.* 81:6851–6855.

Montefiori et al. (1994) "Complement Control Proteins, CD46, CD55, and CD59 as Common Surface Constituents of Human and Simian Immunodeficiency Viruses and Possible Targets for Vaccine Protection" *Virology* 205:82–92.

Montefiori et al. (1995) "New Insights into the Role of Host Cell Proteins in Antiviral Vaccine Protection" *AIDS Research and Human Retroviruses* 11:1429–1431.

Murphey–Corb et al. (1989) "A Formalin–Inactivated Whole SIV Vaccine Confers Protection in Macaques" *Science* 246:1293–1297.

NIH AIDS and Research and Reference Reagent Program Catalog No. 207.

Peterseon et al. (1988) "Genetic Analysis of Monoclonal Antibody and HIV Binding Sites on the Human Lymphocyte Antigen CD4" *Cell* 54:65–72.

Pierce Chemical Co., Rockford IL, Cat. No. 21221.

Prince et al. (1991) "Prevention of HIV Infection by Passive Immunization with HIV Immunoglobulin" *AIDS Research and Human Retroviruses* 7:971–973.

Putkonen et al. (1991) "Prevention of HIV–2 and $SIV_{sm}$ Infection by Passive Immunization in Cynomolgus Monkeys" *Nature* 352:436–438.

Rieber et al. (1990) "Monoclonal CD4 Antibodies after Accidental HIV Infection" *The Lancet* 336:1007–1008.

Rieber et al. (1992) "The Monoclonal CD4 Antibodies M–T413 Inhibits Cellular Infection with Human Immunodeficiency Virus after Viral attachment to the Cell Membrane: An Approach to Postexposure Prophylaxis" *Proc. Nat'l. Acad. Sci. U.S.A.* 89:10792–10796.

Rowe (1996) "A Cofactor for HIV–1 Entry into Cells is Identified" *Science and Medicine* 347:1395.

Ryu et al. (1990) "Crystal Structure of an HIV–Binding Recombinant Fragment of Human CD4" *Nature* 348:419–426.

Safrit et al. (1993) "hu–PBL–SCID Mice can be Protected from HIV–1 Infection by Passive Transfer of Monoclonal Antibody to the Principal Neutralizing Determinant of Envelope gp120" *AIDS* 7:15–21.

Sastry et al. (1989) "Cloning of the Immunological Repertoire in *Escherichia Coli* for Generation of Monoclonal Catalytic Antibodies: Construction of a Heavy Chain Variable Region–Specific cDNA Library" *Proc. Nat'l. Acad. Sci. U.S.A.* 86:5728–5732.

Sattentau et al. (1989) "Structure Analysis of the Human Immunodeficiency Virus–Binding Domain of CD4" *J. Exp. Med.* 170:1319–1334.

Sattentau et al. (1986) "Epitopes of the CD4 Antigen and HIV Infection" *Science 234:*1120–1123.

Sawyer et al. (1994) "Neutralization Sensitivity of Human Immunodeficiency Virus Type 1 is Determined in Part by the Cell in Which the Virus is Propagated" *J. of Virology 68:*1342–1349.

Stott (1991) "Anti–Cell Antibody in Macaques" *Nature 353:*393.

Smith et al. (1984) "Monoclonal Antibody and Enzymatic Profiles of Human Malignant T–Lymphoid Cells and Derived Cell Lines" *Cancer Research 44:*5657–5660.

Wang et al. (1991) "Long–Term High–Titer Neutralizing Activity Induced by Octameric Synthetic HIV–1 Antigen" *Science 254:*285–288.

Wang et al. (1986) "Stimulation and Expansion of a Human T–Cell Subpopulation by a Monoclonal Antibody to T–Cell Receptor Molecule" *Hybridoma 5:*179–190.

Wang et al. (1990) "Atomic Structure of a Fragment of Human CD4 Containing Two Immunoglobulin–Like Domains" *Nature 348:*411–418.

Watson et al. "The G–Protein Linked Receptor Facts Book" *Chemokines Academic Press* pp. 83–88.

White–Scharf (1993) "Broadly Neutralizing Monoclonal Antibodies to the V3 Region of HIV–1 Can Be Elicited by Peptide Immunization" *Virology 192:*197–206.

Wrin et al. (1995) "Adaptation to Persistent Growth in the H9 Cell Line Renders a Primary Isolate of Human Immunodeficiency Virus Type 1 Sensitive to neutralization by Vaccine Sera" *J. of Virology 69:*39–48.

Deduced Amino Acid Sequence of Human CD4 (Sequence ID No.: 1)

```
         10         20         30         40         50         60         70         80
KKVVLGKKGD TVELTCTASQ KKSIQFHWKN SNQIKILGNQ GSFLTKGPSK LNDRADSRRS LWDQGNFPLI IKNLKIEDSD
                                            └─────────────── 1st Domain
         90        100        110        120        130        140        150        160
TYICEVEDQK EEVQLLVFGL TANSDTHLLQ GQSLTLTLES PPGSSPSVQC RSPRGKNIQG GKTLSVSQLE LQDSGTWTCT
─────────────────────────────────────────────────────────────────────────────────────┘
                                                              2nd Domain
        170        180        190        200        210        220        230        240
VLQNQKKVEF KIDIVVLAFQ KASSIVYKKE GEQVEFSFPL AFTVEKLTGS GELWQAERA SSSKSWIIFD LKNKEVSVKR
                    ↑│↓
                                                                                  3rd Domain
        250        260        270        280        290        300        310        320
VTQDPKLQMG KKLPLHLTLP QALPQYAGSG NLTLALEAKT GKLHQEVNLV VMRATQLQKN LTCEVWGPTS PKLMLSLKLE
            ↑│↓
                                                                                  4th Domain
        330        340        350        360        370        380        390        400
NKEAKVSKRE KPVWVLNPEA GMWQCLLSDS SQVLLESNIK VLPTWSTPVQ PMALIVLGGV AGLLLFIGLG IFFFCVRCHR
                                                     ↑│↓
                                                                    ←── Transmembrane Region ──→
        410        420        430 433
RRQAERMSQI KRLLSEKKTC QCPHRFQKTC SPI
         ↑──
Cytoplasmic Tail
```

FIG. 1

Caps (MAbs B4 and M2)

Patches (MAbs E6, E2, H5, D5, E2, J33 and GPαrsCD4 serum)

Clusters (FITC labelled HIV-1 gp120)

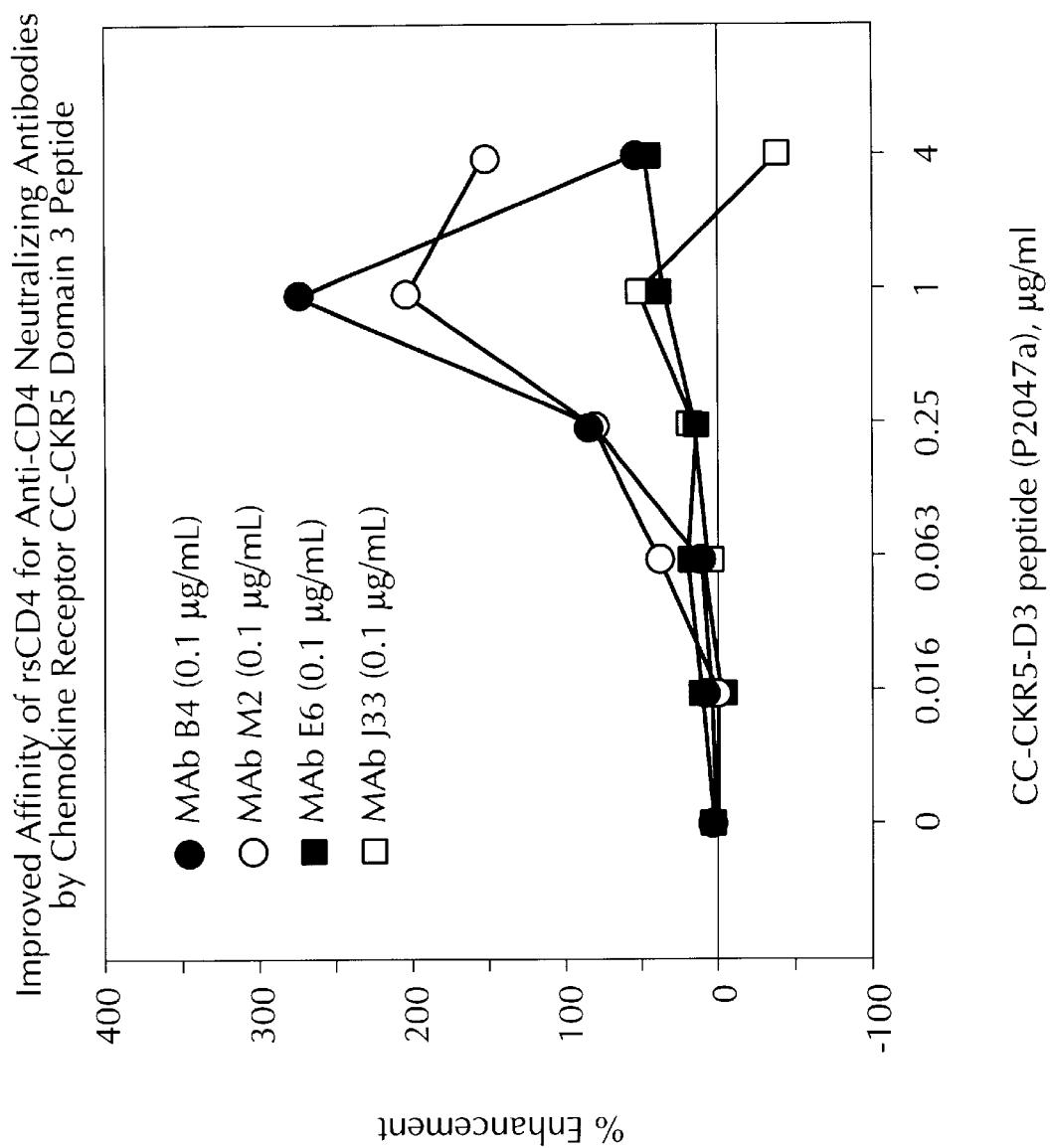

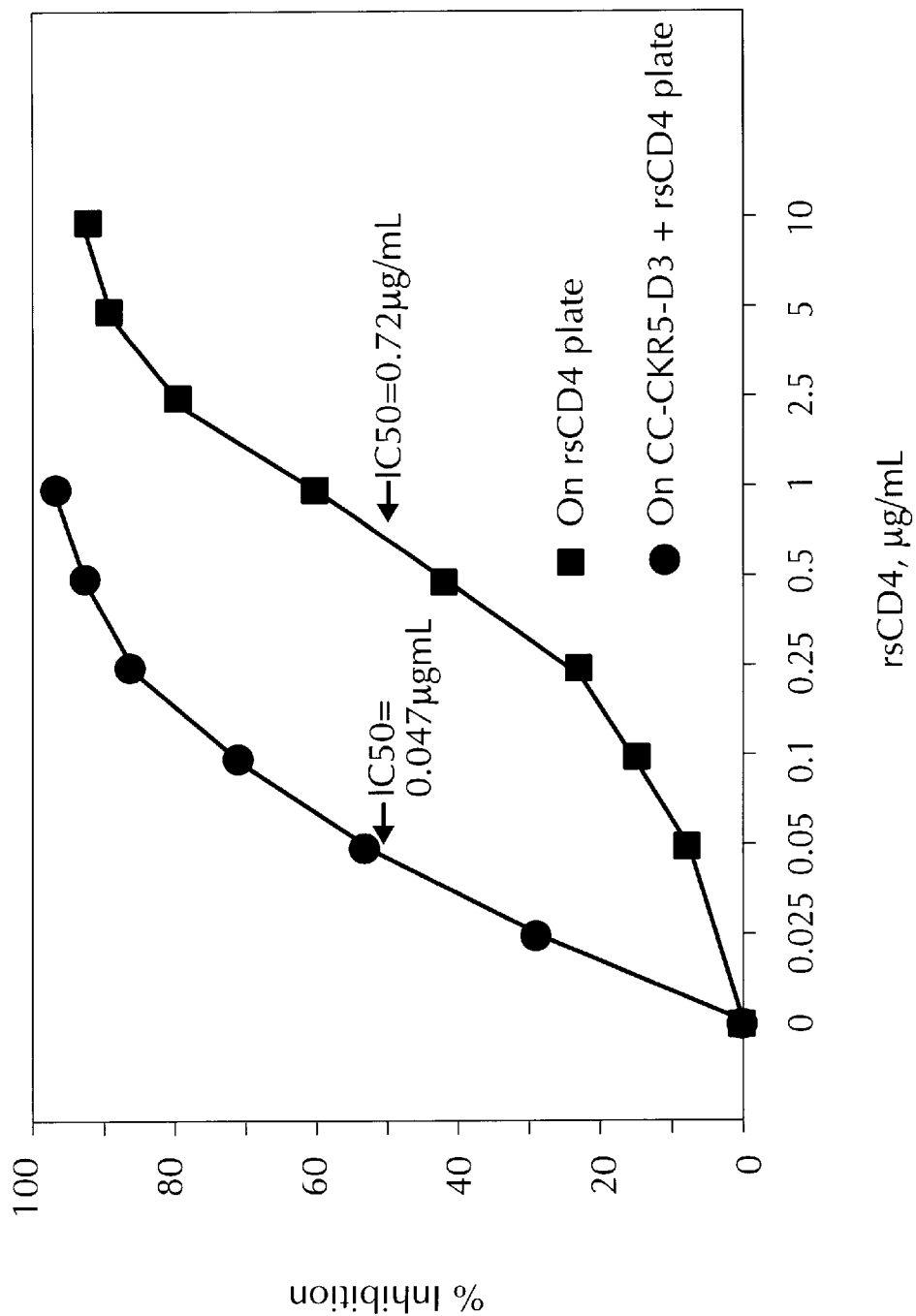

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 433 amino acids
      (B) TYPE: amino acid
      (D) TOPOLOGY: linear (ii) MOLECULE TYPE: peptide (xi) SEQUENCE DESCRIPTION: SEQ ID NO:1:

```
Asn Lys Val Val Leu Gly Lys Lys Gly Asp Thr Val
                  5                  10

Glu Leu Thr Cys Thr Ala Ser Gln Lys Lys Ser Ile
            15                  20

Gln Phe His Trp Lys Asn Trp Asn Gln Ile Lys Ile
25                  30                  35
```

-continued

```
Leu Gly Asn Gln Gly Ser Phe Leu Thr Lys Gly Pro
            40                  45
Ser Lys Leu Asn Asp Arg Ala Asp Ser Arg Arg Ser
 50                  55                      60
Leu Trp Asp Gln Gly Asn Phe Pro Leu Ile Ile Lys
                65                  70
Asn Leu Lys Ile Glu Asp Ser Asp Thr Tyr Ile Cys
         75                  80
Glu Val Glu Asp Gln Lys Glu Val Gln Leu Leu
 85                  90                  95
Val Phe Gly Leu Thr Ala Asn Ser Asp Thr His Leu
            100                 105
Leu Gln Gly Gln Ser Leu Thr Leu Thr Leu Glu Ser
 110                 115                     120
Pro Pro Gly Ser Ser Pro Ser Val Gln Cys Arg Ser
            125                 130
Pro Arg Gly Lys Asn Ile Gln Gly Gly Lys Thr Leu
 135                     140
Ser Val Ser Gln Leu Glu Leu Gln Asp Ser Gly Thr
145                  150                 155
Trp Thr Cys Thr Val Leu Gln Asn Gln Lys Lys Val
            160                 165
Glu Phe Lys Ile Asp Ile Val Val Leu Ala Phe Gln
 170                     175                 180
Lys Ala Ser Ser Ile Val Tyr Lys Lys Glu Gly Glu
                185                 190
Gln Val Glu Phe Ser Phe Pro Leu Ala Phe Thr Val
            195                 200
Glu Lys Leu Thr Gly Ser Gly Glu Leu Trp Trp Gln
205                  210                 215
Ala Glu Arg Ala Ser Ser Ser Lys Ser Trp Ile Ile
            220                 225
Phe Asp Leu Lys Asn Lys Glu Val Ser Val Lys Arg
 230                 235                     240
Val Thr Gln Asp Pro Lys Leu Gln Met Gly Lys Lys
            245                 250
Leu Pro Leu His Leu Thr Leu Pro Gln Ala Leu Pro
     255                 260
Gln Tyr Ala Gly Ser Gly Asn Leu Thr Leu Ala Leu
265                  270                 275
Glu Ala Lys Thr Gly Lys Leu His Gln Gly Val Asn
            280                 285
Leu Val Val Met Arg Ala Thr Gln Leu Gln Lys Asn
 290                 295                     300
Leu Thr Cys Glu Val Trp Gly Pro Thr Ser Pro Lys
            305                 310
Leu Met Leu Ser Leu Lys Leu Glu Asn Lys Glu Ala
            315                 320
Lys Val Ser Lys Arg Glu Lys Pro Val Trp Val Leu
325                  330                 335
Asn Pro Glu Ala Gly Met Trp Gln Cys Leu Leu Ser
            340                 345
Asp Ser Gly Gln Val Leu Leu Glu Ser Asn Ile Lys
            350                 355                 360
```

```
Val Leu Pro Thr Trp Ser Thr Pro Val Gln Pro Met
              365             370
Ala Leu Ile Val Leu Gly Gly Val Ala Gly Leu Leu
              375             380
Leu Phe Ile Gly Leu Gly Ile Phe Phe Cys Val Arg
385                 390             395
Cys Arg His Arg Arg Gln Ala Glu Arg Met Ser
              400             405
Gln Ile Lys Arg Leu Leu Ser Glu Lys Lys Thr Cys
              410             415             420
Gln Cys Pro His Arg Phe Gln Lys Thr Cys Ser Pro
              425             430
Ile
```

(2) INFORMATION FOR SEQ ID NO:2:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:2:

```
Phe Phe Leu Leu Thr Arg Ile Leu Thr Ile Pro Gln
              5                   10
Ser Leu Ile
        15
```

ANTIBODIES AGAINST A HOST CELL ANTIGEN COMPLEX FOR PRE AND POST EXPOSURE PROTECTION FROM INFECTION BY HIV

CROSS REFERENCE TO RELATED INVENTIONS

This invention is a continuation-in-part of copending application Ser. No. 08/808,374, filed Feb. 28, 1997, which is in turn a continuation-in-part application of application, U.S. Ser. No. 08/657,149, filed Jun. 3, 1996, now abandoned.

SUMMARY OF INVENTION

This invention is directed to monoclonal antibodies produced by using CD4-expressing T lymphocytes, such as peripheral blood mononuclear T cells, thymocytes, splenocytes and leukemia or lymphoma derived T cell line cells such as HPB-ALL or SUP-T as the immunogen in accordance with the protocols and screening procedures described. The monoclonal antibodies of the present invention are characterized by their ability to neutralize in vitro and in vivo primary isolates of Human Immunodeficiency Virus (HIV) and related immunodeficiency viruses. The antibodies are directed against a host cell antigen complex comprising CD4 protein in association with domains from chemokine receptors and have broad neutralizing activities against primary isolates from all clades of HIV type 1 (HIV-1) and primary isolates of HIV type 2 (HIV-2) and Simian Immunodeficiency Virus (SIV). The present invention is also directed to a method of selecting and producing such antibodies, hybridomas which secrete such antibodies, pharmaceutical compositions comprising such antibodies and methods for pre- and post-exposure prevention of immunodeficiency virus infection in primates, including humans, by such antibodies whose primary targets are CD4 expressing lymphocytes.

BACKGROUND OF THE INVENTION

Notwithstanding intensive research for a vaccine in the 12 years since the initial discovery of HIV as the Acquired Immunodeficiency Syndrome (AIDS) virus and 10 years since the molecular cloning and characterization of the AIDS virus, major obstacles remain for HIV vaccine and immunotherapy development. These hurdles include HIV-1 variability, multiple routes/modes of virus transmission, and a lack of understanding of the immune responses necessary for prevention of HIV infection. In an article published on Jul. 28, 1995 (Cell 82:175–176), David Baltimore asked all scientists in the field to take a step back and reflect on why this virus infection, against which 10% of the budget of the U. S. National Institutes of Health (NIH) is deployed, remains so enigmatic.

There was early optimism for efficacious recombinant HIV-1 envelope subunit vaccines (e.g., gp120 and gp160 vaccine products) given that vaccinee sera from several clinical trials were capable of neutralizing laboratory isolates of HIV-1 in vitro (Belshe et al., *JAMA*, 1994, 272:475; Keefer et al., *AIDS Res Hum Retroviruses*, 1994, 10:1713). This optimism was shaken when the vaccinee sera were found to be largely ineffective in neutralizing HIV-1 primary patient isolates (Hanson, *AIDS Res Hum Retroviruses*, 1994, 10:645; Mascola et al., *J Infect Dis*, 1996, 173:340). These disappointing findings led NIH to decide in June 1994 to postpone costly large-scale efficacy trials of several recombinant envelope protein based HIV subunit vaccines.

Primary isolates of HIV-1 are obtained by limited cultivation of patient peripheral blood mononuclear cells (PBMCs) or plasma with uninfected PBMCs. They closely resemble HIV strains responsible for human infection in the field (Sawyer et al., *J Virol*, 1994, 68:1342; Cornelissen et al., *J Virol*), 1995, 69:1810). Primary isolates can be readily distinguished from the commonly used laboratory-adapted T-tropic viruses such as IIIb/LAI, SF2, and MN, which have been passaged over time in human T-lymphoid cell lines and are well-adapted to grow in these T cell lines. First, most primary isolates are M-tropic. They do not readily grow in cultured T cell lines, rather, they are monocytes- or macrophage-tropic, although they can also infect primary T cells (Cheng-Mayer et al., *Science*, 1988, 240:80). Second, primary isolates are highly resistant to in vitro neutralization by recombinant soluble forms of the viral receptor protein CD4 (rsCD4) requiring 200–2700 times more rsCD4 than laboratory strains for comparable neutralization (Daar et al., *PNAS USA*, 1990, 87:6574–6578). Third, primary isolates are also resistant to neutralizing antibodies elicited by the use of gp120 vaccines (Mascola et al.).

Primary isolates include both syncytium inducing isolates (SI) that induce syncytium formation in PBMC culture and non-syncytium-inducing (NSI) isolates. Among the SI primary isolates, most will replicate in the especially HIV-sensitive T cell line MT2, but few can replicate in the less permissive transformed T cell lines such as CEM or H9 that are commonly used for the culture of laboratory-adapted isolates. Non-syncytium-inducing (NSI) primary isolates can be cultured only in the primary T cells from peripheral blood.

Early optimism for an AIDS vaccine was also engendered from studies on inactivated virus preparations of Simian Immunodeficiency Virus (SIV). Similarities between HIV-1 and SIV in morphology, genetic organization, infection and disease processes made SIV infection in rhesus monkeys an excellent model in which to explore different AIDS vaccine strategies. Early studies in this model showed that inactivated preparations of SIV grown on human T cell lines and formulated in adjuvant can protect macaques from infection after experimental inoculation with highly infectious, pathogenic variants of human cell-grown SIV (Desrosiers et al., *PNAS USA*, 1989, 86:6353–6357; Murphey-Corb et al., *Science*, 1989, 246:1293). Unexpectedly, this protection was lost when the SIV stock grown on homologous monkey cells was used for the challenge of immunized animals.

Later it was shown through immunization studies with monkey cell-grown SIV and uninfected human cells that protection from infection in those early SIV studies probably resulted from the stimulation of immune responses to xenogeneic human host cell proteins rather than to virus-encoded antigens (Stott, *Nature*, 1991, 353:393). Passive immunization experiments involving SIV have provided some evidence to suggest that certain anti-cell antibodies may contribute to protection against SIV infection in the absence of cell-mediated immunity (Gardner et al., *AIDS Res Hum Retroviruses*, 1995, 11:843–854).

The mechanism for the protective immunity to SIV challenge provided by anti-cell antibodies has not been delineated. One proposed mechanism is that the anti-cell mediated protection from SIV infection may involve virus-associated cell proteins. Immunodeficiency viruses such as HIV and SIV are known to incorporate cellular proteins probably obtained from the host cell as the viruses bud from the host cell membrane. Antibodies to some of the major histocompatibility complex (MHC) associated cellular proteins, $\beta_2$-microglobulin, HLA-DR, and HLA class I molecules, have been implicated in the in vitro neutralization of laboratory strains of SIV and HIV-1 (Arthur et al., *Science,* 1991, 258:1935). In addition to the MHC associated surface proteins, Montefiori et al. (*Virology,* 1994, 205:82; *AIDS Res Hum Retroviruses,* 1995, 11:1429) recently identified three complement control proteins, CD46, CD55, and CD59, on the surface of human cell-grown SIV and HIV-1 raising the possibility that these host cell molecules could also be utilized by the viruses as a mechanism to evade complement virolysis. An alternative proposed mechanism is that protection by anti-cell antibodies may be mediated by blocking the activity of immunodeficiency viruses against immune system cells in a previously unrecognized manner. There appears to be a host cell antigen complex associated with CD4 on the surface of the host T-cells which facilitates viral binding and entry and which may act as a target for protective anti-cell antibodies.

In addition to the CD4 receptor of the host antigen complex for binding HIV, other factors or HIV co-receptors affecting HIV replication, entry or fusion have recently been reported while the work on the present invention was on-going. These include three chemokines produced by $CD8^+$ T cells (Cocchi et al., *Science,* 1995, 270:1811–1815) which are reported to be HIV suppressive; a co-receptor CXC-CKR4 (also termed fusin or LESTR) on CD4 expressing cells for T-tropic but not M-tropic HIV-1 fusion and entry (Feng et al., *Science,* 1996, 272:873), a β-chemokine receptor CC-CKR5 which binds the three inhibitory chemokines (Cocchi et al.) as a co-receptor for M-tropic, but not T-tropic HIV-1 (Doranz et al., *Cell,* 1996, 85:1149; Dragic et al., *Nature,* 1996, 381:667; Choe et al. *Cell,* 1996, 85:1135; Deng et al., *Nature,* 1996, 381:661; Alkhatib et al., *Science,* 1996, 272:1955), and other β-chemokine receptors (CC-CKR2b and CC-CKR3) as co-receptors for M- and dual-tropic HIV (Doranz et al., *Cell,* 1996, 85:1149). These co-receptors are disclosed to be previously described G protein coupled receptors with seven transmembrane segments (Loetscher et al., *J Biol Chem,* 1994, 264:232; Samson et al., *Biochemistry,* 1996, 35:3362).

To more precisely identify the putative cellular protein that may be stimulating protective responses, and to better characterize the mechanism of protection mediated by anti-cell antibodies, HIV-neutralizing activities were characterized by the present inventor for members of a panel of monoclonal antibodies directed against multiple cellular antigens: $β_2$ microglobulin, MHC class I HLA A,B,C, MHC class II HLA DR proteins, and other T cell antigens associated with a T cell line, to identify those that are capable of neutralizing HIV primary isolates in an in vitro microplaque neutralization assay. Experiments were conducted to determine the scope of such neutralizing activity, if any, for the antibodies found to possess such activity; and to determine whether such in vitro activity can be translated into in vivo efficacy in an appropriate animal model(s).

The results of these experiments demonstrated that, except for antibodies directed against a host cell antigen complex comprising CD4, no other anti-cell antibodies including exclusively CD4-specific antibodies, can neutralize HIV-1 primary isolates as effectively in neutralization assays. The results also showed that antibodies directed against a host cell antigen complex comprising CD4 in association with domains from chemokine receptors exhibit enhanced binding with rsCD4. Further, antibodies with the desired properties are identified and can block in vivo SIV infection in monkeys and in vivo HIV-1 infection of the human immune system reconstituted in mice.

BRIEF DESCRIPTION OF THE INVENTION

The present invention provides, for the first time, antibodies and homologs thereof capable of: (1) blocking HIV binding to CD4 expressing cells, (2) blocking HIV-induced syncytia formation between CD4 expressing cells, (3) neutralizing effectively in vitro infection of CD4 positive cells by primary isolates from all clades of HIV type 1, and from diverse primary isolates of HIV type 2 and SIV, (4) neutralizing effectively in vitro infection of CD4 positive cells by primary isolates of HIV-1 both pre- and post-exposure to these viruses, and (5) preventing infection of primates including rhesus monkeys and humans by primary isolates of HIV and SIV when these antibodies are administered via a parenteral, i.e. intravenous or intraperitoneal, route, and (6) preventing infection of human peripheral blood lymphocyte-reconstituted SCID (hu-PBL-SCID) mice by primary isolates of HIV-1 in both pre- and post-exposure modes.

This invention is, therefore, directed to monoclonal antibodies which bind to a human host cell antigen complex comprising CD4 on the surface of human CD4-expressing cells with the capacity to neutralize primary isolates of HIV, i.e. patient isolates passaged no more than 3–5 times only in peripheral blood mononuclear cells (PBMC). More specifically, this invention relates to antibodies, directed against antigenic determinants present on a surface-exposed host cell antigen complex comprised of the CD4 protein in association with domains from chemokine receptors such as CC-CKR5, having broad and efficacious neutralizing activities against primary isolates from all clades of HIV-1 and diverse primary isolates of HIV-2 and SIV. The present invention is also directed to a process of producing the antibodies by immunizing, via intravenous and/or intraperitoneal route, a non-human mammal with $5–10×10^6$ CD4 expressing cells, preferably cells from a human T leukemia or lymphoma derived cell line such as HPB-ALL from a patient with T acute lymphoblastic leukemia, or SUP-T from a patient with T-cell non-Hodgkin's lymphoma, washed and resuspended in PBS or an adjuvant such as complete Freund's adjuvant; followed by more than two subsequent intravenous or intraperitoneal injections of $5–10×10^6$ washed cells resuspended in PBS without adjuvant. The antibodies produced by the immunized animals are recognized by the ability of their serum antibodies to bind to:

1. rsCD4;
2. rsCD4 in association with domains from chemokine receptors with an enhanced reactivity;
3. the surface of CD4 expressing cells including the HPB-ALL or SUP-T cells in a "caps", manner as shown in a high resolution fluorescence microscope;
4. any of the peptides: $AA_1–AA_{20}$, $AA_{81}–AA_{92}$, $AA_{79}–AA_{88}$, $AA_{60}–AA_{109}$, $AA_{118}–AA_{165}$, $AA_{235}–AA_{251}$, $AA_{297}–AA_{351}$, or $AA_{361}–AA_{375}$ derived from rsCD4; and
5. to neutralize primary isolates of HIV.

The antibodies of the present invention may further be characterized as providing passive immunity from infection by primary isolates of HIV or SIV to primates or hu-PBL/SCID mice, at an $ED_{50}$ of <50 mg/kg.

The present invention also includes the hybridomas which secrete the antibodies having these characteristics. Also contemplated are pre- and post-exposure prophylactic compositions comprising these antibodies for the prevention of immunodeficiency virus infection in primates, including humans, caused by infectious agents whose primary targets are CD4 expressing lymphocytes. The antibodies and homologs thereof of this invention recognize "discontinuous scattered conformational" epitopes on a host cell antigen complex comprising the CD4 molecule particularly when associated with domains from other chemokine receptors such as CC-CKR5 present on CD4 expressing cells. The antibodies bind to synthetic mimetics derived from any of the four extracellular domains of human CD4 (Table 1; SEQ ID NO:1) comprising peptides: $AA_1$–$AA_{20}$, $AA_{81}$–$AA_{92}$, $AA_{79}$–$AA_{88}$, $AA_{60}$–$AA_{109}$, $AA_{118}$–$AA_{165}$, $AA_{235}$–$AA_{251}$, $AA_{297}$–$AA_{351}$, or $AA_{361}$–$AA_{375}$ of CD4.

The present invention also relates to antibody homologs. These include monoclonal antibodies, recombinant antibodies, recombinant chimeric antibodies with antibody domains from one species of an animal fused to human antibody domains and humanized antibodies. The antibody homologs of the invention preferably are intact immunoglobulin molecules having heavy and light chains. In addition, the CD4 reactive antibody homologs of this invention may be in the form of Fab fragments, Fab' fragments, $F(ab')_2$ fragments, F(v) fragments or any other immunoglobulin fragment having the above-described binding properties.

Provided as preferred antibodies or antibody homologs by this invention are the mouse monoclonal antibodies designated B4 or M2 or B13. Also provided are hybridomas that produce the antibody homologs of this invention, a process for selecting and producing the antibody homologs by culturing these cells, and a process for producing the hybridomas of this invention.

FIG. 2A, FIG. 2B and FIG. 2C show schematic representations of the three theoretically possible epitope configurations. The antibody is represented only as a rough outline of the Fv fragment. The filled boxes indicate that part of antibody which contacts the amino acids of the epitope. The amino acids of the epitope are represented by small circles. If the amino acids of the epitope form a single continuous peptide sequence, the epitope is considered to be "linear" (e.g. MAbs E31 and E6); if the amino acids are spread out on two or a few peptide stretches which are spatially adjacent due to conformational folding, the epitope is termed "discontinuous" (e.g. MAbs J33, H5, D5, E2 and I26). The most extreme case has been called "discontinuous scattered" in which numerous discontinuous sites, derived from either one or more than one molecule in a complex, combine by conformational folding to form an extended epitope (e.g. the epitopes of MAbs B4 and M2) (modified from Meloen et al., *Ann Biol Clin,* 1991, 49:231).

FIG. 3A, FIG. 3B and FIG. 3C depict in schematic drawings the three different types of binding to CD4 expressing HPB-ALL cells: caps, patches and clusters, observed for six bona fide anti-CD4 antibodies, two antibodies recognizing a host cell antigen complex comprising CD4 in association with a chemokine receptor, and a guinea

TABLE 1

CD4 Peptides for Anti-CD4 Epitope Mapping Experiments

| Peptide Antigen | | Peptide Antigen | | Peptide Antigen | | Peptide Antigen | |
|---|---|---|---|---|---|---|---|
| Code | Description | Code | Description | Code | Description | Code | Description |
| p1403a | CD4(41–55) | p1483a | CD4(238–249) | p1590a | (C)CD4(104–115)(C)* | p1624a | (C)CD4(36–47)(C)* |
| p1405a | CD4(81–92) | p1485a | CD4(168–179) | p1608a | CD4(16–25)(C)* | p1687a | (C)CD4(349–353)(C)* |
| p1460c | CD4(60–109) | p1486a | CD4(126–137) | p1609a | (C)CD4(118–128)(C)* | p1689a | (C)CD4(213–226)(C)* |
| p1461a | (C)CD4(35–59)(C)* | p1487a | CD4(114–125) | p1610a | (C)CD4(127–141)(C)* | p1693a | (C)CD4(235–251)(C)* |
| p1462a | CD4(29–59) | p1488a | CD4(118–129) | p1611a | (C)CD4(138–146)(C)* | p1701a | CD4(361–375) |
| p1468a | CD4(47–64) | p1489a | CD4(102–113) | p1614a | (C)CD4(38–45)(C)* | p1702a | CD4(14–22) |
| p1a574 | CD4(364–375) | p1490a | CD4(94–105) | p1615a | (C)CD4(39–44)(C)* | p1761a | CD4(123–134) |
| p1476a | CD4(352–363) | p1491a | CD4(90–101) | p1616a | (C)CD4(40–43)(C)* | p1767b | HBVTh-GG-CD4(6–20)‡ |
| p1477a | CD4(340–351) | p1492a | CD4(85–96) | p1617a | (C)CD4(52–54)(C)* | p1768a | CD4(154–165) |
| p1478a | CD4(324–335) | p1493a | CD4(138–149) | p1618a | (C)CD4(51–55)(C)* | p1768b | HBVTh-GG-CD4(154–165)‡ |
| p1479a | CD4(318–329) | p1494a | CD4(160–171) | p1619a | (C)CD4(48–52)(C)* | p1813b | HBVTh-GG-CD4(79–88)‡ |
| p1480a | CD4(303–314) | p1495a | CD4(206–217) | p1620a | (C)CD4(85–90)(C)* | p1816d | CD4(1–20) |
| p1481a | CD4(297–308) | p1496a | CD4(218–229) | p1622a | (C)CD4(104–108)(C)* | p1868a | CD4(297–351)* |
| p1482a | CD4(276–287) | p1589a | (C)CD4(79–96)C)* | p1623a | (C)CD4(108–112)(C)* | | |

*: The peptide is cyclized through the two internal cysteine residues that are present either as part of the CD4 peptide segment or by design added to the N and C termini of the CD4 peptide segment to facilitate the cyclization.
(C): An additional cysteine added to the existing CD4 peptide fragment.
‡: HBVTh (FFLLTRILTIPQSLD, SEQ ID No:2) represents peptide segment with promiscuous T helper function derived from HBsAg protein
GG: (Gly—Gly) as spacer residues inserted in between the CD4 site and the T helper epitope.

BRIEF DESCRIPTION OF THE DRAWINGS

FIG. 1 depicts the amino acid sequence of human CD4 (SEQ ID NO. 1), a part of the host antigen complex, as deduced from nucleic acid sequence. The amino acids are represented by single letter codes as follows:

| Ala: A | Cys: C | His: H | Met: M | Thr: T |
| Arg: R | Gln: Q | Ile: I | Phe: F | Trp: W |
| Asn: N | Glu: E | Leu: L | Pro: P | Tyr: Y |
| Asp: D | Gly: G | Lys: K | Ser: S | Val: V |

Figure 3A:
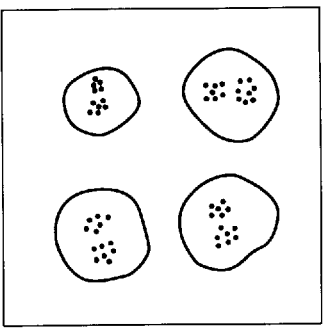
Figure 3B:
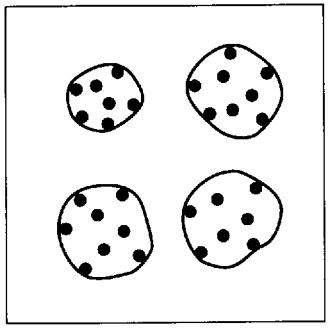
Figure 3C:
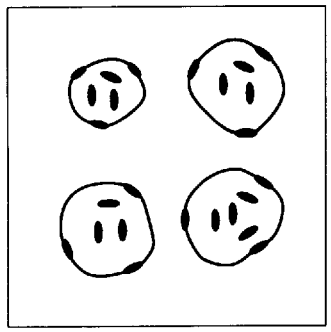

Using the corrected numbering system of Littman et al. (*Cell,* 1988, 55:541), $AA_1$–$A_{110}$, $AA_{111}$–$AA_{181}$, $AA_{182}$–$AA_{287}$, $AA_{288}$–$AA_{375}$, $AA_{376}$–$AA_{393}$, $AA_{394}$–$AA_{433}$ represent respectively the first, second, third, and fourth extracellular domains, the transmembrane domain, and the cytoplasmic domain of the CD4 molecule.

pig αrsCD4 serum. In an immunofluorescence assay, the binding of B4 or M2 to HPB-ALL cells is manifested as fluorescent spots in the shape of "caps" (FIG. 3) on the cells under a high resolution fluorescence microscope. The binding for each of the anti-CD4 antibodies or the guinea pig αrsCD4 to the HPB-ALL cells is manifested as fluorescent spots in the shape of "patches" (FIG. 3). The binding of FITC labelled HIV-1 gp120 protein to the HPB-ALL cells is manifested as fluorescent spots in the shape of "clusters" (FIG. 3).

FIG. 4 depicts % Enhancement of rsCD4 binding activity for various monoclonal antibodies exerted by chemokine receptor CC-CKR5 domain 3 peptide (p2047a) in a dose dependency study.

FIG. 5 depicts the quantitation ($IC_{50}$ rsCD4) of the enhanced affinity of MAb B4 for the rsCD4/chemokine receptor CC-CKR5 domain 3 peptide mixture vs rsCD4.

DETAILED DESCRIPTION OF THE INVENTION

As used herein, "primary isolates of human immunodeficiency virus type 1 (HIV-1)" are obtained by limited cultivation, of up to five passages, of patient peripheral blood mononuclear cells (PBMCs) or plasma with uninfected PBMCs. The primary isolates can be distinguished by three important properties from the laboratory-adapted strains such as IIIb/LAI, SF2 and MN which have been passaged over time in human T-lymphoid cell lines. First, most primary isolates do not readily grow in T cell lines. For example, many primary isolates that induce syncytium formation in PBMC culture (SI isolates) will replicate in the especially HIV-sensitive MT2 T cell lines, but few replicate in less permissive T cell lines such as CEM or H9. Non-syncytium-inducing (NSI) primary isolates will replicate only in primary T cells. Second, they differ from laboratory-adapted strains in their sensitivity to in vitro neutralization by recombinant soluble forms of the viral receptor protein CD4 (rsCD4) (Daar et al., *PNAS USA,* 1990, 87:6574–6578). Third, the laboratory-adapted strains are sensitive to neutralization by antibodies with specificities for the viral envelope, while primary isolates are resistant (Sawyer et al., *J Virol,* 1994, 68:1342; Mascola et al., *J Infect Dis,* 1996, 173:340). As shown in Example 1, Table 2, laboratory strains, such as HIV-1 MN, are quite sensitive to neutralization by anti-V3 antibodies while two primary isolates are resistant, even to an anti-V3 preparation with a neutralization titer against HIV-1 MN of 1:203,080.

However, the neutralization of HIV laboratory strains and primary isolates by anti-cell antibodies follows a different trend than the anti-envelope antibodies. In Example 2 Table 3, monoclonal antibodies directed against $\beta_2$ microglobulin, MHC class I HLA A,B,C, and MHC class II HLA DR, and other well-characterized T cell surface antigens did not inhibit infection by either the laboratory cell line-derived HIV-1 MN strain or by an HIV-1 B clade primary isolate, whereas a monoclonal antibody (MAb B4) produced against HPB-ALL having a moderate reactivity against the rsCD4 protein and a strong binding to the HPB-ALL cells and to the rsCD4 protein in association with domains from chemokine receptors such as CC-CKR5, was found highly effective in neutralizing primary isolates of HIV-1 (Tables 3, 7 and 13) but less effective in neutralizing a laboratory cell line-derived HIV-1 MN strain (Table 13). It was found that B4 neutralized HIV primary isolates in an in vitro microplaque assay at a concentration of <10 μg/mL (Tables 3, 7 and 13) at a much greater efficiency than antibodies with exclusive CD4 specificity (Table 7). Thus, the primary isolates appear to be preferentially sensitive to the anti-CD4-comprising host cell antigen complex antibody.

It was also found that the neutralizing activity of MAb B4 extends to include cross-neutralization of HIV-2 and SIV (Table 14). These results (Tables 7, 13) strongly suggest that among the cellular proteins associated with HIV, there is a host cell antigen complex comprising CD4 and co-receptor (s), e.g. the chemokine receptor CC-CCKR5, which is a target for the cross-neutralizing antibody. The co-receptor(s) is(are) delineated as co-receptor(s) for HIV fusion, entry or suppressive factors.

The mechanism for the broad neutralizing activity of anti-antigen complex comprising CD4 is unclear. The CD4 comprising host cell antigen complex may play dual roles in mediating HIV infection and pathogenesis: as both a T cell surface receptor for HIV binding and a receptor for cell fusion and entry by HIV or an HIV suppressive factor. As used herein, "host cell antigen complex comprising CD4 protein" refers to a complex containing a receptor for HIV binding and associated co-receptor(s), e.g. CC-CCKR5, for an HIV suppressive factor or cell fusion and entry by HIV. This molecular complex is exclusively expressed on the surface of a CD4 expressing cell. Serologically and functionally, it is distinct from the recombinantly expressed soluble CD4 protein molecule.

As used herein, "CD4" means any CD4 protein encoded by a naturally occurring CD4 gene.

As used herein, "CD4 expressing cells or CD4+ cells" are cells that present the CD4 glycoprotein on their surface. Such cells include CD4 expressing T lymphocytes, e.g. peripheral blood T cells, thymocytes, splenocytes, etc. and leukemia or lymphoma derived T cell line cells, e.g., HPB-ALL cells or SUP-T1.

As used herein, "recombinant soluble CD4" or "rsCD4" is a polypeptide consisting of $AA_1$–$AA_{375}$ (FIG. 1, SEQ ID NO:1) of human CD4.

As used herein, "host cell antigen complex comprising CD4" or "cell surface CD4 antigen complex" represents a membrane structure comprising CD4 as a 50 KD glycoprotein comprised of four extracellular domains, a transmembrane domain, and a cytoplasmic domain (FIG. 1, SEQ ID NO:1) which is complexed with other involved host cell proteins, such as domains from chemokine receptors.

CD4 was initially described as a cell surface marker for T-helper lymphocytes. CD4 was subsequently found to be expressed sparsely on monocytes, Langerhans, microglial cells, and subsets of B cells. The CD4 molecule was found also to participate directly in activation of antigen-specific T helper cells through its function as a receptor for the MHC class II molecule. In 1984, human CD4 was found to be the receptor for HIV (Dalgleish et al., *Nature,* 1984, 312:763). Binding of HIV envelope glycoprotein, gp120, to CD4 represents the initial step in viral entry into the target cell.

The CD4 molecule has been mapped extensively by binding studies with panels of CD4 specific monoclonal antibodies and by negative deductions such as correlation of CD4 structural modifications, e.g., substitutions, deletions or insertions of amino acids, with resultant functional changes in CD4 (Sattentau et al., *Science,* 1986, 234:1120; Peterson and Seed, *Cell,* 1988, 54:65; Jameson et al., *Science,* 1988, 240:1335; Sattentau et al., *J Exp Med,* 1989, 170:1319; Hasunuma et al., *J Immunol,* 1992, 148:1841; Burkly et al., *J Immunol,* 1992, 149:1779; Davis et al., *Nature,* 1992, 358:76). Those mapping studies have enabled the construction of a structure-function map for the molecule. Many of the CD4-specific monoclonal antibodies have been found to have neutralizing activities against laboratory strains of HIV. None of the antibodies known to have HIV neutralization activity have been assessed for their ability to inhibit infection in vivo by primary isolates through either a pre- or post-HIV exposure mode. None of these antibodies are reported to be reactive to a host cell antigen complex comprising CD4, particularly when associated with domains from the chemokine receptors.

The first extracellular domain of CD4 shares homologies with immunoglobulin at three complimentarity determining regions (CDRs) similar to that of immunoglobulin chains. Both domain 1 and domain 2 of the extracellular region of the CD4 molecule were found to contribute to the binding sites for class II MHC molecules while domain 1 alone was involved with HIV binding and syncytia formation. The binding sites for the HIV envelope glycoprotein gp120 were found to be localized to the CDR2-like loop of domain 1

(Peterson and Seed, *Cell*, 1988, 54:65; Landau et al., *Nature*, 1988, 334:159; Clayton et al., *Nature*, 1988, 335:363; Arthos et al., *Cell*, 1989, 57:469; Sattentau et al., *J Exp Med*, 1989, 170:1319). A discrete area that overlaps the CDR3 region in domain 1 was found to be involved in syncytia formation (Kalyanaraman et al., *J Immunol*, 1990, 145:4072; Camerini and Seed, *Cell*, 1990, 60:747; Corbeau et al., *J Immunol*, 1993, 150:290).

From these references, it may be concluded that antibodies specific for CD4 probably interact with the immune system in several ways: first, block the CD4-class II interaction between CD4 expressing T cells and other activated T cells, B cells, or monocytes; second, deliver signals to T cells, thus inhibiting normal CD4 T-cell mediated immunoregulatory functions; third, induce cell death of CD4-expressing cells by apoptosis when triggered by a simultaneous engagement of the T cell receptor molecules; and fourth, block interactions between CD4 and HIV, to inhibit HIV-mediated immunopathology. Based on these conclusions, antibodies to CD4 appear to be good candidates to prevent and treat HIV infection and HIV-associated diseases including AIDS. And, on a more general level, antibodies to CD4 may be useful to prevent undesirable immune responses, such as transplant rejection, or cure autoimmune diseases such as rheumatoid arthritis, systemic lupus erythematosus, or psoriasis. Anti-CD4 antibodies have been the subject of many studies. It was hoped that antibodies which block HIV gp120 binding to CD4 would prevent syncytia formation and prevent HIV infection.

Two well-characterized anti-CD4 antibodies, Leu3A and OKT4A, have been shown to effectively block HIV-induced syncytia formation. The epitope recognized by MAb Leu3A has been mapped precisely to a stretch of 15 amino acids $AA_{49}$–$AA_{63}$ overlapping the CDR2 region of the HIV-1 gp120 binding site by Chiba, U.S. Pat. No. 5,171,838. The epitope recognized by MAb OKT4A has been mapped to a CD4 site overlapping the HIV-1 gp120 binding site, between $AA_{16}$–$AA_{49}$ (Jameson et al., *Science*, 1988, 240:1336. Note: There is a 9 amino acid frame shift between the CD4 sequence disclosed in the Jameson publication and that shown in SEQ ID NO:1, FIG. 1 of the present invention). However, both antibodies have been found to have limited applications in the treatment of HIV infection because they fail to bind or act on a CD4 molecule which is already bound to HIV gp120 (Burkly et al., WO 92/09305). There appears to be steric hindrance caused by the proximity of the epitopes to the gp120 binding site.

Other anti-CD4 antibodies that have been reported to have some effect on HIV-induced syncytia formation, including MT151, MT413, 13B8-2, OKT4E, VIT4 and MT321 (Dalgleish et al., *Nature*, 1984, 312:763; Sattentau et al., *Science*, 1986, 234:1120; Davis et al., *Nature*, 1992, 358:76; Corbeau et al., *J Immunol*, 1993, 150:290). These antibodies are reported to bind determinants close to the CDR3-region of the first domain, that are distinct from the epitopes bound by OKT4A and Leu3A. However, like Leu3a and OKT4A, they also fail to bind to CD4 molecules already bound to HIV gp120, limiting their usefulness (Burkly et al., WO 92/09305).

Another group of monoclonal anti-CD4 antibodies, including MAb 5A8, as described in Burkly et al. ibid., were also shown to inhibit HIV mediated syncytia formation. Results of epitope mapping studies (p. 81–82, WO 92/09305) to characterize MAb 5A8 had led to the findings that 5A8 recognized a conformational epitope of CD4 comprising the first and second domains of CD4 and that both are required and "sufficient" for 5A8 binding. It was also found that $AA_{83}$–$AA_{105}$ of the rod-like β strand which connects the first and second domains are influential and $AA_{105}$–$AA_{131}$ of the second domain are absolutely required for 5A8 binding to CD4. There appears to be no involvement of the third and fourth domains of CD4 and of other complexed cell surface antigens.

There have been previous suggestions to employ CD4-reactive monoclonal antibodies which had been shown to inhibit HIV binding to CD4 positive cells and/or to inhibit HIV-induced syncytia formation as passive immunoprophylactic agents to prevent infection by accidental exposure and to interrupt vertical transmission from infected mother to offspring (Rieber et al., *Lancet*, 1990, 336:1007; Rieter et al., *PNAS*, 1992, 89:10792; and Attanasio et al., *J Infect Dis*, 1993, 168:515). However, most of these anti-CD4 antibodies have been assessed merely for their in vitro neutralizing activities against laboratory strains of HIV and none have been assessed for their ability to inhibit infection in vivo by primary isolates through either a pre- or post exposure application.

It is now known that such in vitro viral neutralization results do not translate into in vivo efficacy against HIV. The failure of rsCD4 to exert antiviral effect in HIV-1 infected patients (Daar et al., *PNAS USA*, 1990, 87:6574–6578) despite potent in vitro neutralization capability is especially well-known.

Prior to the present invention, none of the known anti-CD4 antibodies had been reported to be capable of binding to, or intimately contacting, all four domains of CD4, to be capable of blocking the initial binding of HIV gp120 to human CD4 while also effectively neutralizing the infectivity of diverse primary isolates of HIV types 1 and 2 and SIV, and having the capability of doing so through a post-binding anti-viral mechanism.

According to the present invention, antibodies are provided which bind to, or in contact with, all four domains of CD4, and further to have enhanced binding when associated with chemokine receptors. These antibodies are capable of blocking the initial binding of HIV gp120 to human CD4 while also effectively neutralizing the infectivity of primary isolates of HIV-1 from all clades and diverse primary isolates of HIV-2 and SIV, and do so through a post-binding anti-viral mechanism. The monoclonal antibody and homologs of this instant invention mark the first demonstration of in vivo efficacy by an antibody against infection by primary isolates of immunodeficiency viruses both in primates and in a reconstituted human immune system of the huPBL/SCID mouse model (Examples 17 and 18).

Antibodies with these properties, e.g. MAb B4, clearly offer advantages for therapeutic intervention in HIV infection and HIV-related pathologies such as AIDS. Unlike the anti-CD4 antibodies known previously, B4 or its homologs could be used to intervene both before and after HIV binding to the cell surface antigen complex comprising CD4 and it will provide effective protection from infection by divergent primary isolates, including cross-clade protection.

The monoclonal antibodies of the present invention are the first shown to be efficacious in vivo for the neutralization of primary isolates of immunodeficiency viruses in a primate model and in the reconstituted human immune system. The in vitro and in vivo neutralization results of the antibodies of the present invention as shown in the Examples 2–18, together with the highly desirable combination of properties described herein, show that they will be useful in the prevention of HIV infection of humans by worldwide strains of HIV types 1 and 2, both before and after accidental exposure.

The properties of the antibodies useful for the present invention are summarized here based on the results obtained in Examples 2–16 and 19–20:

1. Binding to rsCD4 in an ELISA assay;
2. Binding to CD4-expressing cells in an immunofluorescent assay where the binding pattern is in the shape of "caps" (FIG. 3) when examined with a high resolution fluorescence microscope;
3. Blocking the binding of HIV gp120 to CD4 expressing cells;
4. Binding to CD4 expressing cells previously bound with HIV gp120; and
5. Neutralizing HIV primary isolates in an in vitro microplaque assay at a concentration of <10 $\mu$g/mL, preferably at a concentration in the range of 0.01–10 $\mu$g/mL for 50% neutralization and 0.1–35 $\mu$g/mL for 90% neutralization. Preferably, the antibodies of the present invention also display
6. Enhanced binding to rsCD4 in an ELISA assay when rsCD4 was preincubated with chemokine receptor domain peptides;
7. Binding to any of the four domains of CD4 represented by the peptides: $AA_1$–$AA_{20}$, $AA_{81}$–$AA_{92}$, $AA_{79}$–$AA_{88}$, $AA_{60}$–$AA_{109}$, $AA_{118}$–$AA_{165}$, $AA_{235}$–$AA_{251}$, $AA_{297}$–$A_{351}$, or $AA_{361}$–$AA_{375}$ of CD4;

The antibodies with these characteristics are especially useful in prophylaxis and treatment in humans of diseases caused by infectious agents whose primary targets are CD4 positive cells. Accordingly, the present invention provides prophylactic and therapeutic compositions comprising the antibody or homologs thereof, useful for preventing and treating in humans diseases caused by infectious agents whose primary targets are CD4 positive cells, for example, the HIV-related diseases including all stages of AIDS, as well as methods using these antibody compositions.

As used herein, an "antibody homolog" is a protein comprising one or more polypeptides selected from immunoglobulin light chains, immunoglobulin heavy chains, and antigen-binding fragments thereof, which have the binding and neutralization properties listed above. Antibody homologs include intact immunoglobulins of types IgA, IgG, IgE, IgD, IgM (as well as subtypes thereof), with kappa or lambda light chains. Fragments of the antibodies or their homologs with the above listed characteristics, for example, Fab fragments, Fab' fragments, $F(ab')_2$ fragments, F(v) fragments, heavy chain monomers or dimers, light chain monomers or dimers, dimers consisting of one heavy and one light chain, or the like are included within the scope of the present invention. Antibody homologs also include humanized recombinant antibodies and chimeric antibodies. Throughout the specification, the use of the term "antibodies of the present invention" and the like includes their homologs.

As used herein, the "CD4 positive cell surface antigen complex" or "cell surface antigen complex comprising CD4" is a binding site for the antibodies of the present invention. The complex may comprise CD4 in association with domains of chemokine receptors, e.g., CC-CKR5.

As used herein, a "humanized recombinant antibody" is an antibody initially derived from a nonhuman mammal in which recombinant technology has been used to replace some or all of the amino acids not used for binding to the CD4 cell surface complex on CD4-expressing cells with amino acids from corresponding regions of a human immunoglobulin light or heavy chain.

As used herein, a "chimeric recombinant antibody" is an antibody derived initially from a nonhuman mammal, in which recombinant DNA technology has been used to replace all or part of the hinge and constant regions of the light chain, the heavy chain or both, with corresponding regions from an immunoglobulin light chain or heavy chain of a mammal of a different species, preferably a human.

As used herein, "Leu3A" is the anti-CD4 murine monoclonal antibody commercially available in an FITC-conjugated form from Becton Dickinson Immunocytometry Systems, San Jose, Calif., under catalog number 340133.

As used herein, "OKT4A" is the anti-CD4 mouse monoclonal antibody commercially available in an FITC-conjugated form from Ortho Diagnostic Systems, Raritan, N.J. under catalog number OK704010.

As used herein, 5A8 is the anti-CD4 mouse monoclonal antibody described in PCT WO 92/09305.

As used herein, a "B4-mimetic agent" is a compound that causes at least a 30% reduction in the binding of monoclonal antibody B4 either to human recombinant soluble CD4 (rsCD4) or to human cell-surface CD4 antigen complex on CD4-expressing cells.

Antibodies According To This Invention

The antibodies or antibody homologs of the present invention bind specifically to a host cell antigen complex comprising CD4. The complex may comprise CD4 in association with domains of chemokine receptors such as CC-CCKR5. This is shown by their binding to CD4-expressing cells in a characteristic "caps" pattern in an indirect immunofluorescence assay as viewed by high resolution fluorescence microscopy.

The antibodies of this invention bind specifically to scattered discontinuous epitopes on a host cell antigen complex comprising CD4. The complex may comprise CD4 in association with domains of chemokine receptors such as the CC-CCKR5 molecule, block binding of HIV gp120 to the CD4 expressing cells, bind to the host cell antigen complex comprising CD4 following prior binding by HIV gp120, and inhibit infection of CD4 expressing cells by diverse primary isolates of HIV.

Preferred are those which block binding of HIV gp120 to surface CD4, and inhibit infection of CD4 cells by all primary isolates of HIV types 1 and 2 by both pre- and post-viral binding modalities.

The most preferred antibodies according to the present invention include the mouse monoclonal antibodies designated B4 (IgG 2a), M2 (IgG1) and B13 (IgG2a), described below.

The antibodies and their homologs of this invention are prophylactic and therapeutic for HIV infection and all stages of AIDS because they prevent replicative infection of host cells both before and after HIV gp120 has bound to a host cell antigen complex comprising CD4 on the surface of CD4 positive lymphocytes, thus they are capable of preventing HIV infection and retarding spread of the virus to uninfected cells. The antibodies and antibody homologs of this invention are uniquely useful because they inhibit infection following binding of HIV to CD4-expressing cells.

Screening Assays For Antibodies of the Present Invention

The ordinary skilled artisan may easily determine, using well known methods, whether particular antibodies or their homologs have the characteristics described above to identify antibodies or their homologs according to the present invention.

To determine whether particular antibodies bind to human CD4, any conventional binding assay employing the rsCD4 protein as the solid phase antigen may be used. Useful rsCD4 binding assays can be conveniently accomplished by ELISA formats and the like, through the use of an enzyme labelled secondary antibody specific for immunoglobulins of species from which the antibody homolog was derived.

The binding of antibodies or their homologs to a host cell antigen complex comprising CD4 on human CD4 expressing cells can be detected either by staining the cells with a fluorescently labelled secondary antibody specific for immunoglobulins of the same species from which the antibody or its homolog being tested is derived or by ELISA formats employing the rsCD4 protein in combination with peptides, e.g. peptide 2047, from chemokine receptors. A fluorescence activated cell sorter ("FACS") or a high resolution fluorescence microscope is used for determination of the percentage of antibody reactive cells and for scoring the intensity. The antibody binding to the cells can be observed by high resolution fluorescence microscopy to show characteristic "cap" "patches" and "caps and patches" pattern. The CD4-expressing cells useful for this purpose are CD4-expressing T lymphocytes, such as human peripheral blood T cells, thymocytes, and splenocytes or a CD4-expressing leukemia T cell line such as HPB-ALL or SUP-T. The cells are separated out by well-known methods. For example, normal T lymphocytes can be separated out by Ficoll-Hypaque centrifugation and malignant T cells can be separated out by centrifugation.

To determine whether a particular antibody blocks binding of HIV gp120 to human CD4, any suitable competition assay may be used. Useful assays include, for example, ELISA, indirect immunofluorescence assays, and the like. Preferably, the ability of labelled HIV gp120 to bind CD4 on CD4-expressing cells by prior incubation of the cells with the antibody is measured.

The ability of HIV gp120 to block the binding of a CD4 reactive monoclonal antibody to the CD4-expressing cell is evaluated by preincubating HIV gp120 with CD4-expressing cells, and quantifying the degree to which the pre-bound HIV gp120 inhibits binding of the antibody to the cells. Binding of the antibody to the CD4-expressing cells is quantified by FACS analysis or high resolution fluorescence microscopy, using a fluorescently labelled secondary antibody specific against the species from which the antibody being tested is derived.

The HIV gp120 used in the above assays may be provided by cells infected with HIV, by HIV itself, by host cells transformed with the gene for HIV gp120, by host cells infected with recombinant virus that express gp120, or by isolated gp120. Recombinantly produced HIV gp120 is preferred. Such a product is commercially available as a purified, recombinant HIV gp120 (American Biotechnologies, Inc., Cambridge, Mass.).

To evaluate the ability of a particular antibody to block HIV-induced syncytia formation among CD4-expressing cells, any known syncytia assay may be used. Preferably, a primary isolate or HIV-infected CD4-expressing tissue culture cells (e.g., H9) are added to cultures of MT-2 cells. Varying amounts of the antibodies are then added. Negative controls are supplemented with regular culture medium, or with an irrelevant antibody in the presence of HIV. A positive control with giant syncytia inducing strains may also be used. After incubation, all of the cultures are scored by visual quantification of syncytia or plaque formation, in the case of giant syncytia inducing strains. In this way, the ability of an antibody to block syncytia formation or to reduce the number of plaques formed in a culture is scored.

To determine whether a particular antibody inhibits infection of CD4-expressing cells by HIV, any indication of HIV infection could be monitored. Useful in vitro indicators of HIV infection include, for example, secretion of HIV core antigen p24. Preferably, inhibition of HIV infection is determined by comparing HIV p24 levels in the presence and absence of the antibody in HIV-infected CD4-expressing cell cultures.

To evaluate the ability of a particular antibody to block HIV infection of CD4-expressing cells, a quantitative p24 viral antigen assay may be used. Preferred is a p24 antigen neutralization assay for the determination of neutralization activity of antibody at the indicated dilutions against input virus (Wrin et al., *J Virol,* 1995, 69:39–48). In this p24 HIV viral assay, virus infectivity and neutralization is quantitated by determining p24 antigen accumulated by the PBMC cultures by p24 ELISA (Coulter Immunology, Hialeah, Fla.).

To determine whether a particular antibody has an enhanced binding property to a host cell antigen complex comprising CD4 over the binding to a rsCD4 molecule, ELISA or the like are useful. In such assays, the ability of the antibody to bind to the CD4-comprising antigen complex may be detected through the use of a labeled secondary antibody specific for immunoglobulins of the species from which the antibody was derived employing the rsCD4 which had been preincubated with a peptide derived from a domain of a receptor suspected to be in association with CD4. The peptide are selected from the peptides from domain 3 of IL8R, (p2029a), domains 2 and 3 of CC-CKR2b (p2087a, p2088a), domains 1 and 4 of CC-CKR3 (p2079a and 2082a) and domain 3 of CC-CKR5 (p2047a).

To determine whether a particular antibody binds to a human CD4-derived peptide, ELISA or the like are useful. In such assays, the ability of the antibody to bind to these peptides may be detected through the use of a labeled secondary antibody specific for immunoglobulins of the species from which the antibody was derived.

To determine whether a particular antibody binds to a human chemokine receptor-derived peptide, ELISA or the like are useful. In such assays, the ability of the antibody to bind to these peptides may be detected through the use of a labeled secondary antibody specific for immunoglobulins of the species from which the antibody was derived.

Preferably, the binding of an antibody to a peptide is determined through inhibition studies in a rsCD4 ELISA by first incubating the rsCD4 reactive antibody with the CD4 peptides listed above or in Table 1, followed by a second incubation of the antibody-peptide complex with the rsCD4-coated or rsCD4/chemokine receptor peptide-coated microwells.

Types Of Antibody Homologs Of This Invention And Their Production

Antibodies of the present invention include both antibodies and antibody homologs which display the novel combination of properties of B4, described above, as characterized by the procedures described above and in Examples 2–18. Antibodies of this invention may be intact monoclonal antibodies, intact recombinant antibodies, intact chimeric recombinant antibodies, intact humanized recombinant antibodies, or antigen binding portions thereof that display the binding and neutralizing properties of B4, M2 and B13.

A. Monoclonal Antibodies

The most preferred antibody type of the present invention are intact monoclonal antibodies produced by hybridomas of the present invention. The technology for producing monoclonal antibodies is well known (See generally, Kennett et al., "Methods for Production and Characterization of Monoclonal Antibodies", in *Monoclonal Antibodies, Hybridomas: A new Dimension in Biological Analyses,* Plenum Press, pp 363–419, 1980).

Useful CD4-comprising host cell antigen complex preparations for the elicitation of antibodies of the invention include human CD4-expressing cells, e.g., CD4-expressing peripheral blood lymphocytes, thymocytes or cells from CD4-expressing human T cell lines.

This is contrary to the teachings of Kung et al., U.S. Pat. No. 4,381,295, which stated: "In fact, the present applicants have discovered that using a T cell malignant cell line as the antigen caused formation of hybridomas which did not produce the desired [T4] antibody." (Column 4, lines 54–56). Indeed, Kung et al. reported no reactivity of OKT4 observed with 8 out of 8 cases of T-acute lymphatic leukemia (Column 14, line 45) and most of T cell lines (line 51), and thus concluded that malignant T cell lines were undesirable immunogens.

The immunogen for generating the antibody of the present invention is from a reliable source of CD4-expressing cells, preferably, from a T cell line such as HPB-ALL which is derived from a patient with T-acute lymphoblastic leukemia (T-ALL) or SUP-T1 which is derived from a patient with T-cell non-Hodgkin's lymphoma (T-NHL).

While not wishing to be bound by theory, it is believed that using CD4-expressing cells such as HPB-ALL, SUP-T cells or MT-2 as the immunogen, rather than isolated CD4 or recombinant soluble forms of CD4 (e.g., rsCD4), evokes the generation of antibodies of the present invention. The use of CD4-expressing cells provides the more favorable conformation on the surface of cells for the CD4 comprising host cell antigen complex which cannot be provided by the CD4 molecule alone.

Immunization may be accomplished using standard procedures. The unit dose and immunization regimen depend on the species of mammal immunized, its immune status, the body weight of the mammal, and the amount of the CD4 comprising host cell antigen complex in the preparation administered.

In the preferred embodiment, each dose of the CD4-expressing cell preparation used for immunization of mice contains at least about $5-10 \times 10^6$ cells. Typically, the mouse is immunized intraperitoneally on day 0 with the CD4-expressing T cells, thoroughly washed in PBS to be free from any culture medium proteins, with or without adjuvant. The mouse is then given a first boost intraperitoneally with the CD4-expressing T cells washed and resuspended in PBS 14 days to 6 months after the initial immunization, and preferably 15 to 30 days after the first immunization, in the absence of any adjuvant. Additional boosts may be administered. Hyperimmunization with multiple boosts without adjuvant is preferred.

Three days before fusion, the final boost (CD4-expressing T cells in PBS without adjuvant) is administered intravenously. The sera of the immunized mammal is screened in accordance with the strategy described above and more specifically in Table 12 for the presence of antibodies of the invention. The splenocytes are isolated from immunized mammals whose sera are reactive with rsCD4. Any of the many well known protocols useful for fusing splenocytes and immortalized cell lines are then used for the purpose of generating hybridomas of this invention.

Typically, the immortal cell line (e.g., a myeloma cell line) and the splenocytes are derived from the same mammalian species. Useful mammals include mice, rats and rhesus monkeys. Preferably, the splenocytes are derived from an inbred mouse of strain BALB/c or an outbred mouse of CD1 strain (Jackson Labs, Bar Harbour, Me.). Preferred immortal cell lines are mouse myeloma cell lines that are sensitive to culture medium containing hypoxanthine, aminopterin and thymidine ("HAT medium"). The most preferred mouse myeloma cell line is P3x63-AG8.653 (ATCC, Rockville, Md., catalog no. CRL 1580). Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells, while unfused splenocytes die naturally after several days.

Hybridoma cells producing an antibody according to the present invention are detected by screening the hybridoma culture supernatants using the screening assays described above. Preferably, the primary screen will select antibodies that have a "preferential" binding activity to rsCD4 which had been preincubated with a peptide (e.g. p2047) derived from the third external domain of the chemokine receptor CC-CKR5 over its binding activity to rsCD4 alone. The enhanced binding is detected by comparing the ELISA results obtained by the corresponding rsCD4/p2047 complex vs. rsCD4. This simple dual primary screen (rsCD4/p2047 vs. rsCD4) will eliminate a majority (>90%) of antibodies having reactivities to non-CD4 comprising surface antigens. Antibodies selected for their preferential reactivities to rsCD4 in association with the third external domain of the CC-CKR5 molecule over rsCD4 are subjected to a secondary screening for binding to the cell surface antigen complex comprising CD4 by characterization of their binding to CD4-expressing cells, for example, the HPB-ALL or SUP-T cells. Such binding is detected by fluorescently labelled secondary antibodies specific for immunoglobulins of the species from which the antibody was derived, and quantified by FACS analysis or by a fluorescence microscope and observed by fluorescence microscopy. Antibodies having binding reactivity to the CD4-expressing cells are further tested for their ability to neutralize primary isolates of HIV-1, for example 23135, by an MT-2 microplaque neutralization assay for the measurement of syncytia formation inhibition or a p24 antigen neutralization assay for the measurement of inhibition of viral replication.

Those clones secreting antibodies exhibiting preferential binding to rsCD4/p2047 and/or binding activity to rsCD4 by ELISAs, that brightly stain for CD4-expressing cells by an indirect immunofluorescence assay, and which display neutralizing activities against primary isolate of HIV at a concentration of <10 $\mu$g/mL are selected for final cloning and subcloning.

To produce antibodies of this invention which are intact monoclonal antibodies, hybridomas tested positive in the above screening assays are cultured in a nutrient medium under well known conditions and for a time sufficient to allow the hybridoma cells to secrete the monoclonal antibodies into the culture medium. Tissue culture techniques and culture media suitable for hybridoma cells are well known (See, for example, Kennett et al., *Monoclonal Antibodies*, supra). Conditioned hybridoma culture supernatants containing the desired antibodies are collected.

Alternatively, the desired antibody may be produced by injecting the selected hybridoma cells into the peritoneal cavity of an unimmunized mouse. The hybridoma cells proliferate in the peritoneal cavity, secreting the antibody, which accumulates as ascites fluid (Kennett et al., *Monoclonal Antibodies*, supra). The antibody is harvested by withdrawing the ascites fluid from the peritoneal cavity with a syringe.

It will be understood by the ordinary skilled artisan that monoclonal antibodies according to this invention may be purified with ease from conditioned hybridoma culture supernatant or from ascites fluid.

B. Recombinant Antibodies And DNA Encoding Them

Antibody homologs according to the present invention may be recombinant monoclonal antibodies produced by host cells transformed with DNA encoding immunoglobulin light and heavy chains according to this invention. Recombinant antibodies may be produced by well known genetic engineering techniques.

For example, recombinant antibodies may be produced by cloning cDNA or genomic DNA encoding the immunoglobulin light and heavy chains of the desired antibody from a hybridoma producing an antibody according to this invention. The cDNA or genomic DNA encoding those polypeptides is then inserted into recombinant expression vectors so that both genes are operatively linked to their own regulatory sequences, for control of transcription and translation. The expression vector and the regulatory sequences for control of expression are chosen to be compatible for expression in the selected host cell. Typically, both the heavy and light chain genes are inserted into the same expression vector so that expression of both is operatively linked.

Prokaryotic or eukaryotic cells may be used as expression hosts. Expression in eukaryotic host cells is preferred because such cells are more likely than prokaryotic cells to assemble and secrete a properly folded and immunologically active antibody.

It will be understood that variations on the above procedure are within the scope of the present invention.

It is possible that the host cells will produce portions of intact antibodies, such as light chain dimers or heavy chain dimers, which also are antibody homologs according to the present invention. For example, it may be desired to transform a host cell with DNA encoding either the light chain or the heavy chain (but not both) of an antibody of this invention. Recombinant DNA technology may also be used to remove some or all of the DNA encoding either or both of the light and heavy chains that is not necessary for CD4 binding, e.g., DNA encoding Fab' fragments. The molecules expressed from such truncated DNA molecules are antibody homologs according to this invention.

C. Chimeric And Humanized Recombinant Antibodies And DNA Encoding Them

DNA encoding the recombinant antibodies described above may be used as the starting point for producing chimeric or humanized recombinant antibodies. Chimeric recombinant antibodies are produced by transforming a host cell with a suitable expression vector comprising DNA encoding the desired immunoglobulin light and heavy chains in which all or some of the DNA encoding the hinge and constant regions of the heavy and/or the light chain have been substituted with DNA from the corresponding region of an immunoglobulin light or heavy chain of a different species. When the original recombinant antibody is nonhuman, substitution with human sequences encoding hinge and constant regions is preferred. An exemplary chimeric recombinant antibody has mouse variable regions and human hinge and constant regions. See generally, U.S. Pat. No. 4,816,397 and Morrison et al., "Chimeric Human Antibody Molecules: Mouse Antigen-Binding Domains With Human Constant Region Domains", *Proc Nat'l Acad Sci USA*, 1984, 81:6851–55.

Humanized recombinant antibodies are produced by transforming a host cell with a suitable expression vector comprising DNA encoding the desired nonhuman immunoglobulin light and heavy chains in which all or some of the DNA encoding amino acids not involved in CD4 antigen complex binding, including framework sequences interspersed among the complementarity determining regions (CDRs), have been substituted with DNA from the corresponding regions of a desired human immunoglobulin light or heavy chain. See generally, P. T. Jones et al. "Replacing The Complementarity-Determining Regions In A Human Antibody With Those From A Mouse", *Nature*, 1986, 321:522–25.

The most preferred humanized recombinant antibodies of this invention have the B4 "CDRs" interspersed among human framework sequences.

D. Antibody Homologs According To This Invention that are Generated in Transgenic Mammals Hybridomas from mice homozygous for an inactivated endogenous immunoglobulin locus and containing transgene sequences encoding a human sequence heavy chain and human sequence light chain, secrete antibody homologs comprising a human sequence heavy chain and a human sequence light chain. These transgenic antibody homologs, that bind to the recombinant soluble CD4 molecule and more preferentially to rsCD4 in association with a peptide (e.g. p2047) derived from the third external domain of the CC-CKR5 chemokine receptor by the respective ELISAs, and to a human host cell antigen complex comprising the CD4 protein by indirect immunofluorescence staining of CD4-expressing cells, that have a neutralizing activity directed against primary isolates from all clades of HIV-1, and diverse primary isolates of HIV-2 and SIV, and have similar antibody binding properties to that of monoclonal antibody B4, can be generated by immunization and screening schemes like that described in section A, subtitled Monoclonal Antibodies.

More specifically, a transgenic mouse characterized either as having HC1 or HC2 genotype as described in Smith et al., WO 93/12227, homozygous for a functionally disrupted $J_H$ locus and harboring a transgene capable of rearranging to encode a human sequence heavy chain and a transgene capable of rearranging to encode a human sequence light chain is used as the host for immunization instead of normal BALB/c or CD1 mouse.

E. Antibody Homologs According To This Invention That Are Not Intact Antibodies

Homologs also includes fragments of the antibodies of the present invention. Such fragments may be derived from any of the intact antibodies described above. For example, host cell antigen complex-binding fragments, as well as full-length monomeric or dimeric polypeptides derived from the above-described antibodies are themselves antibody homologs according to the present invention. Useful antibody homologs of this type include Fab fragments, Fab' fragments, $F(ab')_2$ fragments, F(v) fragments, heavy chain monomers or dimers, light chain monomers or dimers, dimers consisting of one heavy and one light chain, and the like. The foregoing fragments generally are useful antibody homologs according to the present invention.

Antibody fragments may be produced by chemical methods, e. g., by cleaving an intact antibody. with a protease, such as pepsin or papain, and optionally treating the cleaved product with a reducing agent. Alternatively, useful fragments may be produced by using host cells transformed with truncated heavy and/or light chain genes or fusions of truncated heavy and light chain genes. Heavy and light chain monomers may be produced by treating an intact antibody with a reducing agent, such as dithiothreitol, followed by purification to separate the chains. Heavy and light chain monomers may also be produced by host cells transformed with DNA encoding either the desired heavy chain or light chain, but not both. (See, Sastry et al., *Proc Nat'l Acad Sci USA,* 1989, 86:5728–32).

Cells That Produce Antibodies Of The Present Invention The present invention also provides cells and cell cultures that produce the antibodies of this invention. Such cells include hybridomas that produce monoclonal antibodies of this invention.

Moreover, the present invention provides a method of producing the antibodies of the present invention by culturing the cells which produce the antibodies. Methods of culturing such cells and isolating the antibodies produced are well known. These methods include cell culture techniques, as well the generation of ascites.

Also provided is a method for producing hybridomas of this invention comprising the step of immunizing a nonhuman mammal with CD4-expressing cells.

The cells to be used as an immunogen for this process are the cells from a reliable source of CD4-expressing cell line, for example, a human leukemia or lymphoma derived T cell line such as HPB-ALL derived from a patient with T-acute lymphoblastic leukemia (T-ALL) or SUP-T derived from a patient with T-cell non-Hodgkin's lymphoma (T-NHL) that is delivered intraperitoneally in PBS, or complete Freund's adjuvant for the first immunization, and administered free of any adjuvant, either intraperitoneally or intravenously for subsequent boosts.

Pharmaceutical Compositions And Methods Of This Invention

The antibody and homologs thereof of this invention are useful in prophylactic and therapeutic compositions for preventing diseases caused by infective agents whose primary targets are CD4-expressing lymphocytes. Such diseases include HIV infection and associated diseases including AIDS.

Preferred pharmaceutical compositions of this invention for administration to humans include the antibodies of the present invention, such as one or more of the mouse monoclonal antibodies B4 or M2 or B13 and homologs thereof, such as mouse/human chimeric recombinant antibodies, humanized recombinant antibodies or antigen-binding portions of those antibodies. Pharmaceutical compositions comprising mouse/human chimeric recombinant antibodies with similar binding properties exhibited by B4 or M2 or B13 or humanized recombinant antibodies with similar binding properties exhibited by B4 or M2 or B13 are most preferred.

The pharmaceutical compositions of this invention may further comprise other therapeutics for the prophylaxis of HIV infection. For example, the antibody homologs of this invention may be used in combination with antiretroviral agents that block reverse transcriptase, such as AZT, or with agents that inhibit the HIV protease. Additionally, the pharmaceutical compositions of this invention may further comprise anti-viral agents such as interferons, or immunosuppressive agents such as cyclosporin.

Furthermore, one or more antibody homologs may be used in combination with two or more of the foregoing therapeutic agents. Such combination therapies may advantageously utilize lower dosages of the administered therapeutic agents, thus avoiding possible toxicities or adverse effects associated with the various monotherapies.

The pharmaceutical compositions of this invention comprise an immunotherapeutically effective amount of one or more antibody homologs according to this invention, or derivatized form(s) thereof and, preferably, a pharmaceutically acceptable carrier. By "immunotherapeutically effective amount" is meant an amount capable of preventing the immunocompromising effects of HIV infection or AIDS, or of other diseases caused by infective agents whose primary targets are CD4-expressing lymphocytes. By "pharmaceutically acceptable carrier" is meant a carrier that does not cause an allergic reaction or other untoward effect in patients to whom it is administered.

Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the antibody homolog.

The compositions of this invention may be in a variety of forms. These include, for example, solid, semi-solid and liquid dosage forms, such as tablets, pills, powders, liquid solutions, dispersions or suspensions, liposomes, suppositories, injectable and infusible solutions. The preferred form depends on the intended mode of administration and prophylactic or therapeutic application. The preferred compositions are in the form of injectable or infusible solutions.

The preferred pharmaceutical compositions of this invention are similar to those used for passive immunization of humans with other antibodies. The preferred mode of administration is parenteral.

It will be apparent to those of skill in the art that the immunotherapeutically effective amount of antibody homolog of this invention will depend upon the administration schedule, the unit dose of antibody homolog administered, whether the antibody homolog is administered in combination with other therapeutic agents, the immune status and health of the patient, and the antiviral activity of the particular antibody homolog administered.

Immunotherapy for prophylaxis of HIV infection, i.e., immunotherapeutically effective amounts per unit dose of an antibody homolog which is an intact antibody, range from about 1 to 100 mg/kg patient weight, preferably, 5 mg/kg to 50 mg/kg patient weight, and most preferably 5 mg/kg patient weight. Unit doses should be administered once every two weeks, and preferably once immediately after an accidental exposure such as needlestick. The antiviral effect may be measured by a variety of methods, including viral load. It will be recognized, however, that lower or higher dosages and other administration schedules may be employed.

Treatment regimens for antibody homologs that are not intact antibodies may differ, depending on their size and pharmaceutical properties.

In order that this invention may be better understood, the following examples are set forth. These examples are for purposes of illustration only, and are not to be construed as limiting the scope of the invention in any manner.

EXAMPLE 1

Comparison of the Susceptibility of Laboratory Strains and Primary HIV-1 Isolates to In Vitro Neutralization by Antibodies Directed Against HIV-1 gp120

Specific procedures for the determination of virus neutralization by antibody.

Cells

Human T cell line MT-2 (No. 237, NIH AIDS Research and Reference Reagent Program Catalog) was maintained in Dulbecco's modified Eagle medium supplemented with 15% fetal bovine serum as previously described (Hanson et al., *J Clin Microbiol*, 1990, 28:2030–2034). Peripheral blood mononuclear cells (PBMCs) of HIV-1 seronegative donors were isolated from fresh buffy coat units by Ficoll-Hypaque gradient separation (Organon Teknika Corp., Durham, N.C.). The resulting PBMCs were stimulated with 0.5% PHA-P (Difco Laboratories, Detroit, Mich.). After 3 to 4 days, the PHA-P-containing medium was removed and the cells maintained in RPMI with 15% fetal bovine serum, 900 µg/mL glutamine, antibiotics, and 5% interleukin-2 (Cellular Products, Inc., Buffalo, N.Y.).

Viruses

HIV-1 MN is a laboratory-adapted strain available as and maintained as a persistently infected H9 cell culture from the National Institutes of Health, Bethesda Md. (NIH AIDS Research and Reference Reagent Program Catalog no. 402), from which were prepared cell-free concentrated stocks. Primary isolates of HIV-1 were prepared from patient PBMCs by PBMC cocultivation. Stock cultures of primary isolates were prepared by no more than 3–5 passages through PBMCs, and clarified by centrifugation (Sawyer et al., *J Virol*, 1994, 68:1342– 1349). They were supplied by Carl Hanson of the California Department of Health Services, Berkeley Calif.

MT-2 Microplaque Neutralization Assay

The determination of HIV-neutralizing antibody titer employs the preincubation of serially diluted sera or antibody with a fixed amount of HIV followed by infection of HIV-sensitive MT-2 cells and formation of a cell monolayer displaying HIV-induced microplaques. Results are scored by quantitation of the microplaques. The assay is suitable for SI isolates only, whether laboratory-adapted or primary isolates, because the microplaques represent giant syncytia formed by MT-2 cells fusing to foci of HIV-infected cells; and, the assay is appropriate for evaluating inhibition of both virus to cell and cell to cell transmission because inhibition of syncytia formation results from the action of antibody on either HIV particles or HIV-infected cells, i.e., the assay measures both the inhibition of virus to cell HIV-induced fusion or cell to cell HIV-induced fusion. Neutralization is then observed by reduction of microplaques as observed by enumeration of propidium iodide-stained plaques 1 week later (See, Hanson et al., *J Clin Microbiol*, 1990, 28:2030–2034). In this assay, both virus and serum or antibody are diluted in 50% pooled, defibrinated normal human plasma to negate any nonspecific enhancing or inhibitory effects.

Sera and Antibody

GP anti-gp120 N-terminal V3 MN is pooled sera from guinea pigs that had been hyperimmunized (Wang et al., *Science*, 1991, 254:285–288) with a synthetic peptide antigen corresponding to the N-terminal portion of the hypervariable V3 domain of gp120 from HIV-1 MN (anti-N-terminal V3 MN). GP anti-gp120 N-terminal V3 library sera is pooled antisera from three guinea pigs hyperimmunized with a complex mixture of peptides representing a library of approximately $1\times10^{13}$ possible HIV-1 N-terminal V3 sequences (anti-N-terminal V3 library). The N-terminal V3 MN and N-terminal V3 library immunogens used for the guinea pig immunizations were multibranched N-terminal V3 synthetic peptide immunogens that can be used to generate polyclonal antibody with neutralizing activity for several laboratory strains of HIV-1, as described in Walfield et al. (Koff et al., ed., AIDS Research Reviews, Chapter 18, Marcel Dekker: New York, 1993). Another anti-gp120 antibody is a recombinant human monoclonal antibody (MAb) designated IgG1 b12 with specificity for the gp120 binding site for CD4 (anti gp120 CD4-BS) (Burton et al., *Science*, 1994, 266:1024–1027). IgG1 b12 was generated as an Fab fragment from an antibody-phage display library prepared from bone marrow of a long-term asymptomatic HIV-1 seropositive donor and was converted to a whole human antibody by cloning into a recombinant DNA IgG1 expression vector. It is regarded as the golden standard of antibodies for neutralization of diverse HIV primary isolates (Burton et al., supra).

Results

A comparison of the HIV-1 neutralization activities of anti-N-terminal V3 MN guinea pig antiserum, anti-N-terminal V3 library guinea pig antisera, and IgG1 b12 (anti-gp120 CD4-BS), is shown in Table 2. Neutralization activities for the two anti-N-terminal V3 sera were determined on the HIV-1 MN laboratory strain and on two HIV-1 primary isolates (23135 and BR014). Neutralization activity was determined for the anti-gp120 CD4 binding site antibody on the two primary isolates, 23135 and BR014. Neutralization activities were determined by the MT-2 Microplaque Neutralization Assay and are expressed in Table 2 at the indicated endpoints (50% and 90%) as dilution titers for the polyclonal serum antibodies and as concentrations (µg/mL) for the monoclonal antibody.

HIV-1 MN, the laboratory-adapted strain grown on T cell line H9, was quite sensitive to neutralization by both anti-N-terminal V3 antisera, with anti-N-terminal V3 MN being about four times more potent than the less strain-specific anti-N-terminal V3 library antisera. The PBMC-grown primary isolates were refractory to neutralization by either of the anti-N-terminal V3 sera. However, at least one of the primary isolates was moderately neutralizable by the anti-gp120 CD4 binding site, IgG1 b12. These results are reflective of the differences between laboratory-adapted HIV-1 and primary isolates in susceptibility to neutralization. They indicate the sensitivity of laboratory-adapted HIV-1 strains to strain-specific anti-gp120 N-terminal V3 antibodies, the resistance of primary isolates to such antibodies, and the sensitivity of some primary isolates to neutralization by antibodies directed against the binding of gp120 to the host cell CD4 receptor.

TABLE 2

Neutralization Activities of Anti-gp120 Antibodies Against HIV-1 Laboratory Strain and HIV-1 Primary Isolates (MT-2 Microplaque Neutralization Assay)

| | HIV Strain | | | |
|---|---|---|---|---|
| | Laboratory Strain | | Primary Field Isolate | |
| | MN | | 23135 | BR014 |
| Specimen | 50% Inhbt. | 90% Inhbt. | 50% Inhbt. | 50% Inhbt. |
| GP α gp120 N-terminal V3 MN [G.P. No. 4276–4280; 12 wpi*] | 1:203,080 | 1:39,840 | <1:10 | <1:10 |
| GP α gp120 N-terminal V3 library [.P. No. 6546, 6547; 8 wpi*] | 1:23,968 | 1:6,182 | <1:10 | <1:10 |
| MAb IgG1 b12 (α gp120) | — | — | 12.8 µg/mL | >50 µg/mL |

*wpi: weeks post initial immunization

EXAMPLE 2

Characterization of the In Vitro Neutralizing Activities of Anti-Host Cell Antibodies Against Primary HIV-1 Isolates The monoclonal antibodies were purified from ascites fluids and the guinea pig polyclonal anti-gp120 N-terminal V3 antibodies were purified from serum by Protein A affinity chromatography. The antibodies were reconstituted as sterile solutions in Phosphate-Buffered-Saline (PBS) at 1 mg/mL and were prepared as serial dilutions in PBS for HIV-1 neutralization assays. Antibodies were assayed individually and were combined into the mixtures of groups 7–15 so as to show synergistic interactions between antibodies of different specificities or lack thereof. Neutralization activities against HIV-1 were determined on two primary isolates by the MT-2 Microplaque Neutralization Assay and are expressed at the indicated endpoints (50% and 90%) as antibody concentrations (μg/mL).

Results

The results presented in Table 3 show the neutralization activities against two clade B HIV-1 primary field isolates (23135 and BRO14) of a collection of antibodies including murine monoclonal antibodies with specificities for various cell surface antigens (groups 1 and 2, MAbs ID1 and 80A for HLA DR; group 3, MAb A1.4 for HLA A,B,C heavy chain; group 4, MAb H28 for $\beta_2$-microglobulin; and group 5, B4 for a host cell antigen complex comprising the CD4 protein), a polyclonal anti-gp120 N-terminal V3 MN antibody preparation from a guinea pig immunized with a synthetic peptide taken from the N-terminal V3 domain of gp120 from HIV-1 MN (group 6), mixtures of these antibodies (groups 7–15), and five additional monoclonal antibodies directed against well-characterized T cell antigens (group 16, MAb for E rosette receptor; group 17, MAb for T3 antigen; group 18, MAb for Leu1; group 19, MAb for T8 antigen; and, group 20, MAb C37 for T-cell antigen receptor)(Wang et al., *Hybridoma* 1986, 5:179–190).

Of the 11 individual antibodies tested in the experiment of Table 3, only a MAb derived from mouse immunized with T cell line HPB-ALL, B4 (group 5), which is a preferred embodiment of the present invention with a unique binding activity toward a host cell receptor antigen complex comprising CD4, demonstrated strong neutralization of the primary isolates. The mixtures of antibody groups 7–15 displayed neutralizing activities only if they included B4. Compare results for groups 7–10 and 15 to groups 11–14. Furthermore, comparison of the neutralizing activities of group 5, groups 9, 10, 15 and groups 7 and 8 show that the neutralizing activity of the mixtures is contributed only by B4. The other antibodies serve only to dilute the neutralizing activity of B4 and there is no evidence of any synergistic interaction between the antibody directed against host cell antigen complex comprising CD4 of the invention (MAb B4) and the other anti-cellular antibodies or the anti-gp120 N-terminal V3 antibody. None of the monoclonal antibodies directed against other T cell antigens, known to be expressed on the HPB-ALL cells, neutralized HIV-1 primary isolates to any detectable level.

TABLE 3

Neutralization of HIV-1 B Clade Primary Field Isolates by Monoclonal Antibodies Directed Against Host Cell Antigens (MT-2 Microplaque Neutralization Assay)

| | | HIV Strain | | | |
|---|---|---|---|---|---|
| | | 23135 | | BR014 | |
| Group | Type of Antibodies | 50% Inhbt. | 90% Inhbt. | 50% Inhbt. | 90% Inhbt. |
| 1 | MAb α HLA DR(ID1) | >100 μg/mL | >100 μg/mL | 71.4 μg/mL | >100 μg/mL |
| 2 | MAb α HLA DR (80A) | >100 μg/mL | >100 μg/mL | >100 μg/mL | >100 μg/mL |
| 3 | MAb α HLA A,B,C Heavy chain (A1.4) | >100 μg/mL | >100 μg/mL | 47.6 μg/mL | >100 μg/mL |
| 4 | MAb α $\beta_2$ microglobulin (H28) | >100 μg/mL | >100 μg/mL | >100 μg/mL | >100 μg/mL |
| 5 | MAb B4 (α HPB-ALL) | 0.21 μg/mL | 1.54 μg/mL | 0.19 μg/mL | 1.63 μg/mL |
| 6 | Polyclonal IgG α N-terminal V3 MN | >100 μg/mL | >100 μg/mL | >100 μg/mL | >100 μg/mL |
| 7 | Ab mixture gps 1 + 2 + 3 + 4 + 5 [eq. ratio] | 1.05 μg/mL | 4.37 μg/mL | 0.75 μg/mL | 4.13 μg/mL |
| 8 | Ab mixture gps 1 + 2 + 3 + 4 + 5 + 6 [eq. ratio] | 1.17 μg/mL | 5.75 μg/mL | 1.17 μg/mL | 8.08 μg/mL |
| 9 | Ab mixture gps 1 + 5 [eq. ratio] | 0.51 μg/mL | 0.96 μg/mL | 0.49 μg/mL | 2.52 μg/mL |
| 10 | Ab mixture gps 1 + 5 + 6 [eq. ratio] | 0.60 μg/mL | 3.51 μg/mL | 0.75 μg/mL | 3.32 μg/mL |
| 11 | Ab mixture gps 1 + 6 [eq. ratio] | >100 μg/mL | >100 μg/mL | >100 μg/mL | >100 μg/mL |
| 12 | Ab mixture gps 2 + 6 [eq. ratio] | >100 μg/mL | >100 μg/mL | >100 μg/mL | >100 μg/mL |
| 13 | Ab mixture gps 3 + 6 [eq. ratio] | >100 μg/mL | >100 μg/mL | >100 μg/mL | >100 μg/mL |
| 14 | Ab mixture gps 4 + 6 [eq. ratio] | >100 μg/mL | >100 μg/mL | >100 μg/mL | >100 μg/mL |
| 15 | Ab mixture (Fr. gps 5 + 6 [eq. ratio) | 0.46 μg/mL | 2.52 μg/mL | 0.67 μg/mL | 3.14 μg/mL |
| 16 | MAb α E rosette receptor | >50 μg/mL | >50 μg/mL | >50 μg/mL | >50 μg/mL |
| 17 | MAb α T3 | >50 μg/mL | >50 μg/mL | >50 μg/mL | >50 μg/mL |
| 18 | MAb α Leu1 | >50 μg/mL | >50 μg/mL | >50 μg/mL | >50 μg/mL |
| 19 | MAb α T8 | >50 μg/mL | >50 μg/mL | >50 μg/mL | >50 μg/mL |
| 20 | MAb α T cell antigen receptor (C37) | >50 μg/mL | >50 μg/mL | >50 μg/mL | >50 μg/mL |

EXAMPLE 3

Monoclonal Antibodies Directed Against a Host Cell Antigen Complex Comprising CD4 Developed Through Immunization of BALB/c Mice with HPB-ALL Cells Specific Procedures for the determination of monoclonal antibody reactivities with rsCD4, and with CD4-expressing cells rsCD4

Purified recombinant soluble CD4 (rsCD4) was obtained from a commercial source (American Bio-Technologies, Inc. Cambridge, Mass.) and from NIH (USA) AIDS Research and Reference Reagent Program.

Determination of anti-CD4 reactivity by rsCD4 ELISA rsCD4 ELISA were conducted by coating 96-well microtiter plates by overnight incubation at 4° C. with rsCD4 at 0.25 μg/mL using 100 μL per well in 10 mM NaHCO₃ buffer, pH 9.5. The rsCD4 coated wells were incubated with 250 μL of 3% by weight of gelatin in PBS at 37° C. for 1 hr to block non-specific protein binding sites, washed three times with PBS containing 0.05% by volume TWEEN 20 and then dried. Test samples (monoclonal antibodies or a guinea pig anti-rsCD4 serum) were diluted with PBS containing 20% by volume normal goat serum, 1% by weight gelatin and 0.05% by volume TWEEN 20 at dilutions of 1:20 volume to volume unless indicated otherwise. 100 μL of the diluted sample was added to each of the wells and allowed to react for 1 hr at 37° C. The wells were then washed six times with 0.05% by volume TWEEN 20 in PBS to remove unbound labeled antibodies. 100 μL of horseradish peroxidase labeled goat anti-mouse IgG or goat anti-guinea pig IgG at a dilution of 1:1000 in 1% by volume normal goat serum, 0.05% by volume TWEEN 20 in PBS was added to each well and incubated at 37° C. for 15 minutes. The wells were washed six times with 0.05% by volume TWEEN 20 in PBS to remove unbound labeled antibody conjugate and reacted with 100 μL of the substrate mixture containing 0.04% by weight orthophenylenediamine (OPD) and 0.12% by volume hydrogen peroxide in sodium citrate buffer pH 5.0, for 15 minutes. Reactions were stopped by the addition of 100 μL of 1.0 M $H_2SO_4$ and the absorbance at 492 nm ($A_{492}$) was measured.

Determination of reactivity to CD4-expressing cells by indirect immunofluorescent staining $0.5 \times 10^6$ CD4-expressing cells (e.g. HPB-ALL or SUP-T1 cell line cells) per well were washed twice in PBS containing 1% BSA prior to their incubation with the designated monoclonal antibody or the guinea pig anti-rsCD4 serum for 45 minutes at room temperature. After incubation of the cells with the first staining antibody, the cells were washed for an additional two times in the same washing buffer and were incubated with a secondary Fluorescein isothiocyanate (FITC)-conjugated goat anti-mouse IgG or (FITC) -conjugated goat anti-guinea pig IgG reagent at a 1:500 dilution (Cappel, Malvern Pa.) for an additional 45 minutes at room temperature. The stained cells were washed again in the same washing buffer and the cells processed for fluorescence analysis by cytofluorograph and/or immunofluorescence microscopy for determination of percentage of stained cells, intensity of staining, and more preferably the antigen staining pattern by each of the antibodies.

Results

HPB-ALL cell line is a malignant human T cell line derived from a patient with acute lymphoblastic leukemia having the following membrane phenotype revealed by indirect immunofluorescence: CD5+(T1/Leu1+), CD4-expressing (T4/Leu3A+), CD8+(T8/Leu2/C8+), CD3+(T3/Leu4+), CD6+(T6/Leu6+), CD2+(T11/Leu5/D9+), CD25+ (Tac+), HLA-A,B,C and $\beta_2$microglobulin+, and HLA-DR- (Wang et al., 1986, supra). BALB/c mice were immunized intraperitoneally with $5–10 \times 10^6$ PBS-washed exponentially growing HPB-ALL cells in complete Freund's adjuvant for the initial immunization followed by weekly to biweekly intraperitoneal boosts with $5–10 \times 10^6$ PBS-washed exponentially growing cells suspended in PBS without any adjuvant for a total of three months. Splenectomy was performed 3 days after the final intravenous immunization with $5 \times 10^6$ PBS-washed HPB-ALL cells and a mononuclear cell suspension was prepared. The mononuclear splenocytes were treated with polyethylene glycol (PEG) for fusion to myeloma cells and somatic cell hybridization. Fusion cells were dispensed into the wells of 96-well microtiter plates, incubated, and wells that contained antibodies specific for rsCD4, as detected by the rsCD4 ELISA described above were selected. The rsCD4-reactive hybridomas were harvested and single-cell cloned by a limiting dilution method in the presence of feeder cells in 96-well, flat-bottomed tissue culture plates. These subcloned hybridomas were subsequently rescreened first for their reactivity with rsCD4 by rsCD4-ELISA and then, rsCD4 reactive clones were further screened for the staining activities of their antibodies with HPB-ALL cells. Only two clones, designated as B4 and M2, having moderate rsCD4 reactivity and staining brightly the HPB-ALL cells were selected for subsequent recloning and maintained as ascites by i.p. injection of $1 \times 10^7$ cells into nu/nu mice primed with pristane. The binding and neutralization properties of the antibodies secreted by these two clones were characterized, together with other CD4-reactive monoclonal antibodies, as shown in Examples 4–13.

EXAMPLE 4

Bona fide CD4 Specific Monoclonal Antibodies Developed through Immunization of BALB/c Mice with rsCD4

Results

BALB/c mice were immunized intraperitoneally with 10 μg rsCD4 in Complete Freund's Adjuvant (CFA) on day 0, and boosted with 10 μg rsCD4 in Incomplete Freund's Adjuvant (ICFA) on days 21, 42 and 137 with a final boost of 10 μg rsCD4 in PBS injected intravenously on day 145. Splenectomy and fusion were performed 3 days after the last boost. Wells that contained antibodies reactive with rsCD4 were selected by rsCD4-ELISA. Four hybridomas, designated as E6, E31, H5 and J33, were harvested and single-cell cloned. These hybridomas were subsequently recloned and maintained for ascites development. As a control, one guinea pig was immunized with 100 μg rsCD4 in Complete Freund's Adjuvant on day 0, and boosted with 100 μg rsCD4 in Incomplete Freund's Adjuvant on days 14 and 28. Serum from this animal was obtained for days 28 and 42 to serve as a positive control for anti-rsCD4.

These four hybridomas and their antibody binding and neutralization properties were characterized and compared to those of MAbs B4 and M2, as shown in Examples 6–10.

EXAMPLE 5

Bona fide CD4 Specific Monoclonal Antibodies developed through Immunization of BALB/c Mice with HPB-ALL Cells Followed by Boosts with a gp120-rsCD4 Complex Results BALB/c mice were immunized intraperitoneally with $5 \times 10^6$ HPB-ALL cells in CFA on day 0, boosted with $5 \times 10^6$ HPB-ALL cells in ICFA on day 28, followed by three weekly boosts with HIV-1 gp120-rsCD4 complex (10 μg each) in ICFA beginning day 56. Splenectomy and fusion was performed 3 days after the final boost. Wells that contained antibodies reactive with rsCD4 were identified. Three hybridomas, designated as D5, E2, and I26, were selected, cloned, recloned and maintained for ascites development.

These three hybridomas and their antibody binding and neutralization properties were characterized and compared to those of MAbs B4 and M2, as shown in Examples 6–10.

EXAMPLE 6

Characterization of CD4 Reactive Monoclonal and Polyclonal Antibodies for their Individual Binding and HIV Primary Isolate Neutralizing Activities Specific Procedures for the determination of monoclonal antibody reactivities with rsCD4, rsCD4 in association with a peptide derived from the CCKR5 surface molecule, synthetic CD4 peptides, and with CD4-expressing cells The procedure for the determination of virus neutralization by antibody is described in Example 1, and the procedures for determination of antibody binding to rsCD4 and to the cell surface of CD4-expressing cells are described in Example 3. Only specific procedures for the determination of antibody reactivities with synthetic CD4 peptides and ELISA inhibition assays to confirm the results of epitope mapping are provided in this example.

Synthetic CD4 Peptides

Peptides listed in Table 1 were synthesized by the Merrifield solid-phase synthesis technique on Applied Biosystems automated peptide synthesizers (Models 430, 431 and 433A) using Fmoc chemistry. After complete assembly of the desired peptide, the resin was treated according to standard procedure using trifluoroacetic acid to cleave the peptide from the resin and deblock the protecting groups on the amino acid side chains. For cyclic peptide, the cleaved peptide was dissolved in 15% DMSO in water for 48 hrs to facilitate intradisulfide bond formation between cysteines. Peptides marked on Table 1 by * have been so cyclized. Other peptides are linear. Peptides marked by ‡ also contain a gly—gly spacer and a T cell helper epitope from hepatitis B virus (HBV). The cleaved, extracted and washed peptides were purified by HPLC and characterized by mass spectrometry and reverse phase HPLC.

Synthetic CD4 peptide-based ELISAs

The synthetic CD4 peptide based ELISAs were performed essentially the same as the rsCD4 ELISA described herein above except for the antigen coating step, where microtiter wells were coated for 1 hr at 37° C. with the designated CD4 peptide at 5 μg/mL, instead of rsCD4 at 0.25 μg/mL at 4° C.

ELISA Inhibition Assays

Peptide-induced inhibition of antibody binding in the rsCD4 ELISA was measured by preincubating diluted samples, at an endpoint rsCD4 binding dilution, with the competing peptide at the indicated concentration ranging from 1.67 mg/mL to 16.7 μg/mL for 1 hr at 37° C. The preincubated sample and peptide mixture was used directly in the standard rsCD4 ELISA procedure described herein above. Percent inhibition was calculated relative to the appropriate identically diluted monoclonal antibody which was preincubated in the absence of peptide. rsCD4-induced inhibition of antibody binding in the rsCD4 ELISA was similarly measured by preincubating diluted samples, at an endpoint rsCD4 binding dilution, with the competing rsCD4 at the indicated concentration.

Indirect immunofluorescence inhibition assay

For competitive inhibition assays employing the indirect immunofluorescence staining technique, cells were incubated with various interfering reagents at a specified step and washed twice in the same washing buffer in between any two incubations.

Results

Nine CD4-reactive monoclonal antibodies selected from the above three fusion experiments described in Examples 3, 4 and 5 were further characterized for (1) their reactivity pattern with CD4-expressing cells by indirect immunofluorescence assay, (2) their antigenic determinants on CD4, determined by direct binding and indirect inhibition ELISAs using as solid phase antigens the carefully designed synthetic CD4 peptides shown in Table 1, and (3) their ability to neutralize primary isolates of HIV by the MT-2 Microplaque Neutralization Assay.

Antibody characterization

With the exception of monoclonal antibody B4 which is a murine immunoglobulin of γ2a,κ type, all other monoclonal antibodies are of the γ1,κ type (Table 7) as determined by the Murine Hybridoma Subisotyping Kit (Calbiochem, San Diego, Calif., Cat. No. 386445). Of the nine selected monoclonal CD4 reactive antibodies, all showed immunoreactivity with the rsCD4 protein as demonstrated by the rsCD4 ELISA (Table 4) with MAbs J33, H5, E6, E2 and I26 having relatively strong binding reactivities, with D5 having relatively weak binding reactivity and with MAbs B4, M2 and E31 having moderate binding reactivities. The guinea pig anti-rsCD4 serum obtained from the 28th day bleed of an animal previously twice immunized with 100 μg of rsCD4 in complete and incomplete adjuvants was found to have extremely high reactivity with rsCD4 by rsCD4 ELISA with an endpoint titer of >$10^5$. This serum has been shown to have reactivities with multiple domains of rsCD4 and is thus used as a bona fide anti-CD4 positive control in subsequent antibody characterization experiments. See, Tables 4, 7, 8.

TABLE 4

Mapping of Antigenic Determinants for Various CD4 Reactive MAbs Using Designed Synthetic Peptides from Extracellular Domains 1–4 of the CD4 Molecule A492nm of individual peptide ELISA

| MAb | D1 (1–111) | | | | | | | D2 (112–181) | | D3 (182–286) | | D4 (297–375) | | rsCD4 |
| | 1816d (1–20) | 1858 HBVTh- (1–20) | 1403a (41–55) | 1461a (35–59*) | 1852 (68–92*) | 1589a (79–96*) | 1460c (60–109) | 1612a (133–151*) | 1817b (118–165*) | 1689a (213–251*) | 1693a (235–251*) | 1868a (297–351*) | 1701a (361–375*) | |
| --- | --- | --- | --- | --- | --- | --- | --- | --- | --- | --- | --- | --- | --- | --- |
| B4 | 0.125 | 0.166 | 0.115 | 0.117 | 0.285 | 0.180 | 0.165 | 0.101 | 0.295 | 0.155 | 0.226 | 0.257 | 0.217 | 1.424 |
| M2 | 0.201 | 0.189 | 0.084 | 0.081 | 0.192 | 0.129 | 0.159 | 0.090 | 0.179 | 0.113 | 0.168 | 0.158 | 0.185 | 0.871 |
| E6 | 0.065 | 0.094 | 2.046 | 2.195 | 0.082 | 0.052 | 0.069 | 0.053 | 0.085 | 0.054 | 0.074 | 0.064 | 0.067 | 2.007 |
| E31 | 0.062 | 0.088 | 0.062 | 0.071 | 0.080 | 0.064 | 0.069 | 0.077 | 1.936 | 0.060 | 0.085 | 0.063 | 0.065 | 0.936 |
| H5 | 0.065 | 0.087 | 0.058 | 0.065 | 0.115 | 1.972 | 2.003 | 0.244 | 0.211 | 0.057 | 0.088 | 0.064 | 0.073 | 1.984 |
| J33 | 0.132 | 0.138 | 0.067 | 0.083 | 1.046 | 0.063 | 0.100 | 2.348 | 2.022 | 0.063 | 0.087 | 0.116 | 0.081 | 2.059 |
| D5 | 1.095 | 0.175 | 0.061 | 0.059 | 0.084 | 0.058 | 0.057 | 0.069 | 0.063 | 0.067 | 1.972 | 0.061 | 0.064 | 0.335 |
| E2 | 0.088 | 0.182 | 0.058 | 0.058 | 0.060 | 0.054 | 0.054 | 0.063 | 0.069 | 2.169 | 0.063 | 0.056 | 0.055 | 2.083 |
| I26 | 0.197 | 0.292 | 0.060 | 0.057 | 0.063 | 0.056 | 0.057 | 0.060 | 0.056 | 0.054 | 2.310 | 0.058 | 0.062 | 2.182 |
| Gpα racD4 A492nm# | 2.140# | 1.936 | 0.180 | 2.027 | 1.995 | 0.241 | 0.498 | 2.027 | 1.965 | 0.164 | 0.336 | 1.921 | 0.126 | 1.935 |
| Titer (Log)$_{10}$ | >5 | >5 | <2 | 4.472 | 4.779 | 2.046 | 2.419 | >5 | >5 | <2 | 2.168 | >5 | <2 | >5 |

Samples with $A_{492}$ larger than 0.150 are considered reactive and the reactivities are underlined (and shaded) for ease of pattern recognition.
A492nm reading for guinea pig anti-rsCD4 serum (4 wpi) at 1:100 dilution.
*Cyclic peptide Identification of antigenic determinants for each of the monoclonal antibodies Efforts to identify the antigenic determinants on the CD4 molecule recognized by each of the monoclonal antibodies were made through direct binding studies with the collection of synthetic CD4 peptides shown in Table 1. These peptides were designed in accordance to the available three dimensional (3-D) structure for the first two domains of human CD4 (Wang et al., Nature, 1990, 348:411) and the structure for the third and fourth domains of the molecule as projected from an homology analysis of the available 3-D structure of rat CD4 (Brady et al., Science, 1993, 260:979) so as to maximize the serological crossreactivity between the synthetic and native CD4. Binding to the fragments is compared to binding to rsCD4. Binding for each of the antibodies was determined by enzyme immunoassays in serial dilutions beginning at an antibody concentration of 50 $\mu$g/mL for detection of bound murine antibody, using the indicated peptides or rsCD4 as solid-phase antigens. Binding results are expressed as Absorbances in the peptide and rsCD4 based ELISAs. For simplicity of pattern recognition, only results obtained at the highest antibody concentration in the dilution series giving rise to maximal 50 $\mu$g/mL reactivity signals were presented for each of the antibodies. Samples of $A_{492}$ greater than 0.150 are considered reactive. Positive binding is denoted in Table 4 by underlining. This intensive mapping effort resulted in the identification of peptide binding sites and localizations of their epitopes in reference to the CD4 primary sequence (Table 4) for all of the monoclonal antibodies.

Figure 2A:
Figure 2B:
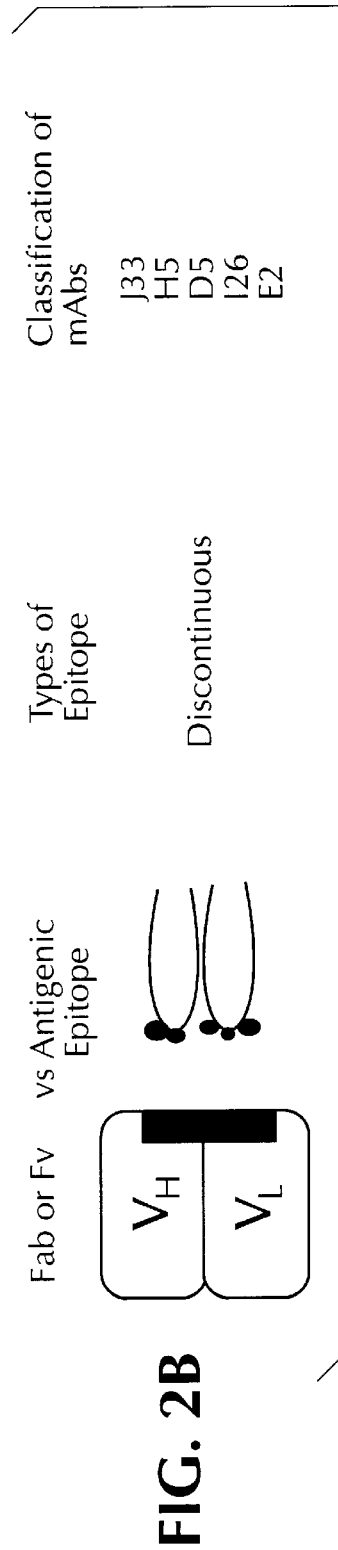
Figure 2C:
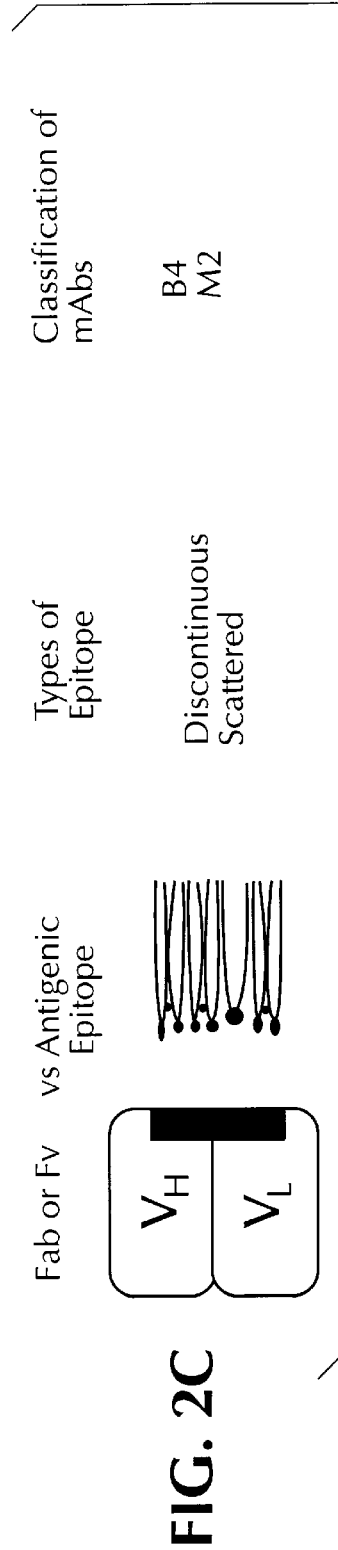

The peptide reactivity patterns shown in Table 4 separated the nine antibodies into three groups (FIG. 2). Antibodies of the first group recognized linear epitopes and included two monoclonal antibodies designated as E6 and E31. These were found to recognize linear epitopes presented by one synthetic peptide (Table 4). More specifically, monoclonal antibody E6 was found to recognize an epitope which was localized exclusively to a region specified by as few as 15 amino acids ($AA_{41}$–$AA_{55}$) from the first domain overlapping the CDR2 HIV gp120 binding region, and E31 reacted with larger cyclic peptide $AA_{118}$–$AA_{165}$.

Antibodies of the second group, consisting of five monoclonal antibodies H5, J33, E2, D5 and I26, were found to react with linear peptides derived from two regions of CD4, with occasional preferential reactivity with one (Table 4), thus qualifying these antibodies as recognizing discontinuous conformational epitopes. More specifically, H5 was found to react primarily with the CDR3 region ($AA_{79}$–$AA_{96}$) from the first domain of the CD4 molecule while having a modest reactivity with the second domain of CD4 characterized by two cyclic peptides $AA_{133}$–$AA_{151}$ and $AA_{118}$–$AA_{165}$; J33 was found to react primarily with the center of the CD4 second domain characterized by a cyclic peptide $AA_{133}$–$AA_{151}$ while having a moderate reactivity with the first domain, characterized by an artificial dimer of peptides ($AA_1$–$AA_{20}$) and ($AA_{68}$–$AA_{92}$) (P1852, Table 4) from the CDR1 and CDR3 regions respectively with both contributing to the formation of an intradomain disulfide bond; D5 recognized two stretches of amino acids from both the first and third domains characterized by cyclic peptides $AA_1$–$AA_{20}$ and $AA_{235}$–$AA_{251}$ respectively; E2 recognized principally a stretch of amino acids from the third domain characterized by a cyclic peptide $AA_{235}$–$AA_{251}$ while having a modest reactivity with the N-terminal portion ($AA_1$–$AA_{20}$) of the CD4 molecule characterized by a hybrid peptide 1858; and I26 recognized an area largely overlapping with that of D5 for preferential reactivity with the third domain characterized by a cyclic peptide $AA_{235}$–$AA_{251}$.

Antibodies of the first two groups obtained from mice immunized with a purified rsCD4 or a well defined rsCD4-gp120 complex, which demonstrated strong reactivities with the native rsCD4 and definitive reactivities with various domains of the CD4 molecule, are considered bona fide anti-CD4 antibodies.

And finally, monoclonal antibodies B4 and M2, of the third group, were found to react moderately with the native rsCD4 even at a saturating concentration (50 $\mu$g/mL) as shown by the rsCD4 ELISA (Table 4), whereas having only weak reactivities with peptides from several regions $AA_1$–$AA_{20}$, $AA_{79}$–$AA_{96}$, $AA_{118}$–$AA_{165}$, $AA_{213}$–$AA_{226}$, $AA_{235}$–$AA_{251}$, $AA_{297}$–$AA_{351}$ and $AA_{361}$–$AA_{375}$ of CD4. Interestingly, the reactivity of B4 for the CDR2 region of domain 1, where well-known anti-CD4 antibodies Leu3A and OKT4A were reported to bind, was conspicuously missing when compared to its reactivities with other peptides. The two antibodies of this third group are qualified as recognizing discontinuous scattered conformational epitopes.

Identification of mimetic peptides interfering with B4-rsCD4 and M2-rsCD4 interactions In order to further decipher the potential contacting sites on the CD4 molecule for both B4 and M2, peptides from regions near to those shown to be responsible for B4-rsCD4 or M2-rsCD4 bindings (Table 4) were tested in an ELISA for their ability to inhibit B4-rsCD4 and M2-rsCD4 interactions.

The signal generated at endpoint concentration (e.g. 10 $\mu$g/mL for B4 and 20 $\mu$g/mL for M2) in an rsCD4 ELISA was employed as a positive control for the competitive peptide binding studies.

Table 5 depicts per cent inhibition results obtained in the rsCD4 ELISA where designed CD4 peptides were serially diluted and individually incubated with 0.1 mL of B4 at 10 $\mu$g/mL prior to the binding of B4 to the solid phase-bound rsCD4. Peptides were employed for competitive inhibition at concentrations of 1.67 mg/mL, 167 $\mu$g/mL and 16.7 $\mu$g/mL (conc 1, conc 2, and conc 3, respectively). Only results from those peptides demonstrating strong inhibition or enhancement of B4-rsCD4 interaction are shown for comparison. Enhancement is expressed by negative values for inhibition.

Table 6 depicts the per cent inhibition results obtained in the rsCD4 ELISA where designed CD4 peptides were serially diluted as in Table 5 and were individually incubated with 0.1 mL of M2 at 20 $\mu$g/mL prior to binding M2 to the solid phase-bound rsCD4. Only results from those peptides demonstrating strong inhibition or enhancement of M2-rsCD4 interaction are shown for comparison.

As shown in Table 5, the binding of B4 to rsCD4 was found to be inhibited strongly by CD4 peptides from regions $AA_1$–$AA_{20}$, $AA_6$–$AA_{20}$, $AA_{81}$–$AA_{92}$, $AA_{79}$–$AA_{88}$, $AA_{154}$–$AA_{165}$, and $AA_{297}$–$AA_{351}$, indicating the involvement of these regions in the formation of the CD4 associated conformational epitope. Contrary to reports by Y. Chiba, supra, for monoclonal Leu3A and Jameson et al., supra for OKT4A, significant enhancement for the B4-rsCD4 binding was observed with peptides from regions of $AA_{36}$–$AA_{47}$, thus suggesting spatial proximity but not direct involvement of the $AA_{30}$–$AA_{47}$ to the binding of B4. The inhibiting sites are are frequently located around the intra-disulfide bonds (Table 5). A similar pattern of inhibition and enhancement by the various CD4 peptides with only minor differences was observed for M2 (Table 6).

TABLE 5

Competitive Inhibition or Enhancement of "B4-rsCD4" Interaction by Designed CD4 Peptides

| Peptide code | Peptide description (CD4 AA) | % inhibition of "B4-rsCD4" interaction of peptide concentrations | | |
|---|---|---|---|---|
| | | Conc 1 | Conc 2 | Conc 3 |
| 1816d | CD4 (1–20) | 64 | 53 | 29 |
| 1767b | HBVTh-CD4 (6–20) | 76 | 68 | 35 |
| 1405b | HBVTh-CD4 (81–92) | 89 | 52 | 20 |
| 1813b | HBVTh-CD4 (79–88) | 93 | 69 | 32 |
| 1768a | CD4 (154–165) | 82 | 37 | 6 |
| 1768b | HBVTh-CD4 (154–165) | 76 | 44 | 11 |
| 1868a | CD4 (297–351*) | 38 | 30 | 19 |
| 1624a | CD4 (36–47) | −215 | −207 | −108 |

*Cyclic peptide

TABLE 6

Competitive Inhibition or Enhancement of "M2-rsCD4" Interaction by Designed CD4 Peptides

| Peptide code | Peptide description (CD4 AA) | % inhibition of "M2-rsCD4" interaction of peptide concentrations | | |
|---|---|---|---|---|
| | | Conc 1 | Conc 2 | Conc 3 |
| 1816d | CD4 (1–20) | 74 | 60 | 17 |
| 1767b | HBVTh-CD4 (6–20) | 82 | 72 | 43 |
| 1405b | HBVTh-CD4 (81–92) | 88 | 53 | 16 |
| 1813b | HBVTh-CD4 (79–88) | 92 | 70 | 37 |
| 1768a | CD4 (154–165) | 86 | 36 | 19 |
| 1768b | HBVTh-CD4 (154–165) | 85 | 45 | 25 |
| 1868a | CD4 (297–351*) | 56 | 43 | 17 |
| 1624a | CD4 (36–47) | −261 | −251 | −141 |

*Cyclic peptide

EXAMPLE 7

Binding Properties of the Monoclonal Antibodies for the Cell Surface of CD4-expressing Cells The nine CD4-reactive monoclonal antibodies along with the guinea pig anti-rsCD4 serum were used in various indirect immunofluorescence assays for detection of the surface expression of their epitopes on the HPB-ALL cells and for determination of the spatial relationship between HIV-1 gp120 binding and the CD4 epitopes recognized by the various CD4-reactive antibodies.

Results

Table 7 summarizes results obtained for the murine monoclonal antibodies developed from three fusion experiments relating to (1) their isotypes; (2) their reactivities with rsCD4 by rsCD4 ELISA; (3) their reactivities with surface CD4 by an indirect immunofluorescence assay registering per cent of cell reactivity, degree of staining (0–3+) and binding patterns; (4) the ability of prior bound HIV gp120 to interfere with binding of the antibodies to host cell antigen complex comprising CD4; (5) the ability of the prior bound antibodies to inhibit binding of HIV gp120 to surface host cell antigen complex comprising CD4, and (6) ability of the antibodies to neutralize HIV-1 primary isolates, e.g., 23135.

Representations of the spatial relationships between HIV gp120 binding sites on cell-membrane bound CD4 and the CD4 epitopes recognized by the various CD4 reactive monoclonal antibodies are specifically addressed by items (3), (4) and (5) of Table 7. Binding patterns to CD4 are shown by indirect immunofluorescence staining of HPB-ALL cells using Fluorescein isothiocyanate (FITC)-labeled anti-mouse IgG, FITC-labeled anti-guinea pig IgG or FITC-labeled gp120. The patterns are shown for binding of anti-CD4 murine monoclonals in the absence of gp120 (3), for the binding of FITC-labeled gp120 in the presence of pre-bound monoclonal antibodies (5), and binding of monoclonal antibodies in the presence of pre-bound gp120 (4). The uniqueness of the neutralization activity of monoclonal antibodies B4 and M2 compared to the neutralization activities of seven other anti-CD4 monoclonal antibodies which have binding sites on CD4 distinct from that of B4 or M2, but in some cases near that of B4, is addressed in items (5) and (6).

TABLE 7

Reactivities of MAbs with rsCD4 and Surface CD4 Receptor Complex and Inhibition of HIV gp120 Binding to CD4 Cells by MAbs

| Clone | (1) Murine Ig isotype | Immunogen | (2) $A_{492\ nm}$ Reactivity to rsCD4 | (3) HPB-ALL surface CD4 binding pattern | (4) MAb binding reactivity to HPB-ALL after prior binding of gp120 to the cells Inhibition Yes or No | (5) gp120-FITC binding to HPB-ALL after prior binding with MAb Inhibition Yes or No | (6) 50% end point for neutralization of HIV-1 primary isolate (23135) |
|---|---|---|---|---|---|---|---|
| B4 | γ2a, κ | HPB-ALL (PBS) | 1.424 | >90%; 3 + (A) | >90%; 2 + (A); Yes, partial | 0; Yes | 0.21 μg/mL |
| M2 | γ1, κ | HPB-ALL (PBS) | 0.871 | >90%; 3 + (A) | >90%; 2 + (A); Yes, partial | 0; Yes | 0.38 μg/mL |
| E6 | γ1, κ | rsCD4 (CFA, ICFA) | 2.007 | >90%; 2 + (B) | 0; Yes | 0; Yes | 59 μg/mL |
| H5 | γ1, κ | rsCD4 (CFA, ICFA) | 1.984 | >90%; 1 + (B) | >90%; 1 + (B); No | >90%; 1 + (C); No | 45.5 μg/mL |
| E31 | γ1, κ | rsCD4 (CFA, ICFA) | 0.936 | >90%; 1 + (B) | >90%; 1 + (B); No | >90%; 1 + (C); No | >100 μg/mL |
| J33 | γ1, κ | rsCD4 (CFA, ICFA) | 2.059 | >90%; 1 + (B) | >90%; 1 + (B); No | >90%; 1 + (C); No | >100 μg/mL |
| D5 | γ1, κ | HPB-ALL (CFA, ICFA) + gp120 rsCD4 complex | 1.930 | >90%; 1 + (B) | 0 | >90%; 1 + (C); No | >10 μg/mL |

TABLE 7-continued

Reactivities of MAbs with rsCD4 and Surface CD4 Receptor Complex
and Inhibition of HIV gp120 Binding to CD4 Cells by MAbs

| Clone | (1) Murine Ig isotype | Immunogen | (2) $A_{492\ nm}$ Reactivity to rsCD4 | (3) HPB-ALL surface CD4 binding pattern | (4) MAb binding reactivity to HPB-ALL after prior binding of gp120 to the cells Inhibition Yes or No | (5) gp120-FITC binding to HPB-ALL after prior binding with MAb Inhibition Yes or No | (6) 50% end point for neutralization of HIV-1 primary isolate (23135) |
|---|---|---|---|---|---|---|---|
| E2 | γ1, κ | HPB-ALL (CFA, ICFA) + gp120 rsCD4 complex | 2.020 | 10%; 1 + (B) | 0 | >90%; 1 + (C); No | >10 μg/mL |
| I26 | γ1, κ | HPB-ALL (CFA, ICFA) + gp120 rsCD4 complex | 0.793 | 0 | 0 | >90%; 1 + (C); No | >10 μg/mL |
| PBS | N/A | N/A | N/A | N/A | N/A | >90%; 1 + (C); No | N/A |
| gpα rsCD4 | N/A | rsCD4 (CFA,ICFA) | $Log_{10}$ Titer => 5 | >90%; 1 + (B) | >90%; 1 + (B); No | ND | <1:10 dilution |

Binding patterns: A: caps and patches; B: patches; C: clusters (FIG. 3).

Monoclonal antibody E6, recognizing a linear determinant presented by a stretch of 15 amino acids derived from the first domain ($AA_{41}$–$AA_{55}$) overlapping the CDR2 region of the CD4 gp120 binding site (Wang et al., Nature, 1990, 348:411 and Ryu et al., Nature, 1990, 348:419), was found to react strongly with both the rsCD4 protein and the HPB-ALL cells indicating a more exposed surface nature for this HIV binding site.

However, despite the relatively strong reactions exhibited by the bona fide anti-CD4 monoclonal antibodies J33, H5, and E2 to rsCD4 molecule, as demonstrated by the rsCD4 ELISA results, only a moderate staining of the HPB-ALL cells was observed. The scoring of 1+ for these MAbs indicates a much less exposed status for their epitopes on cell-surface CD4 antigen complex. Furthermore, guinea pig anti-rsCD4 serum characterized previously (Example 6) for high recognition of immunodominant epitopes from domains 1, 2 and 4 as well as rsCD4, showed only moderate staining of the HPB-ALL cells by the indirect immunofluorescence assay, again indicating an overall lower exposure for the CD4 molecule on the surface of CD4 positive cells. In contrast, both monoclonal antibodies B4 and M2 stained the cells intensely despite their relatively moderate reactivity with rsCD4, indicating that contact with site(s) on coreceptor(s) other than CD4 are involved, coreceptor(s) that together with CD4 form host cell antigen complex comprising CD4. This is also demonstrated by the inhibition of B4-rsCD4 interaction by several CD4-derived peptides (Table 5), indicative of a larger antigen complex comprising the CD4 protein on the cell surface (FIG. 3) and an overall structural difference between rsCD4 and the cell-surface antigen complex comprising CD4.

Inhibition of gp120 binding to CD4 cells by the monoclonal antibodies

The binding characteristics for these monoclonal antibodies were further evaluated for their ability to inhibit the binding of HIV to the CD4-expressing HPB-ALL cells (Table 7(5)) under the condition of prior incubation of the cells with an individual monoclonal antibody (100 μL at a saturating concentration of 50 μg/mL), or PBS as a negative control, followed by subsequent incubation of the cells with 100 μL of FITC-labelled HIV-gp120 at a 1:200 dilution. Cells were washed twice in between incubations with primary and labeled secondary antibodies.

For cells first incubated with PBS followed by subsequent incubation with the FITC-gp120, a characteristic staining pattern of small clusters with a score of 1+ brightness was obtained (Table 7 and FIG. 3). Such a characteristic FITC-gp120-HPB-ALL staining pattern was also obtained for cells first incubated with monoclonal antibody H5, E31, J33, D5, E2, or I26 followed by FITC-gp120 staining, thus demonstrating a lack of FITC-gp120 binding inhibition by these antibodies and suggesting a lack of association between the gp120 binding site and the binding sites of these anti-CD4 antibodies. However, prior staining with monoclonal antibody B4, M2, or E6 completely abolished the characteristic staining pattern of FITC-gp120, indicating the strong inhibitory nature of these antibodies on CD4-gp120 binding and suggesting associations between the gp120 binding site and the binding sites of B4, M2 and E6. Since unlike E6 antibody B4 or M2 does not recognize the HIV binding site (i.e. the CDR2 region) on the CD4, this inhibitory activity of B4 or M2 was interpreted as steric hinderance.

Inhibition of monoclonal antibody binding to CD4-expressing cells by gp120 The effect of prior gp120 binding to the CD4-expressing cells on the cells' subsequent binding by these CD4 reactive monoclonal antibodies was also evaluated.

$10 \times 10^6$ HPB-ALL cells were first incubated with an excessive amount of gp120, 10 μg, from HIV-1 IIIB strain (American Biotechnologies, Inc., Cambridge, Mass.), at 37° C. for 45 minutes. The gp120 treated HPB-ALL cells were washed twice in the washing buffer and then incubated with the specified monoclonal antibody according to the indirect immunofluorescence staining procedure described herein above.

Only the binding of E6 to CD4-expressing cells was found to be completely abolished by prior binding of gp120 (Table 7, (4)). The epitope recognized by E6 (Table 4) was mapped near those recognized by OKT4A and Leu3A. The binding of monoclonal antibodies B4 and M2 to CD4-expressing cells was not significantly affected by the prior binding of gp120 to CD4-expressing cells, indicating that these two antibodies can bind to CD4-expressing cells following HIV binding. This observation provides a possible mechanism for the in vitro neutralization capability of antibody B4 at a post-viral binding level shown in Example 16 (see Tables 16 and 17) and the in vivo efficacy of B4 in post-exposure prevention of HIV infection as demonstrated in the hu-PBL-SCID mice model (See Example 18, Table 20).

EXAMPLE 8

Neutralization of HIV Primary Isolate by the Monoclonal Antibodies

Results

When the nine CD4 reactive monoclonal antibodies and the guinea pig anti-rsCD4 serum were tested for their ability to neutralize HIV-1 primary isolate 23135 by a MT-2 microplaque assay as described herein (Example 1), only B4 and M2 demonstrated potent inhibitory activity giving rise to a 50% inhibition at concentrations of 0.21 and 0.38 μg/mL, respectively (Table 7, (6)). Antibody E6, identifying a site near the HIV gp120 binding site, close to the sites recognized by OKT4A and Leu3A, and H5 principally recognizing a site located in the CDR3 region of the CD4 first domain, both gave only marginal neutralization with 50% endpoint concentrations of 59 and 45.5 μg/mL respectively. Unlike monoclonal antibodies B4 and M2, the other bona fide anti-CD4 monoclonal antibodies do not display significant primary isolate neutralizing activity as measured by inhibition of microplaque formation (i.e. inhibition of cell fusion and infection by the primary HIV-1 isolate). Despite the strong reactivity of the guinea pig anti-rsCD4 serum with the rsCD4, this serum did not inhibit HIV-induced cell fusion and infection even at a high anti concentration of serum dilution <1:10.

EXAMPLE 9

Optimal Immunization and Screening Strategy for Hybridoma Selection

Based on the information obtained from Table 7, it is concluded here and in Table 12 that hyperimmunization of mice with freshly washed adjuvant-free CD4-expressing cells leads to successful generation of hybridomas secreting antibodies highly reactive with a host cell antigen complex comprising CD4. To enhance the frequency of generating hybridoma clones reactive for CD4-expressing cells, HPB-ALL or SUPT1 cells can be first incubated with a mixture of monoclonal antibodies directed against T-cell surface antigens, including antibodies directed to HLA A-B, C, CD3, T cell receptor, CD8, CD6, CD2 and CD5 antigens, to mask HPB-ALL surface antigens other than the CD4 comprising antigen complex from exposure to the host's immune system, thus preferentially targeting the host's immune response towards the cell surface CD4 comprising antigen complex containing both the receptor and co-receptor(s) for HIV. A straightforward three step screening strategy including first the selection of hybridomas having positive reactivity with rsCD4 and/or a preferential reactivity with rsCD4 preincubated with p2047, a peptide derived from the third external domain of the chemokine receptor CC-CKR5, over that with rsCD4, by ELISAs; followed by selection from among the rsCD4/p2047 and rsCD4-reactive clones for those having strong reactivity with CD4-expressing cells such as HPB-ALL or SUP-T1 cells by indirect immunofluorescence assay, followed by selection amongst the surface CD4-reactive hybridomas for those secreting antibodies with neutralizing activities for a primary isolate of HIV-1, as tested by a standard MT2 microplaque reduction assay, is useful.

EXAMPLE 10

Selection of CD4-Reactive Monoclonal Antibodies with Binding Properties Similar to That of B4

Monoclonal antibodies with binding properties similar to that of B4 can be easily identified from among CD4-reactive antibodies by employment of competitive inhibition immunoassays that detect positive B4 signals generated through either (1) HRP-conjugated monoclonal antibody B4 prepared as described herein below in a rsCD4 ELISA system, or (2) biotinylated B4 prepared as described herein below accompanied by FITC-avidin staining of the HPB-ALL cells in an indirect immunofluorescence assay system, as the comparison methods.

Specific procedures for the biotinylation or enzyme conjugation of monoclonal antibody B4.

Biotinylation of monoclonal antibody B4 using the succinimide ester

Monoclonal antibody B4 was purified by Protein A-affinity chromatography and adjusted to 1 mg/mL in PBS. 0.71 mg of N-hydroxysuccinimide biotin (Biotin-X-NHS, Boehringer Mannheim Biochemicals, Indianapolis, Ind., Cat. No. 1008960) was dissolved into 0.31 mL of DMSO (Boehringer Mannheim Biochemicals, Cat. No. 1418165) followed by the addition of 5 mg B4 in 5 mL PBS resulting in a molar ratio of 50 to 1 for biotin and B4. The mixture was stirred for two hours at room temperature followed by extensive dialysis at 2–8° C. against PBS resulting in a final concentration of B4 at 0.71 mg/mL. The biotinylated B4 was used as the tracer in a competitive immunofluorescence staining assay for inhibition of "B4-CD4-expressing cells" interaction by various monoclonal antibodies.

Conjugation of horseradish peroxidase (HRP) to monoclonal antibody B4 by the periodate method The enzyme-antibody conjugation procedure was carried out essentially as described by Wilson and Nakane, (Knapp et al., eds, 1978 Elsevier/North-Holland Biomedical Press, *Immunofluorescence and Related Staining Techniques,* p215) at an enzyme to antibody molar ratio of 0.48 to 1. The horseradish peroxidase (HRP)-B4 conjugate was dialyzed extensively in PBS after conjugation with a resulting antibody concentration of 0.18 mg/mL. This conjugate was used at 50 μg/mL in a competitive ELISA for inhibition of "B4-rsCD4" interaction by various monoclonal anti-CD4 antibodies.

Detection and competitive inhibition

Table 8 depicts results obtained from a study involving competitive inhibition of "Biotinylated B4-surface CD4 comprising complex" interaction with nine monoclonal anti-CD4 antibodies (MAbs, B4, M2, E6, H5, J33, E31, D5, E2 and I26) and a guinea pig anti-rsCD4 serum. Competitive inhibition study was performed by an indirect immunofluorescence assay, where $0.5 \times 10^6$ CD4-expressing HPB-ALL cells were incubated with individual antibodies at a saturating concentration of 10 μg/mL at 100 μL per test or the guinea pig serum at a 1:50 dilution also at 100 μL per test, thoroughly washed, followed by a second staining with 100 μL of the biotinylated B4 (at a 1:1000 dilution from a stock solution of 0.71 mg B4/mL), thoroughly washed, followed by a tertiary staining with 100 μL of an FITC-avidin tracer (Pierce Chemical Co., Rockford Ill., Cat. No. 21221) at a 1:250 dilution in PBS (pH 8.2).

Table 9 depicts results obtained in a study involving competitive inhibition of "HRP B4-rsCD4" interaction study with nine monoclonal anti-CD4 antibodies (MAbs B4, M2, E6, H5, J33, E31, D5, E2 and I26). Competitive inhibition study was performed by a direct rsCD4 ELISA where the solid phase wells coated with rsCD4 were pretreated with CD4 peptide 1624a to enhance B4 binding signals. The rsCD4-coated wells were incubated with 30 μL of individual antibodies (50 μg/mL at 100 μL per well) in the presence of HRP-conjugated monoclonal antibody B4 50 μg/mL at 120 μL.

Results

As shown in Table 8, among all the monoclonal antibodies and the guinea pig anti-rsCD4 serum tested, only B4 or M2 effectively inhibited the biotin-B4 (at a 1:1000 dilution) and FITC-avidin (Pierce Chemical Co., at a 1:250 dilution) staining of the HPB-ALL cells in an indirect immunofluorescence assay system. Similarly as shown in Table 9, of all the monoclonal antibodies tested, only monoclonal antibodies M2 and B4 exerted greater than 45% inhibition over the binding of HRP-B4 to the rsCD4 molecule in the rsCD4 ELISA. Thus, effective selection of hybridoma secreting antibodies having binding properties similar to that of B4, including its neutralizing activity against primary isolates of HIV, can be accomplished through competition immunoassays using HRP-conjugated or biotinylated B4 as the tracer, a selection process that is significantly easier than selection by in vitro functional assays such as the standard MT-2 microplaque neutralization assay. More importantly, none of the seven bona fide anti-CD4 monoclonal antibodies (i.e. MAbs, E6, H5, J33, E31, D5, E2 and I26) can effectively compete with B4 for reactivity to rsCD4 and surface CD4 receptor complex binding sites (Tables 8 and 9).

TABLE 8

Inhibition of "Biotin MAb B4-Surface CD4 Receptor Complex" Interaction by CD4 Reactive Monoclonal Antibodies

| MAb (10 μg/mL) | Indirect immunofluorescence | | |
|---|---|---|---|
| | % Positive cells | Intensity of staining | Inhibition |
| PBS + Biotinylated B4 + Avidin-FITC | >95 | 2.0 | Positive control |
| PBS + Avidin-FITC | 0 | 0 | N/A |
| B4 | 0 | 0 | Yes |
| M2 | 0 | 0 | Yes |
| E6 | >95 | 2.0 | No |
| H5 | >95 | 2.0 | No |
| E31 | >95 | 2.0 | No |
| J33 | >95 | 2.0 | No |
| D5 | >95 | 2.0 | No |
| E2 | >95 | 2.0 | No |
| I26 | >95 | 2.0 | No |
| G.P. αrsCD4 serum | >95 | 2.0 | No |

TABLE 9

Inhibition of "HRP MAb B4-rsCD4" Interaction by CD4 Reactive Monoclonal Antibodies

| MAb at 50 μg/mL | $A_{492\ nm}$ | % Inhibition |
|---|---|---|
| PBS | 1.658 | 0 |
| Blank | 0.049 | N/A |
| B4 | 0.338 | 80 |
| M2 | 0.884 | 47 |
| E6 | 1.262 | 24 |
| H5 | 1.222 | 26 |
| E31 | 1.494 | 10 |
| J33 | 1.105 | 33 |
| D5 | 1.468 | 11 |
| E2 | 1.533 | 8 |
| I26 | 1.530 | 8 |

1. Competition ELISA was performed with plate coated with rsCD4 at 0.25 μg/mL and 0.1 mL per well, at 4° C. for overnight. The plate was treated with a synthetic CD4 peptide 1624 (Table 1) at 50 μg/mL and 100 μL per well, at 37° C. for 1 hr to enhance reactivity.

TABLE 9-continued

Inhibition of "HRP MAb B4-rsCD4" Interaction by CD4 Reactive Monoclonal Antibodies

| MAb at 50 μg/mL | $A_{492\ nm}$ | % Inhibition |
|---|---|---|

2. Monoclonal antibodies were individually tested for competitive inhibition of peroxidase-conjugated monoclonal antibody B4 (B4-HRP) binding to rsCD4. 120 μL of B4-HRP at 50 μg/mL was mixed with 30 μL of a tested monoclonal antibody at 50 μg/mL. 30 mL of PBS instead of a tested monoclonal antibody was used as a control. 100 μL per well of the mixture was transferred to the rsCD4 coated plate to test the "B4-HRP-rsCD4" interactivity.
3. % inhibition was calculated as: [(A492nm of PBS Control − A492nm of Sample containing competing MAb) ÷ A492nm of PBS Control] × 100

EXAMPLE 11

Inhibition of "B4-rsCD4" but not "B4-surface CD4 Comprising Complex" Interaction by rsCD4: MAb is Reactive with a Host Cell Antigen Complex Comprising CD4

Results

Table 10 depicts results obtained from a study involving competitive inhibition of "B4-rsCD4" interaction in an indirect rsCD4 ELISA system employing rsCD4 as solid phase antigen (0.25 μg/mL, 0.1 mL/well, 4° C., overnight coating), and purified B4 at 2 μg/mL, 0.1 mL/well giving rise to an A492nm reading of 0.679 as the positive control. Increasing concentrations of rsCD4 from ranges of 0.008 to 25 μg/mL were preincubated with the purified B4 for 1 hr at room temperature prior to incubation with the solid phase rsCD4. As shown in Table 10, premix of 1 μg/mL of rsCD4 with 2 μg/mL of B4 will inhibit 50% of the interaction between B4 and solid-phase rsCD4.

Table 11 depicts results obtained in a study involving competitive inhibition of "Biotinylated B4-surface CD4 comprising complex" interaction in an indirect immunofluorescence assay employing HPB-ALL (0.2–0.5×10$^6$ cells per test in 0.1 mL) as the target cells and biotinylated B4 at 0.71 μg/mL, 0.1 mL per test, which gave a positive rate of 95% cells at a staining intensity of 3+. Increasing concentrations of rsCD4 from ranges of 0.005 to 50 μg/mL were preincubated with the biotinylated B4 for 1 hr at room temperature prior to incubation with the CD4-expressing HPB-ALL cells. As shown in Table 11, in contrast to the rsCD4 ELISA system, no inhibition was observed for the B4 staining of HPB-ALL cells when rsCD4 was added even up to the 50 μg/mL concentration. This reactivity demonstrates a novel recognition site for B4 the cell surface antigen complex comprising CD4, in comparison to the uncomplexed CD4 site of bona fide anti-CD4 antibodies. This result was confirmed by the immunofluroescence staining of HPB-ALL cells by the bona fide anti-CD4 monoclonals which was completely removed by pre-absorption with rsCD4 (data not shown).

All the observations on the binding reactivities of the CD4 reactive monoclonals with rsCD4, CD4-derived synthetic peptides, and the CD4-expressing HPB-ALL cells, can be summarized into the following four major findings:

(1) as shown in Table 4, Mabs B4 and M2 reacted moderately with the rsCD4 resembling a partial reactivity with the molecule whereas five (i.e. E6, H5, J33, E2 and I26) of the seven bona fide anti-CD4 monoclonals and the guinea pig anti-rsCD4 serum reacted more strongly with rsCD4 in an rsCD4 ELISA;

(2) as shown in Table 7, all bona fide anti-CD4 monoclonals and the guinea pig anti-CD4 serum reacted weakly with HPB-ALL cells with a characteristic "patches" binding pattern (pattern B), distinct from the "caps" pattern of Mabs B4 and M2 (pattern A);

(3) as shown in Table 8, preincubation of CD4-expressing HPB-ALL cells with the bona fide anti-CD4 monoclonals at a saturating concentration of 20 μg/mL or the guinea pig anti-rsCD4 serum at a saturating dilution of 1:50 did not inhibit the subsequent binding of biotinylated B4 to HPB-ALL cells whereas Mabs B4 and M2 did; and (4) as shown in Tables 10 and 11, a 50% inhibition of the "B4-rsCD4" interaction was achieved with 2 μg/mL of B4 at a 1 μg/mL concentration of rsCD4 whereas no inhibition of the "B4-CD4 comprising host cell antigen complex" interaction was observed with 0.71 μg/mL of biotinylated B4 even at a 50 μg/mL concentration of rsCD4.

Based on the above four findings, it was concluded that the binding specificities of Mabs B4 and M2 are readily distinguished from those of bona fide anti-CD4 antibodies by inclusion of sites that extend beyond that of the CD4 protein alone to include a host cell surface antigen complex comprising CD4, with CD4 constituting only a part of that host cell antigen complex.

TABLE 10

Inhibition of "B4[a]-rsCD4[b]" Interaction by rsCD4

| rsCD4 μg/mL | $A_{492\ nm}$ | % Inhibition[c] |
|---|---|---|
| 25 | 0.055 | 91.9 |
| 5 | 0.061 | 91.0 |
| 1.0 | 0.340 | 49.9 |
| 0.2 | 0.633 | 6.7 |
| 0.04 | 0.637 | 6.1 |
| 0.008 | 0.711 | −4.7 |
| 0 | 0.679 | 0 |

[a]Purified MAb B4 = 2 μg/mL
[b]rsCD4 coated at 0.25 μg/mL overnight at 4° C.
[c]% inhibition = [($A_{492nm}$ Control − $A_{492nm}$ Inhibition Conc)/$A_{492nm}$ Control] × 100

TABLE 11

Inhibition of "B4[a]-Surface CD4 Comprising Complex[b]" Interaction by rsCD4[c]

| | HPB-ALL Staining | | |
|---|---|---|---|
| rsCD4 (μg/mL) | % Positive cells | Pattern of staining | Inhibition |
| 50 | >95 | 3+ | No |
| 5 | >95 | 3+ | No |
| 0.5 | >95 | 3+ | No |
| 0.05 | >95 | 3+ | No |
| 0.005 | >95 | 3+ | No |
| 0 | >95 | 3+ | N/A |

[a]Biotinylated B4 at 0.71 μg/mL at 100 μL per test was used for staining.
[b]0.2–0.5 × 10[6] cells in 100 μL were used per test.
[c]100 μL of rsCD4 at 2x the designated concentration was preincubated with 100 μL of the biotinylated B4 for 1 hr at room temperature prior to incubation with the HPB-ALL cells.

EXAMPLE 12

Generation of Human Ig Monoclonal Antibodies Derived from HC1 and/or HC2 Transgenic Mice Immunized with Cells from a CD4-expressing Human T Cell Line This example describes the generation of human hybridomas from mice homozygous for an inactivated endogenous immunoglobulin locus and containing transgene human sequences encoding a human heavy chain and a human light chain. The hybridomas generated from these transgenic mice immunized with a CD4-expressing human T cell line according to the immunization scheme described in Example 3 secrete monoclonal antibodies comprising a human sequence heavy chain and a human sequence light chain. From among these hybridomas are selected clones, according to the algorithm described in Table 12, which secrete antibodies that bind to human host cell antigen complex comprising the CD4 protein with a broad cross-neutralizing activity directed against primary isolates of HIV-1 from all clades and diverse primary isolates of HIV-2 and SIV, and which have similar antibody binding properties to that of monoclonal antibody B4.

TABLE 12

Preferred Immunization and Screening Schemes for Reliable Generation of Hybridomas Secreting Antibodies to Host Cell Antigen Complex Comprising CD4 Effective in Neutralizing HIV-1 Primary Isolates

| Preferred Immunization Scheme | | Screening Scheme |
|---|---|---|
| CD4-expressing T cells (e.g. HPB-ALL or SUP-T1 T cell line), 2–10 × 10[6] [1st immunization: i.p., CFA or PBS; additional boosts: i.p. and/or i.v. (≧4x); PBS] | 1) | Positive by rsCD4 ELISA; |
| | 2) | Positive on CD4-expressing HPB-ALL or SUP-T cells; and |
| | 3a) | Inhibition of HIV-1 primary isolate by MT2 Microplaque Neutralization Assay, or |
| | 3b) | Inhibition of "B4-sCD4" interaction by prior incubation of an individual rsCD4 reactive antibody with HPB-ALL cells followed by staining of the cells with biotinylated-B4 (e.g. Table 8); or |
| | 3c) | Inhibition of B4-rsCD4" interaction by simultaneous incubation of an individual rsCD4 antibody with HRP-conjugated B4 (e.g. Table 9) |

More specifically, a transgenic mouse characterized either as having HC1 or HC2 genotype as described in Smith et al., WO 93/12227, homozygous for a functionally disrupted $J_H$ locus and harboring a transgene capable of rearranging to encode a human sequence heavy chain and a transgene capable of rearranging to encode a human sequence light chain, is immunized with cells from a CD4-expressing human leukemic T cell line, HPB-ALL. Approximately 5–10×10$^6$ cells in 100 μl of PBS are introduced into the mouse via intraperitoneal or, more preferably intravenous or both, injection on Day 0. The immunization is repeated every other week for at least four times with the last immunization performed three days prior to fusion. The spleen is removed and approximately 150×10$^6$ spleen cells are fused to approximately 30×10$^6$ fusion partner cells (P3x63Ag8.653 cell line; ATCC) by standard methods (PEG fusion) according to Kohler and Milstein, *Nature,* 1975, 256:495–97. Multiple fusions on subsequent weeks, each following subsequent biweekly and/or monthly boosts and being three days after a final intravenous boost, can also be performed.

Hybridomas are grown up and supernatants are tested by ELISA for binding to rsCD4 as described in Example 3. Human antibodies are detected with peroxidase conjugated secondary antibodies directed against human immunoglobulins.

Primary hybridomas are single-cell cloned by limiting dilution and assessed for secretion of human monoclonal antibodies reactive with rsCD4. To determine whether these monoclonal antibodies also recognize the host cell antigen complex comprising the CD4 protein, supernatants from rsCD4 reactive clones are tested for reactivity similar to that of B4 with cells from HPB-ALL or SUP-T cell line by indirect immunofluorescence staining.

Good growth and high levels of monoclonal antibody production are also important factors in choosing a clonal hybridoma cell line for development.

Amongst the clones secreting antibodies reactive with both rsCD4, and CD4-expressing cells and which grow well and secrete high levels of antibody, supernatants from these clones are further tested for their neutralizing activity directed against primary isolates of HIV. More specifically, they are tested in an MT2 microplaque neutralization assay as described previously for both 50% or 90% endpoint dilutions beginning at 1:2 dilution against, for example, HIV-1 clade B primary isolate 23135. Only those demonstrating strong HIV-1 neutralizing activity are selected for further subcloning. The selected hybridomas secrete human immunoglobulins with binding activities specific for discontinuous scattered conformational epitopes on a host cell antigen complex comprising CD4 having potent neutralizing activity against primary isolates of HIV and SIV. These human monoclonal antibodies are candidate antibodies for use in pre- and post-exposure prophylaxis of HIV infection.

EXAMPLE 13

Demonstration of the Broad Cross-Clade HIV-1 Neutralizing Activity of an Antibody Directed Against a Host Cell Antigen Complex Comprising CD4

Results

Neutralization activities of the antibodies were compared on laboratory strain MN and on the indicated primary isolates representing HIV-1 clades A, B, C, D, and E. These primary isolates were grown on PBMCs, while HIV-1 MN was grown on H9 cells as described in Example 1. Neutralization assays were by the MT-2 Microplaque method (Example 1) and results are presented in Table 13.

Table 13 compares the cross-clade HIV-1 neutralization activities of the monoclonal antibodies from groups 5, 9, and 15 of Example 4 (Table 3), of the α gp120 CD4-BS monoclonal antibody IgG1 b12 described in Example 1 (Table 2), of the group 6 polyclonal anti-gp120 N-terminal V3 antibody of Example 2 (Table 3), and of a commercially available murine monoclonal anti-gp120 N-terminal V3 antibody with specificity for the N-terminal V3 sequences of most HIV-1 clade B strains, MAb 50.1. MAb 50.1 (Repligen Corporation, Cambridge Mass.) was raised against a synthetic peptide immunogen derived from the gp120 N-terminal V3 loop tip of HIV-1 MN. The epitope recognized by this MAb has been defined as Lys-Arg-Ile-X-Ile-Gly-Pro (Wrin et al., *J Virol,* 1995, 69:39–48).

TABLE 13

Neutralization of HIV-1 Clades A, B, C, D and E Primary Isolates[#]
(MT-2 Microplaque Neutralization Assay)

| Group | Type of | Lab Strain MN H9 | | UGO29 (Clade A) | | 23135 PBL (Clade B) | | BRO14 PBL (Clade B) | | ZIM 748 (Clade C) | | UG266 (Clade D) | | TH036 (Clade E) | |
|---|---|---|---|---|---|---|---|---|---|---|---|---|---|---|---|
| * | Antibodies | 50% | 90% | 50% | 90% | 50% | 90% | 50% | 90% | 50% | 90% | 50% | 90% | 50% | 90% |
| 5 | MAb B4 | 20.4 μg/mL | 66.7 μg/mL | 1.17 μg/mL | 6.76 μg/mL | 0.21 μg/mL | 1.54 μg/mL | 0.19 μg/mL | 1.63 μg/mL | 0.54 μg/mL | 2.82 μg/mL | 2.52 μg/mL | 25.6 μg/mL | 0.54 μg/mL | 3.32 μg/mL |
| 6 | G.P. Ig α N-terminal V3 MN | 0.2 μg/mL | 2.1 μg/mL | — | — | >100 μg/mL | >100 μg/mL | >100 μg/mL | >100 μg/mL | — | — | — | — | — | — |
| 9 | Antibody from gps 1–5 | >100 μg/mL | >100 μg/mL | 1.38 μg/mL | 7.14 μg/mL | 0.51 μg/mL | 0.98 μg/mL | 0.49 μg/mL | 2.52 μg/mL | 0.94 μg/mL | 4.37 μg/mL | 6.76 μg/mL | 50 μg/mL | 0.84 μg/mL | 4.37 μg/mL |
| 15 | Antibody from gps 5 and 6 | 0.2 μg/mL | 1.9 μg/mL | 2.26 μg/mL | 9.43 μg/mL | 0.46 μg/mL | 2.52 μg/mL | 0.67 μg/mL | 3.14 μg/mL | 0.80 μg/mL | 4.61 μg/mL | 3.51 μg/mL | 31.3 μg/mL | 0.94 μg/mL | 4.13 μg/mL |
| IgG1 b12 | mAb α gp120 | — | — | 11.9 μg/mL | 38.5 μg/mL | 16.7 μg/mL | 41.7 μg/mL | >50 μg/mL | >50 μg/mL | >50 μg/mL | >50 μg/mL | 6.94 μg/mL | >50 μg/mL | 50 μg/mL | >50 μg/mL |

TABLE 13-continued

Neutralization of HIV-1 Clades A, B, C, D and E Primary Isolates[#]
(MT-2 Microplaque Neutralization Assay)

| Group | Type of Antibodies[*] | Lab Strain MN H9 50% | Lab Strain MN H9 90% | UGO29 (Clade A) 50% | UGO29 (Clade A) 90% | 23135 PBL (Clade B) 50% | 23135 PBL (Clade B) 90% | BRO14 PBL (Clade B) 50% | BRO14 PBL (Clade B) 90% | ZIM 748 (Clade C) 50% | ZIM 748 (Clade C) 90% | UG266 (Clade D) 50% | UG266 (Clade D) 90% | TH036 (Clade E) 50% | TH036 (Clade E) 90% |
|---|---|---|---|---|---|---|---|---|---|---|---|---|---|---|---|
| MAb 50.1 | mAb α gp120 (N-terminal V3) | 0.004 µg/mL | 0.02 µg/mL | >50 µg/mL | >50 µg/mL | >50 µg/mL | >50 µg/mL | >50 µg/mL | >50 µg/mL | >50 µg/mL | >50 µg/mL | >50 µg/mL | >50 µg/mL | >50 µg/mL | >50 µg/mL |

[*]: Antibody mixture with identical antibody composition as the corresponding groups described in Table 2.
—: Not done
[#]: HIV-1 primary isolates of various clades were kindly provided by WHO Global Program on AIDS.

The unique antibody B4 (group 5) strongly neutralized primary isolates of HIV-1 clades A–E while displaying weaker neutralizing activity against MN, the laboratory adapted strain. Combining B4 with other anti-cellular antibodies and anti-N-terminal V3 only served to dilute B4 neutralizing activity against primary isolates (groups 9 and 15). The other antibody that is effective against primary isolates, IgG1 b12, which binds to the CD4 binding site of gp120, displayed a weaker pattern of cross-clade neutralization for primary isolates than did B4 (group "IgG1 b12"), displaying relatively weak neutralizing activity only for primary isolates of clades A, B, and D. It neutralized only one of two lade B primary isolates. In contrast, the anti-N-terminal V3 antibodies, both MAb 50.1 and polyclonal anti-N-terminal V3 MN (groups 6 and "MAb 50.1") were potently neutralizing for the laboratory adapted strain while there was little neutralization of the primary isolates, including the homotypic lade B primary isolate. Potent neutralization of both the laboratory strain and the primary isolates was obtained only by combining the unique antibody B4 with anti-N-terminal V3 antibody (group 15).

In conclusion, the anti-gp120 N-terminal V3 antibodies displayed preferential neutralization for the laboratory adapted strain while the unique antibody B4 of the invention displayed preferential neutralization for primary isolates of clades A–E. Also, in comparison to the a gp120 CD4-BS antibody, which is one of the few antibodies to been previously shown to have cross-clade neutralizing activity against certain HIV-1 primary isolates, the antibody of the invention was the only one to have displayed strong neutralizing activity across all of the primary isolates representing HIV-1 clades A, B, C, D, and E.

EXAMPLE 14

Demonstration of the HIV-2 and SIV Neutralizing Activity of the Unique Antibody

Specific procedures for the determination of virus neutralization by antibody

D27 Antigen Neutralization Assay

Stocks of titered virus are mixed with serial dilutions of antibody and then used to infect mitogen-stimulated human PBMCs and the infected cells are cultured for five days (Gardner et al., *AIDS Res Hum Retroviruses*, 1995, 11:843–854). Maximal virus infectivity and neutralization is quantitated by determining SIV p27 antigen accumulated by the PBMC cultures by p27 ELISA (Coulter SIV p27 EIA, Coulter Immunology, Hialeah, Fla.). Neutralization activity is expressed as antibody concentrations that resulted in the per cent indicated reductions in p27 accumulation compared to the concentration of p27 in untreated (maximal) cultures.

Infectivity Reduction Assay (IRA)

IRA was performed (White-Scharf et al., *Virology*, 1993, 192:197–206). IRA neutralization determinations are arrived at by varying the viral load used to infect PBMCs, in the presence of a fixed amount of antibody, in this case 10 µg/mL. IRA results are expressed as infectious units >95% inactivated by 10 µg/mL of antibody.

Viruses

HIV-2$_{ROD}$ is a cloned strain grown on H9 cells (NIH AIDS Research and Reference Reagent Program Catalog no. 207). HIV-2$_{287}$, a primary isolate, was obtained from the plasma of an experimentally infected monkey, SIV$_{251}$, SIV$_{239}$, and HIV-1/SIV recombinants SHIV$_{IIIB}$, and SHIV$_{89.6}$ are laboratory strains passaged in human T cell lines, supplied by David Montefiori (Duke University, Durham, N.C.). One stock of SIV$_{251}$ had been passaged in primate PBMCs. Recombinant SHIV$_{IIIB}$, and SHIV$_{89.6}$ are SIV with HIV-1 envelopes derived from the indicated clade B strains of HIV-1.

Results

The experiment shown in Table 14 compares the neutralization activities of B4 (group 5 of Table 3, Example 4) and polyclonal anti-N-terminal V3 MN (group 6 of Table 3) against various isolates of HIV-2, SIV, and recombinant SHIV. Isolate designations are as shown on the table. Neutralization determinations on HIV-2$_{287}$ were by Infectivity Reduction Assay (IRA) (White-Scharf et al., *Virology*, 1993, 192:197–206). IRA results are expressed as infectious units >95% inactivated by 10 µg/mL of antibody. Neutralization activities on HIV-2$_{ROD}$ were determined by MT-2 assay as described in Example 1. Neutralization assays on SIV$_{251}$, SIV$_{239}$, and HIV-1/SIV recombinants SHIV$_{IIIB}$, and SHIV$_{89.6}$ were determined by p27 Antigen Neutralization Assay (Gardner et al., *AIDS Res Hum Retroviruses*, 1995, 11:843) of the infected PBMC cultures to the 50% endpoint, except for one set of neutralization determinations for B4 on PBMC-grown SIV$_{251}$ which were carried out to an 80% endpoint. The 50% and 80% endpoints are the fractions of detectable p27 in antibody-treated cultures compared to untreated cultures.

TABLE 14

Neutralization of SIV, SHIV and HIV-2 by Monoclonal Antibody B4

| Group | Type of Antibodies | HIV-2$_{287}$* PBMC IRA | HIV-2$_{ROD}$# 50% | HIV-2$_{ROD}$# 90% | SIV$_{251}$@ 50% | SIV$_{239}$@ 50% | SHIV@ IIIB 50% | SHIV@ 89.6 50% | SIV$_{251}$@ (huPBMC) 80% |
|---|---|---|---|---|---|---|---|---|---|
| 5 | MAb B4 | 5$^7$ (1.5 logs killed) | 0.7 µg/mL | 8.5 µg/mL | 2.0 µg/mL | 1.3 µg/mL | 0.679 µg/mL | 0.088 µg/mL | 1.0 µg/mL |
| 6 | GP Ig α gp120 N-terminal V3 MN | 5$^{9.5}$ (i.e. 0 log killed) | — | — | — | — | >10.0 µg/mL | >10.0 µg/mL | — |

*By Infectivity Reduction Assay with MAb B4 at 10 µg/mL.
By MT2 Microplaque Neutralization Assay
@By p27 Antigen Neutralization Assay B4 exhibited neutralization for all the HIV-2, SIV, and SHIV strains shown in Table 14. In comparison, neutralization by the anti-N-terminal V3 MN antibody previously shown to be effective on laboratory adapted HIV-1 MN (Examples 1 and 13, Tables 2 and 13) was not evident for either of the SHIV recombinants despite the laboratory adapted status of these recombinant strains. Thus, it is evident that the cross-neutralizing activity of a unique and potently neutralizing antibody that extends to HIV-2 and SIV, whether laboratory adapted or primary isolate, whether grown on T cell lines or PBMCs, is a distinct property of the invention.

This observation shows that the antibodies of the invention can be usefully tested in the SIV rhesus macaque animal infection model and the SIV and HIV-2 pig-tailed macaque animal infection models, to test the antibodies for protective efficacy.

EXAMPLE 15

Demonstration of the Neutralizing Activity of a Unique Antibody for Chimpanzee-Adapted HIV-1

Results

The neutralization activities of the B4 and the previously characterized IgG1 b12 (anti-gp120 CD4 binding site) were compared on an HIV-1 primary field isolate of clade B, HIV-1 DH-12, grown on chimpanzee PBLs and the results presented in Table 15.

Neutralization was determined by both the MT-2 and IRA methods for B4 and only by the IRA method for IgG1 b12. IRA results are expressed as infectious units >95% inactivated by 10 µg/mL of antibody for B4 and as infectious units >95% inactivated by 25 µg/mL of antibody for IgG1 b12.

Comparison of the present MT-2 assay results with results from Tables 3 and 13 (group 5) show that a unique CD4 reactive antibody, B4, displayed comparable neutralizing activity against the chimp-adapted HIV-1 as for the human PBMC-grown primary strains. Comparison of the IRA results suggests that B4 displays more than an order of magnitude more neutralizing activity against chimpanzee-adapted HIV-1 than the anti-gp120 CD4 binding site antibody IgG1 b12. Therefore, an antibody of the invention is distinctly more active against chimpanzee-adapted HIV-1 than is the best of previously known monoclonal antibodies having primary isolate neutralizing activity.

These results indicate that an antibody of the invention can be usefully tested in the chimpanzee in vivo model for HIV-1 infection, to test for protective efficacy.

TABLE 15

Neutralization by MAbs of Chimp PBL-Grown HIV-1 Primary Field Isolate DH-12 (Clade B)

| MAb | DH-12 (Clade B) PBMC IRA* | DH-12 (Clade B) 50% Inhib# | DH-12 (Clade B) 90% Inhib# |
|---|---|---|---|
| MAb B4 | 3.0 logs killed at 10 µg/mL per culture | 0.33 µg/mL | 2.1 µg/mL |
| IgG1 b12 (α gp120) | 1.375 logs killed at 25 µg/mL per culture | — | — |

*by Infection Reduction Assay
by MT-2 Microplaque Assay

EXAMPLE 16

Kinetics of Neutralization by B4 of HIV-1 Primary Isolates

Results

Tables 16 and 17 depict the kinetics of neutralization by B4 on HIV-1 23135, a clade B primary field isolate. Table 16 shows the kinetics of neutralization for two concentrations of B4, 2 and 20 µg/mL, as added during intervals from 0 to 24 hours following addition of virus, using the MT-2 Microplaque Assay. Neutralization is expressed as per cent survival of the indicated virus dilutions. Table 17 depicts the kinetics of neutralization of HIV-1 23135 by 20 µg/mL of B4, as added during a 0 to 96 hour time course following addition of virus to the cells. The extended time course necessitated use of a p24 Antigen Neutralization Assay for the determination of neutralization activity against input virus of the indicated dilutions (Wrin et al., *J Virol*, 1995, 69:39–48). In this p24 assay, serial dilutions of titered virus are used to infect PBMCs and the infected cells are cultured for four days. Antibody is added to the indicated concentrations at the indicated times. Virus infectivity and neutralization is quantitated by determining p24 antigen accumulated by the PBMC cultures by p24 ELISA (Coulter Immunology, Hialeah Fla.). Results are expressed as per cent of detectible p24 in antibody-treated cultures compared to the concentration of p24 in untreated cultures, i.e., the results are equivalent to per cent virus survival by microplaque count although p24 detection is more impacted by background.

Table 16 shows that the B4 completely neutralizes input virus at a concentration of 2 µg/mL up to 1 hour post-infection. At a concentration of 20 μg/mL, the antibody is effective beyond 24 hours. Table 17 shows the results when the time course was extended to 96 hours and shows effective neutralization by 20 μg/mL of B4 for antibody input up to 48 hours post-infection. These results demonstrate that a unique antibody can prevent establishment of in vitro infection even after the cells have been exposed to virus and suggest that such an antibody may be effective for prophylactic treatment following exposure to HIV.

TABLE 16

Kinetics (0–24 hrs) of MAb B4-Mediated Neutralization of HIV Primary Field Isolate 23135 (Clade B) (MT2 Microplaque Neutralization Assay)

| Time of Addition of MAb (Post Virus Inoculation) | Concentration of MAb (μg/mL) | Percent of Virus Survival Virus Dilution | | |
|---|---|---|---|---|
| | | 1:75 | 1:150 | 1:300 |
| 0 | 2 | 0.0 | 0.0 | 0.0 |
| | 20 | 0.0 | 0.0 | 0.0 |
| 0.5 | 2 | 0.0 | 0.0 | 0.0 |
| | 20 | 0.0 | 0.0 | 0.0 |
| 1.0 | 2 | 0.0 | 0.0 | 0.0 |
| | 20 | 0.0 | 0.0 | 0.0 |
| 2.0 | 2 | 4.2 | 1.9 | 2.2 |
| | 20 | 0.0 | 0.0 | 0.0 |
| 6.0 | 2 | 17.2 | 15.9 | 29.2 |
| | 20 | 0.0 | 0.0 | 0.0 |
| 24.0 | 2 | 87.0 | 64.1 | 59.4 |
| | 20 | 0.0 | 0.0 | 0.0 |

TABLE 17

Kinetics (0–96 hrs) of MAb B4-Mediated Neutralization of HIV Primary Field Isolate 23135 (Clade B) (p24 Antigen Neutralization Assay)

| Time of Addition of mAb (post virus inoculation) | Virus Dilution | Avg p24 (pg) (with 20 μg/mL B4) | Avg p24 (pg) (Virus control, without B4) | Percent of Virus Survival |
|---|---|---|---|---|
| 0 hrs | 1:75 | 37 | 2367 | 1.6 |
| | 1:150 | 17 | 1292 | 1.3 |
| | 1:300 | 36 | 922 | 3.9 |
| 24 hrs | 1:75 | 168 | 2499 | 6.7 |
| | 1:150 | 112 | 2061 | 5.4 |
| | 1:300 | 64 | 1626 | 3.9 |
| 48 hrs | 1:75 | 189 | 2230 | 8.5 |
| | 1:150 | 60 | 1845 | 3.3 |
| | 1:300 | 35 | 1125 | 3.1 |
| 72 hrs | 1:75 | 654 | 2220 | 29.5 |
| | 1:150 | 353 | 1994 | 17.7 |
| | 1:300 | 295 | 1565 | 18.8 |
| 96 hrs | 1:75 | 2023 | 1747 | 115.8 |
| | 1:150 | 913 | 2358 | 38.7 |
| | 1:300 | 672 | 1976 | 34.0 |

EXAMPLE 17

Passive Immunization of Rhesus Macaques Against $SIV_{mac251}$ Infection

Specific procedures for determination of protection from SIV infection

The above studies on the neutralizing activity of the antibodies of the present invention characterize the concentration, kinetics, and the extended breadth of B4 for the neutralization of primary isolates of HIV-2 and SIV, as well as primary isolates from all clades of HIV-1. Those in vitro characterizations, together with the high degree of conservation between the CD4 sequences of primate species, suggests a high likelihood for in vivo protective efficacy for the B4 embodiment of the invention against infection by all 3 immunodeficiency viruses. Therefore, the protective efficacy of the invention was evaluated by a challenge trial of B4 against the experimental infection of rhesus macaques with SIV, an excellent animal model for human AIDS.

Virus stock and in vivo SIV challenge

The virus stock used for challenge was the prototype $SIV_{mac251}$ strain obtained from R. Desrosiers (New England Regional Primate Research Center, Southborough Mass.). All challenges were i.v. inoculations with about 10 $AID_{50}$ of the uncloned $SIV_{mac251}$ isolate produced in Rhesus PBMCs (Desrosiers et al., PNAS USA, 1989, 86:6353–6357). Both unimmunized monkeys of the control group were given the same i.v. dose of this virus stock and were found to be persistently infected. The animals were bled periodically post-challenge and monitored for establishment of infection by serological tests for virus antigenemia and seroconversion, and by coculture of PBMCs and plasma for detection of virus.

SIV serological assays

Seroconversion as a result of SIV infection was detected by an enzyme immunoassay (EIA) which is based on an HIV-2 peptide antigen (HIV-1,2 EIA; United Biomedical, Inc., Hauppauge N.Y.) that is cross-reactive for SIV and that can be used to determine an end-point titer for plasma antibodies to the immunodominant amino terminus region (amino acids 588–603) of the SIV transmembrane protein (gp36).

SIV p27 Antigen Assay

An SIV-specific, monoclonal antibody-based antigen capture EIA (Coulter Immunology, Hialeah, Fla.) was used to detect productive virus infection in vitro and in vivo. Positive in vivo results were indicated by values of >0.05 ng/mL for undiluted plasma.

SIV isolation and end-point dilution assays

Rhesus PBMCs were separated from whole blood on Ficoll-Hypaque gradients. Two milliliters of undiluted, clarified plasma or separated PBMCs were added to mitogen-stimulated human PBMCs. Cultures were maintained with RPMI-1640 growth medium containing 10% fetal calf serum (Sigma, St. Louis Mo.), supplemented with 20 U/mL IL-2 and 200 U/mL anti-interferon α (both Collaborative Research, Waltham, Mass.), $2.5 \times 10-2$ mM 2-mercaptoethanol and 2 μg/mL polybrene (both Sigma), and kept at 37° C., 5% $CO_2$. Culture supernatants were assayed twice weekly for up to 4–6 weeks for the presence of p27 antigen. A culture was determined to be positive if supernatant samples from three consecutive dates were positive for p27 antigen (Coulter SIV p27 EIA, Coulter Immunology, Hialeah Fla.). For quantitation of infectious SIV in monkey PBMCs, the PBMCs were serially diluted and similarly cocultured with human PBMCs. Cultures for end-point dilution assays are terminated at day 14 and assayed for p27 antigen.

Design and Methods

Six monkeys used for the study described below were colony-bred adult and young adult rhesus macaques from the TSI Primate Center Mason Laboratories (Worcester Mass.). They were seronegative for antibodies to SIV, SRV-1, SRV-2, SRV-5 and STLV-1. These animals were housed indoors in accordance with American Association for Accreditation of Laboratory Animal Care Standards and the investigators adhered to the Guide for the Care and Use of Laboratory Animals prepared by the Committee on Care and Use of Laboratory animals of the Institute of Laboratory Resources, NRC, Washington D.C. Animals were randomized into control and treatment groups by weight.

The two monkeys of Group 1 were given PBS and the four monkeys in Groups 2 were given 4 mg/kg MAb B4, purified by protein-A affinity column chromatography, by intravenous infusion 1 hr before intravenous viral challenge by 10 AID$_{50}$ of SIV$_{mac251}$.

Results

Blood was collected pre-treatment, pre-challenge, 1 hr, 1, 3, 15, 22, 29 and 36 days post-challenge. The serum level of the anti-CD4/chemokine receptor antibody, determined for all samples by rsCD4 enzyme immunoassay, was found to diminish to half of maximum value 1 day after the infusion, most likely due to penetration by and saturation binding of the monkey CD4-expressing T cells in both peripheral blood and the lymphoid tissues. On days 15, 22 and 29, plasma samples from all monkeys were collected and tested for p27 antigen by the SIV p27 Antigen Assay.

On day 15, both monkeys from the control group (Nos. 170 and 110 of group 1), were found to be infected as demonstrated by positive p27 SIV antigen serology (Table 18). In comparison, by day 15, only 1 (No. G4B) out of the 4 monkeys in the experimental group 2 receiving 4 mg/kg B4 was infected (Table 18).

Subsequently, the plasma samples collected from all monkeys on days 22 and 29 were analyzed by p27 immunoassays. Those results confirmed the status of SIV antigenemia of the monkeys observed on day 15.

Another parameter for evaluation of SIV infection was to monitor the animals immune status for seroconversion to SIV reactivity. Both monkeys in the control group 1 developed anti-SIV antibodies as detected by the HIV 1,2 (SIV) EIA test, beginning 2–3 weeks after the viral challenge (Table 19). Seropositivity was scored as being above a cutoff value of 4 times absorbance of non-reactive control sera (NRC) from non-immunized unchallenged macaques. Seroconversion in Table 19 is shown by underlining. The absorbance from a Strongly Reactive Control (SRC) is shown for reference. The three protected monkeys in experimental group 2 (DW3, GN-terminal V3 and NU3) remained seronegative throughout the period tested. Thus, the only monkey (G4B) from the experimental group found to be infected with SIV by p24 antigenemia was also found to have developed anti-SIV antibodies during this period.

Rhesus PBMCs from each of the 6 monkeys in both groups were also collected on days 15, 22 and 29. Plasma and PBMC specimens from those days were combined with mitogen-stimulated human PBMCs for detection of SIV infection by virus culture. Culture was continued for 3 weeks and supernatants from these co-cultures were assayed for the presence of p27 antigen. Again, both monkeys from the control group (Nos. 170 and 110) and the one non-protected monkey (GB4) from the experimental group were shown to be infected, as evidenced by positive virus culture results from both the PBMC and plasma specimens (Table 18).

Conclusions

These results demonstrated that passive immunization of rhesus macaques with monoclonal antibody B4 at a modest dose (4 mg/kg) effectively protects most (75%) monkeys from infection by an SIV primary isolate, following challenge with a dose of SIV$_{mac251}$, a dose that has effectively caused persistent infection in all historical control animals and in 2 out of 2 control animals in the present study.

TABLE 18

Passive Immunization of Rhesus Macaques with Monoclonal Antibody B4 Followed by Challenge with SIV$_{mac251}$

| Group | Monkey No. | Protected | p27 Antigenemia* (Day 15) | Seroconversion@ | virus Isolation# PBMC (Day 15) | Plasma |
|---|---|---|---|---|---|---|
| Group 1 | 170 | No | Pos (2.21 ng) | Yes (wk 3) | Pos (9.0) | Pos |
| PBS administered 1 hr before 10AID$_{50}$ SIV challenge | 110 | No | Pos (1.43 ng) | Yes (wk 3) | Pos (10.0) | Pos |
| Group 2 | DW3 | Yes | Neg (<0.049 ng) | No | Neg | Neg |
| MAb B4 (4 mg/kg) | G4B | No | Pos (>0.8 ng) | Yes (wk 3) | Pos (8.5, 10.5) | Pos |
| administered i.v. | NU3 | Yes | Neg (<0.049 ng) | No | Neg | Neg |
| 1 hr before 10AID$_{50}$ SIV challenge | GV3 | Yes | Neg (<0.049 ng) | No | Neg | Neg |

*The three animals having positive p27 antigenemia results remained persistently positive throughout the period monitored (up to day 141) and the three protected animals remained persistently negative for the same period monitored.
Coculture by limiting dilution results were obtained with specimens taken from days 15 and 22.
@See Table 19 for actual time course of conversion.

TABLE 19

Seroconversion Status of Rhesus Macaques Following SIV$_{mac251}$ Challenge

| | | Days post viral challenge | | | | | Seroconversion |
|---|---|---|---|---|---|---|---|
| | | 0 | 8 | 15 | 22 | 29 | 43 | status |
| Group 1 | 170 | 0.215 | 0.232 | 0.268 | 2.024 | 2.023 | 2.169 | +wk 3 |
| | 110 | 0.055 | 0.060 | 0.053 | 0.451 | 2.161 | 2.194 | +wk 3 |
| Group 2 | DW3 | 0.060 | 0.065 | 0.058 | 0.064 | 0.063 | 0.053 | — |
| | NU3 | 0.058 | 0.054 | 0.058 | 0.124 | 0.054 | 0.065 | — |
| | G4B | 0.075 | 0.091 | 0.070 | 1.863 | 2.184 | 2.078 | +wk 3 |
| | GV3 | 0.056 | 0.071 | 0.051 | 0.055 | 0.056 | 0.057 | — |

SRC = 0.777  NRC = 0.078  Cutoff = 4 × NRC = 0.312

EXAMPLE 18

Pre- and Postexposure Protection against Primary Isolates of Human Immunodeficiency Virus Infection Mediated by Monoclonal Antibody B4

In support of the concept of immunoprophylaxis against HIV-1 infection, monoclonal antibodies (MAbs) and polyclonal serum have been shown to protect nonhuman primates and human peripheral blood lymphocyte-reconstituted SCID (hu-PBL-SCID) mice from infection with HIV-1 (Emini et al., *J Virol,* 1990, 64:3674; Prince et al., *AIDS Res Hum Retroviruses,* 1991, 7:971; Emini et al., *Nature,* 1992, 355:728; Safrit et al., *AIDS,* 1993, 7:15) and SIV (Putkonen et al., *Nature,* 1991, 352:436; Lewis et al., *Vaccine,* 1993, 11:1347). Those studies using monoclonal or polyclonal antibodies directed against viral antigens were found, however, to neutralize only T-cell line-derived laboratory strains but not primary isolates of immunodeficiency viruses.

In this study, monoclonal antibody B4 was used to determine whether passive immunization by a monoclonal antibody of the present invention, i.e., a monoclonal antibody directed to a discontinuous scattered conformational epitope present on a host cell antigen complex comprising CD4 protein and chemokine receptor and having broad neutralizing activities against all primary isolates of HIV, is protective in vivo against infection caused by an HIV-1 primary isolate. The goal for this study was to demonstrate that administration of B4 can protect mice with severe combined immunodeficiency (SCID) transplanted with normal human peripheral blood leukocytes (hu-PBL), designated hu-PBL-SCID mice, from subsequent challenge with a primary isolate of HIV previously shown to be neutralization resistant. The hu-PBL-SCID mouse model was chosen for this efficacy evaluation because many experimental groups involving multiple animals can be done at reasonable expense in a relatively short time, advantages not offered by the only alternative animal model for HIV-1 challenge-protection studies, the infection by HIV-1 of chimpanzees. Specific procedures for reconstitution of the human immune system in SCID mice and determination of protection from HIV-1 infection MAbs Control antibody used in this study was a murine $IgG_{2a}$, an antibody of unknown binding specificity, secreted by mouse myeloma cell line RPC5.4 (ATCC No. TIB12). Both B4 and the control $IgG_{2a}$ RPC5.4 were purified from ascitic fluids by Protein-A affinity column chromatography and resuspended in sterile PBS at 2 mg/mL prior to use. All antibodies were given to hu-PBL-SCID mice by intraperitoneal (i.p.) injection.

SCID mouse reconstitution

CB.17 scid/scid mice used in this study were maintained under specific pathogen-free conditions. Nonleaky phenotype mice were reconstituted by i.p. injection of $2 \times 10^7$ freshly isolated normal human PBL suspended in 0.5 mL of PBS. Two weeks after PBL injection, reconstitution was confirmed by analysis of mouse sera for the presence of human immunoglobulins by ELISA (SangStat, Menlo Park, Calif.). Only human immunoglobulin-positive mice were used for studies of HIV-1 infection.

Virus stocks

HIV-1 AD6 virus stocks were prepared from the supernatants of infected PBL as described (Ho et al., *N Engl J Med,* 1989, 321:1621–5) and titrated for infectivity in hu-PBL-SCID mice. They are expressed as the 50% mouse infective dose ($MID_{50}$) per milliliter.

Virus neutralization assay

HIV-1 neutralizations were performed by a p24 assay as described (Ho et al., *J Virol,* 1991, 65:489–493). Neutralization was defined as the percent reduction in the amount of p24 antigen released into the culture supernatants from wells treated with antibody compared with control wells not treated with antibody.

Virus challenge of hu-PBL-SCID mice

AD6, known to be resistant to neutralization by most neutralizing antibodies, was selected as the HIV-1 primary isolate in this study. All procedures for infection and maintenance of the hu-PBL-SCID mice were done in a biosafety level 3 animal facility. Infection of hu-PBL-SCID mice was carried out 2 weeks after PBL reconstitution. Mice were injected i.p. with 0.5 mL of diluted cell-free HIV-1 stocks containing 10 $MID_{50}$. The virus inocula were previously determined by titration in hu-PBL-SCID mice and were shown to infect at least 80% of hu-PBL-SCID mice.

Detection of HIV-1 by coculture

Three weeks after viral challenge, the mice were sacrificed and cells were recovered from peritoneal lavage and spleens as described (Safrit et al., *AIDS* 1993, 7:15–21). Then $2 \times 10^5$ peritoneal lavage cells or $5 \times 10^6$ spleen cells from the mice (with 10-fold serial dilutions) were incubated with $2 \times 10^6$ PHA-activated PBL from HIV-1-seronegative human donors in an end-point dilution culture. The cocultures were monitored weekly for the presence of HIV-1 p24 core antigen in the culture supernatant up to 4 weeks. Cultures were considered positive for HIV-1 if a single sample contained >1000 pg/mL or if 2 consecutive samples contained >200 pg/mL p24 antigen. The most highly diluted well containing detectable infected cells was taken as the endpoint, and virus titers were expressed as Tissue Culture Infectious Doses (TCID) per $10^6$ cells.

Dose and kinetic studies for the effectiveness of pre- and post-exposure prophylaxis by MAb B4

EXPERIMENT 1

Design and methods

For evaluation of pre-exposure protection, monoclonal antibody B4 in 0.5 mL PBS was injected intraperitoneally 1 hr before HIV-1 inoculation. Two groups of mice received MAb B4 (Groups 2 and 3, n=6 per group, at a concentration of 50 mg/kg and 5 mg/kg respectively), and one group received the irrelevant mouse $IgG_{2a}$ of myeloma RPC5.4 (Group 1, n=4 at a concentration of 50 mg/kg). The previously immunized mice were then challenged intraperitoneally with 10 $MID_{50}$ of HIV-1 primary isolate AD6.

For evaluation of post-exposure protection, Group 4 animals (n=6) were challenged with the virus and 30 minutes later received B4 at a concentration of 50 mg/kg. Each mouse weighed an average of 20 g. Three weeks after viral challenge the mice were killed and spleen cells and peritoneal lavage were collected for determination of infection by virus culture.

Results

No toxicity by antibody was observed in any group of the animals. As shown in Table 20A, HIV-1 was recovered in cultures carried out to 4 weeks from both splenocytes and peritoneal lavage cells that were cocultured with PHA-activated human PBLs from three (Nos. 4296, 4297 and 4303) out of the four mice in group 1 given 50 mg/kg control $IgG_{2a}$, demonstrating a 75% infectivity rate for this control group. The virus was not recovered from any of the eighteen mice given B4 at either 50 mg/kg (groups 3 and 4) or 5 mg/kg (group 2), administered 1 hr prior to (Groups 2 and 3) or 0.5 hr after the viral challenge (Group 4) (Table 20A).

EXPERIMENT 2

Design and methods

For this post-exposure protection experiment, mice were challenged intraperitoneally with 10 $MID_{50}$ of HIV-1 primary isolate AD6 prior to administration of any antibody. Mice of control Group 1 (n=5) were injected intraperitoneally with a 5 mg/kg dose of mouse $IgG_{2a}$ (RPC5.4) immediately following the HIV-1 challenge. Mice of Group 2 (n=4) were administered 50 mg/kg of MAb B4 immediately following challenge. Two, four and 24 hrs later, Groups 3, 4 and 5 animals (n=4, 4, 5 per group, respectively) received MAb B4 at a concentration of 50 mg/kg; and 1 hr later, Groups 6 and 7 animals (n=4 per group) received MAb B4 at a concentration of 15 mg/kg and 5 mg/kg respectively. Each mouse weighed an average of 20 g. Three weeks after viral challenge, the mice were killed and spleen cells and peritoneal lavage were collected for determination of infection by virus culture.

Results

No toxicity by antibody was observed in any group of the animals. As shown in Table 20B, HIV-1 was recovered in cultures carried out to 4 weeks from both splenocytes and peritoneal lavage cells that were cocultured with PHA-activated human PBLs from three (No. 4467, 4471 and 4473) out of the five mice in group 1 given 5 mg/kg $IgG_{2a}$ (RPC5.4), demonstrating a 60% infectivity rate for this control group. HIV-1 virus was not recovered from any of the twenty-one mice of Groups 2, 3, 4, 6 and 7 which had been given MAb B4 at either 50 mg/kg (groups 2, 3 and 4) 0, 2 or 4 hrs after the viral challenge; or 15 mg/kg (group 6), and 5 mg/kg (Group 7) at 1 hr intervals after the viral challenge for the latter two groups, as shown in Table 20B. HIV-1 was detected by viral culture in two of the four mice of Group 5 (Nos. 4469 and 4472), the group that had received 50 mg/kg of MAb B4 24 hrs after the challenge. However, HIV-1 was recovered from the peritoneal wash only of animal No. 4469 (Table 20B).

EXPERIMENT 3

Design and methods

The post-exposure protection experiments, specifically, were repeated with the lowest B4 concentration (5 mg/kg) tested thus far for a post-exposure period up to 4 hrs. Mice were challenged intraperitoneally with 10 $MID_{50}$ of HIV-1 primary isolate AD6 prior to administration of any antibody. Mice of control Group 1 (n=5) were injected intraperitoneally with a 5 mg/kg dose of mouse $IgG_{2a}$ (RPC5.4) immediately following the HIV-1 challenge. Mice of Group 2 (n=5) were administered 5 mg/kg of MAb B4 immediately following challenge. One, two, and four hrs later, Groups 3, 4 and 5 animals respectively (n=5 per group) received MAb B4 at a concentration of 5 mg/kg. Each mouse weighed an average of 20 g. Three weeks after viral challenge, the mice were killed and spleen cells and peritoneal lavage were collected for determination of infection by virus culture.

Results

No toxicity by antibody was observed in any group of the animals. As shown in Table 20C, HIV-1 was recovered in cultures carried out to 4 weeks for both splenocytes and peritoneal lavage cells that were cocultured with PHA-activated human PBLs from all five mice in group 1 given 5 mg/kg $IgG_{2a}$ (RPC5.4), demonstrating a 100% infectivity rate for this control group. HIV-1 virus was not recovered from any of the twenty mice of Groups 2, 3, 4 and 5 which had been given MAb B4 at 5 mg/kg at 0, 1, 2 or 4 hrs after the viral challenge, as shown by Table 20C.

TABLE 20A

Pre- and Postexposure Prophylaxis of HIV-1$_{AD6}$ Infection in Hu-PBL-SCID mice by MAb B4
Experiment 1

| Experimental Groups | HIV-1 recovery from hu-PBL-SCID mice: WEEK 4 Co-culture | | | |
|---|---|---|---|---|
| | Peritoneal Lavage | Spleen | Culture end-point | TCID/10$^6$ cells |
| 1 Murine IgG$_{2a}$ MAb (RPC5.4) (50 mg/kg dose) | | | | |
| 4296 | + | + | 5 × 10$^3$ | 200 |
| 4297 | + | + | 5 × 10$^5$ | 2 |
| 4299 | − | − | − | <0.2 |
| 4303 | + | + | 5 × 10$^4$ | 20 |
| 2 MAb B4, 1 hr before challenge (5 mg/kg dose) | | | | |
| 4285 | − | − | − | <0.2 |
| 4287 | − | − | − | <0.2 |
| 4290 | − | − | − | <0.2 |
| 4305 | − | − | − | <0.2 |
| 4306 | − | − | − | <0.2 |
| 4311 | − | − | − | <0.2 |
| 3 MAb B4, 1 hr before challenge (50 mg/kg dose) | | | | |
| 4289 | − | − | − | <0.2 |
| 4291 | − | − | − | <0.2 |
| 4295 | − | − | − | <0.2 |
| 4300 | − | − | − | <0.2 |
| 4301 | − | − | − | <0.2 |
| 4302 | − | − | − | <0.2 |
| 4 MAb B4 30 min after challenge (50 mg/kg dose) | | | | |
| 4261 | − | − | − | <0.2 |
| 4284 | − | − | − | <0.2 |
| 4307 | − | − | − | <0.2 |
| 4308 | − | − | − | <0.2 |
| 4310 | − | − | − | <0.2 |
| 4312 | − | − | − | <0.2 |

TABLE 20B

Experiment 2

| Experimental Groups | HIV-1 recovery from hu-PBL-SCID mice: WEEK 4 Co-culture | | | |
|---|---|---|---|---|
| | Peritoneal Lavage | Spleen | Culture end-point | TCID/10$^6$ cells |
| 1 Murine IgG$_{2a}$ (RPC5.4, 5 mg/kg dose), 0 hr after challenge | | | | |
| 4462 | − | − | − | <0.2 |
| 4465 | − | − | − | <0.2 |
| 4467 | + | + | 5 × 10$^5$ | 0.2 |
| 4471 | + | + | 5 × 10$^6$ | 0.2 |
| 4473 | + | + | 5 × 10$^2$ | 2000 |
| 2 MAb B4 (50 mg/kg dose), 0 hr after challenge | | | | |
| 4475 | − | − | − | <0.2 |
| 4486 | − | − | − | <0.2 |

TABLE 20B-continued

Experiment 2

HIV-1 recovery from hu-PBL-SCID mice: WEEK 4
Co-culture

| Experimental Groups | Peritoneal Lavage | Spleen | Culture endpoint | TCID/$10^6$ cells |
|---|---|---|---|---|
| 4488 | – | – | – | <0.2 |
| 4490 | – | – | – | <0.2 |
| 3 MAb B4 (50 mg/kg dose), 2 hrs after challenge | | | | |
| 4500 | – | – | – | <0.2 |
| 4501 | – | – | – | <0.2 |
| 4503 | – | – | – | <0.2 |
| 4505 | – | – | – | <0.2 |
| 4509 | – | – | – | <0.2 |
| 4 MAb B4 (50 mg/kg dose), 4 hrs after challenge | | | | |
| 4476 | – | – | – | <0.2 |
| 4495 | – | – | – | <0.2 |
| 4497 | – | – | – | <0.2 |
| 4506 | – | – | – | <0.2 |
| 4511 | – | – | – | <0.2 |
| 5 MAb B4 (50 mg/kg doae), 24 hr after challenge | | | | |
| 4469 | + | – | – | <0.2 |
| 4472 | + | + | $5 \times 10^4$ | 20 |
| 4474 | – | – | – | <0.2 |
| 4477 | – | – | – | <0.2 |
| 6 MAb B4 (15 mg/kg dose), 1 hr after challenge | | | | |
| 4478 | – | – | – | <0.2 |
| 4481 | – | – | – | <0.2 |
| 4489 | – | – | – | <0.2 |
| 4504 | – | – | – | <0.2 |
| 7 MAb B4 (5 mg/kg dose), 1 hr after challenge | | | | |
| 4485 | – | – | – | <0.2 |
| 4492 | – | – | – | <0.2 |
| 4496 | – | – | – | <0.2 |
| 4499 | – | – | – | <0.2 |

TABLE 20C

Experiment 3
Pre- and Postexposure Prophylaxis of HIV-1$_{AD6}$ Infection in Hu-PBL-SCID mice by MAb B4

HIV-1 recovery from hu-PBL-SCID mice: WEEK 4
Co-culture

| Experimental Groups | Peritoneal Lavage | Spleen | Culture endpoint | TCID/$10^6$ cells |
|---|---|---|---|---|
| 1 Murine IgG$_{2a}$ (RPC 5.4) (5 mg/kg dose), 0 hr after challenge | | | | |
| 4630 | + | + | $5 \times 10^5$ | 2 |
| 4634 | + | + | $5 \times 10^1$ | 20,000 |
| 4647 | + | + | $5 \times 10^1$ | 20,000 |
| 4652 | + | + | $5 \times 10^5$ | 2 |
| 4664 | + | + | $5 \times 10^1$ | 20,000 |
| 2 MAb B4 (5 mg/kg dose), 0 hr after challenge | | | | |
| 4636 | – | – | – | <0.2 |
| 4639 | – | – | – | <0.2 |
| 4640 | – | – | – | <0.2 |
| 4660 | – | – | – | <0.2 |
| 4666 | – | – | – | <0.2 |
| 3 MAb B4 (5 mg/kg dose), 1 hr after challenge | | | | |
| 4643 | – | – | – | <0.2 |
| 4644 | – | – | – | <0.2 |
| 4645 | – | – | – | <0.2 |
| 4646 | – | – | – | <0.2 |
| 4648 | – | – | – | <0.2 |
| 4 MAb B4 (5 mg/kg dose), 2 hrs after challenge | | | | |
| 4642 | – | – | – | <0.2 |
| 4649 | – | – | – | <0.2 |
| 4650 | – | – | – | <0.2 |
| 4653 | – | – | – | <0.2 |
| 4656 | – | – | – | <0.2 |
| 5 MAb B4 (5 mg/kg dose), 4 hrs after challenge | | | | |
| 4651 | – | – | – | <0.2 |
| 4654 | – | – | – | <0.2 |
| 4657 | – | – | – | <0.2 |
| 4658 | – | – | – | <0.2 |
| 4659 | – | – | – | <0.2 |

In summary, results obtained from the above three sequential experiments unequivocally demonstrated that passive immunization with MAb B4 gives complete protection from infection by a representative HIV-1 primary isolate in an in vivo animal model in both pre- and postexposure modes.

Since infection of humans following occupational exposure to HIV-1 is rare, most accidental clinical exposures are estimated to be $\leq 1$ human infective dose. Therefore, protection of humans from infection following occupational exposure to HIV may be obtained with serum antibody concentrations much lower than that used in the present SCID mouse study (the 5 and 50 mg/kg doses of the present Example give rise to peak serum antibody concentrations of >10 μg/mL and >100 μg/mL respectively).

Complete protection against a high dose (10 MID$_{50}$) HIV-1 AD6 infection was observed at concentrations of 5 mg/kg, 15 mg/kg and 50 mg/kg in a pre-exposure mode. Complete protection for an interval of greater than 4 hours and less than 24 hours at 50 mg/kg and at least up to 4 hrs at 5 mg/kg was observed in a post-exposure mode. These observations indicate the utility of the MAb B4 embodiment of the invention for prophylaxis up to 4 hrs after occupational exposure to HIV-1.

EXAMPLE 19

Study of "MAb B4-rsCD4-Chemokine Receptor Domain" Interactions Employing Synthetic Peptides Representing Chemokine Receptor Domains Synthetic chemokine receptor domain peptides Chemokine receptor domain peptides listed in Tables 21 and 22 were synthesized by the Merrifield solid-phase synthesis technique on Applied Biosystems automated peptide synthesizers (Models 430, 431 and 433A) using Fmoc chemistry. After complete assembly of the desired peptide, the resin was treated according to standard procedure using trifluoroacetic acid to cleave the peptide from the resin and deblock the protecting groups on the amino acid side chains. Peptides marked by ‡ also contain a gly—gly spacer and a T cell helper epitope from hepatitis B virus (HBV). The cleaved, extracted and washed peptides were purified by HPLC and characterized by mass spectrometry and reverse phase HPLC.

Quantitation of "MabB4-rsCD4-chemokine receptor domain" interactions by respective ELISAs The respective ELISAs were performed essentially as the rsCD4 ELISA described herein (Example 3) except for the antigen coating step, where microtiter wells were coated overnight at 4° C. with various concentrations (0, 0.016, 0.063, 0.25, 1 and 4 μg/mL) of the designated chemokine receptor domain peptide as shown in Table 22, which had been preincubated with 0.25 μg/mL of rsCD4.

Results

No interaction between MAb B4 (at concentrations of 10, 1, 0.1 and 0.01 μg/mL) and any of the individual chemokine receptor domain peptides was detected as measured by the respective ELISA where microwells were coated for 1 hr at 37° C. with the designated chemokine receptor domain peptide at 5 μg/mL in the absence of rsCD4.

TABLE 22

Structural Description of Peptides Representing the Respective Chemokine Receptor Domain as Shown in "MAb B4-rsCD4" Bind Study

| Type of chemokine receptor | | Peptide codes representing the respective chemokine receptor domain | | | |
|---|---|---|---|---|---|
| | | 1 | 2 | 3 | 4 |
| α | IL8Rα | 2007 | 2008 | 2029a | 2030a |
| | IL8Rβ | 2011 | 2012 | 2031a | 2032a |
| | C5a-R | 2033 | 2034a | 2035a | 2036a |
| β | CC-CKR1 | 1999 | 2004 | 2027a | 2028a |
| | CC-CKR2b | 2086b | 2087a | 2088a | 2089a |
| | CC-CKR3 | 2079b | 2086a | 2081a | 2082a |
| | CC-CKR5 | 2045 | 2046 | 2047a | 2048a |
| | Fusin (LESTR) | 1987 | 1988a | 1990 | 1991a |

Only a marginal reactivity between MAb B4 and rsCD4 was detected as measured by the rsCD4 ELISA where microtiter wells were coated with rsCD4 alone at 0.25 μg/mL at 4° C. for overnight.

However, when rsCD4 (at 0.25 μg/mL) was preincubated with various concentrations of each designated chemokine domain peptide, varying patterns of MAb B4 binding to rsCD4 as measured by the respective ELISA $OD_{492}$ readings were observed. Prior interaction of rsCD4 with certain chemokine receptor domain peptides (e.g. CC-CKR2b domains 2 and 3, CC-CKR5 domain 3, and CC-CKR3 domain 4) significantly contributed to the binding of rsCD4 to MAb B4. Such enhancement is peptide concentration dependent. This trend of enhanced "MAb B4-rsCD4" interaction was consistently observed at all MAb B4 concentrations of 10, 1, 0.1 and 0.01 μg/mL.

The degree of enhancement, as measured by the increase in $OD_{492}$ of MAb B4-rsCD4 binding, was calculated for the most optimal concentration for the respective chemokine receptor domain peptide, generally at 1 μg/mL, when compared with MAb B4 binding to rsCD4 at 0.25 μg/mL alone.

TABLE 21

Chemokine Receptor Domain Peptides Employed for "mAb-rsCD4-Chemokine Receptor Domain" Interaction Study

| Peptide Antigen* | | Peptide Antigen* | | Peptide Antigen* | | Peptide Antigen* | |
|---|---|---|---|---|---|---|---|
| Code | Description | Code | Description | Code | Description | Code | Description |
| p1987# | LESTR (1–38)-GG-HBVTh | p2011# | IL8Rβ(1–46)-GG-HBVTh | p2033# | C5a-R (1–32)-GG-HBVTh | p2048a | CC-CKRS (261–277) |
| p1988# | LESTR (106–111) | p2012# | IL8Rβ(106–120)-GG-HBVTh | p2034a | C5a-R (91–116) | p2079b# | CC-CKR3 (1–35)-GG- |
| p1990# | LESTR (181–203)-GG-HBVTh | p2027a | CC-CKR1(168–203) | p2035a | C5a-R (171–205) | p2080a | CC-CKR3 (92–107) |
| p1991# | LESTR (262–285) | p2028a | CC-CKR1(261–287) | p2036a | C5a-R (261–286) | p2081a | CC-CKR3 (173–204) |
| p1999# | CC-CKR1(1–34)-GG-HBVTh | p2029a | IL8Rα(168–203) | p2041a | LESTR (103–114) | p2082a | CC-CKR3 (265–281) |
| p2004# | CC-CKR1(94–107)-GG-HBVTh | p2030a | IL8Rα(259–296) | p2045# | CC-CKR5 (1–29)-GG-HBVTh | p2086b# | CC-CKR2b (1–43)-GG-HBVTh |
| p2007# | IL8Rα(1–39)-GG-HBVTh | p2031a | IL8Rβ(179–208) | p2046a | CC-CKR5 (88–102) | p2087a | CC-CKR2b (100–114) |
| p2008# | IL8Rα(100–111)-GG-HBVTh | p2032a | IL8Rβ(270–302) | p2047a | CC-CKRS (168–199) | p2088a | CC-CKR2b (182–207) |
| | | | | | | p2089a | CC-CKR2b (269–285) |

: HBVTh (FFLLTRILTIPQSLD) represents peptide segment with promiscuous T helper function derived from HBsAg protein.
GG: (Gly—Gly) as spacer residues inserted in between the chemokine receptor domain and the T helper epitope.
*: Chemokine receptor external domain peptide antigens were designed according to the numbering system of the amino acid sequences deduced from the nucleic acid sequences for:
HuLESTR, IL8Rα, IL8Rβ (Loetscher et al, J. Biol. Chem. 1994, 269: 232)
CC-CKR1, CC-CKR2b, CC-CKR3, CC-CKRS (Samson et al, Biochemistry 1996, 35, 3362)
C5a-R (Grotzinger et al, Protein Engineering 1991, 4: 767)

It was graded from 0 to 8 based on the respective % of signal increase for the most optimal MAb B4 concentration at 0.1 μg/mL as shown below in Table 23.

Table 23 summarizes the contributions to MAb B4 binding by all four external domains of eight chemokine receptors. As shown in Table 23, MAb B4 binding to rsCD4 was enhanced by several chemokine receptor domain peptides which signals a promiscuous nature for the CD4 conformation as it is perturbed by contact with various CO-receptors. For a molecule like CD4 involved with multiple immunoregulatory functions, it is reasonable to assume such a dynamic nature for its exposed surface. This finding also explains the difficulty in the mapping of the epitope recognized by MAb B4. It is characterized as a discontinuous and scattered epitope which cannot be readily depicted by the linear or discontinuous sites presented by the various CD4 peptides shown in Table 4. It is further characterized here by the data of Table 23 to also involve sites presented by the various chemokine receptor peptides shown in Table 22. In summary, the B4 recognition site is a highly scattered conformational epitope comprising sites from CD4 in contact with chemokine receptor, a co-receptor, for HIV, and this epitope is critical for HIV binding to host cells and/or HIV entry as reflected by its status as a target for post-exposure viral neutralization.

TABLE 23

Enhancement of MAb B4-rsCD4 Binding by Chemokine Receptor Domains

| | Type of chemokine receptor | Degree of enhancement by respective receptor domain 1 | 2 | 3 | 4 |
|---|---|---|---|---|---|
| α | IL8Rα | 0 | 0 | 3+ | 1+ |
| | IL8Rβ | 0 | 0 | 0 | 1+ |
| | C5a-R | 2+ | 2+ | 2+ | 0 |
| β | CC-CKR1 | 0 | 2+ | 0 | 0 |
| | CC-CKR2b | 3+ | 4+ | 5+ | 0 |
| | CC-CKR3* | 3+ | 1+ | 2+ | 8+ |
| | CC-CKR5 | 0 | 2+ | 5+ | 0 |
| | Fusin (LESTR) | 1+ | 2+ | 0 | 0 |

Degree of enhancement @ peptide conc. of 1 μg/mL:
* @ 4 μg/mL

| | | | |
|---|---|---|---|
| 0–50% | 0 | 250–300 | 5+ |
| 50–100 | 1+ | 300–350 | 6+ |
| 100–150 | 2+ | 350–400 | 7+ |
| 150–200 | 3+ | >400 | 8+ |
| 200–250 | 4+ | | |

EXAMPLE 20

Studies on rsCD4 and Chemokine Receptor Interactions and Monoclonal Antibody Affinity Improved affinity of rsCD4 for anti-CD4 neutralizing antibodies by chemokine receptor CC-CKR5 domain 3 peptide Table 23 shown in Example 19 revealed significant degrees of enhancement of "MAb B4-rsCD4" binding by CC-CKR2b (domains 2 and 3) of >4+, by CC-CKR3 (domain 4) of 8+ and by CC-CKR5 (domain 3) of 5+, whereas only marginal enhancement was affected by peptides corresponding to domains of CXC-CKR4 (also termed fusin or LESTR).

Recently, Feng et al. (*Science,* 1996, 272:872) reported that the receptor CXC-CKR4 was the co-receptor responsible for the efficient entry of T-tropic HIV-1 strains into target cells whereas a series of follow-up reports (Doranz et al., *Cell,* 1996, 85:1149; Dragic et al., *Nature,* 1996, 381:667; Choe et al. *Cell,* 1996, 85:1135; Deng et al., *Nature,* 1996, 381:661; Alkhatib et al., *Science,* 1996, 272:1955) documented that the β-chemokine receptors CC-CKR5, CC-CKR2b and CC-CKR3 were the co-receptors for M-tropic HIV-1, the primary isolates responsible for the establishment of infection.

As shown by Group 5 in Table 13, MAb B4 was found to be more effective in neutralizing primary field isolates of all clades than the T-tropic laboratory strain MN H9. It was therefore relevant to examine the association or lack thereof between improvements to the affinity of anti-CD4 antibodies for rsCD4 as contributed by a chemokine receptor peptide and primary field isolate neutralizing activities. Peptide 2047a representing domain 3 of CC-CKR5, a co-receptor for primary field isolates of HIV of the M-tropic type, and four anti-CD4 monoclonal antibodies at a concentration of 0.1 μg/mL with MAbs B4 and M2 having neutralizing activity and MAbs E6 and J33 lacking thereof were employed for this enhancement study.

As shown in FIG. 4, only the two neutralizing antibodies (i.e., MAbs B4 and M2) demonstrated significant enhancement of "MAb-rsCD4" binding by peptide 2047a in a dose dependent fashion. This enhancement was most optimal when 1 μg/mL peptide 2047a was preincubated with 0.25 μg/mL rsCD4.

Quantitation of the enhanced affinity of MAb B4 for the rsCD4/chemokine receptor CC-CKR5 domain 3 peptide mixture over rsCD4 alone ELISA inhibition assays rsCD4-induced inhibition of MAb B4 binding was performed on microtiter plates coated with rsCD4 (0.25 μg/mL) or rsCD4 (0.25 μg/mL) preincubated with CC-CKR5 domain 3(D3) peptide 2047a (1 μg/mL). Endpoint binding concentrations for MAb B4 on rsCD4 and rsCD4/CC-CKR5-D3 coated microtiter wells were predetermined as 2 μg/mL and 0.1 μg/mL respectively, based on the concentrations of MAb B4 that provide $OD_{492\ nm}$ readings of 1.0 on the respective microtiter wells. Inhibition of mAb B4 binding to the respectively coated microtiter wells was then measured by preincubating diluted samples of rsCD4 ranging from 0 to 10 μg/mL with MAb B4 at the predetermined MAb B4 endpoint concentrations (i.e., 2 μg/mL for rsCD4-coated wells and 0.1 μg/mL for rsCD4/CC-CKR5-D3 coated wells) for 1 hr at 37° C. followed by the standard rsCD4 ELISA procedure described herein in Example 3.

The rsCD4 concentrations giving rise to 50% inhibition (i.e. $IC_{50}$) of MAb B4-rsCD4 and MAb B4-rsCD4/CC-CKR5-D3 binding were 0.72 μg/mL and 0.047 μg/mL in the presence of respective MAb B4 concentration of 2 μg/mL and 0.1 μg/mL, as shown in FIG. 5. Thus, the improved affinity of MAb B4 for rsCD4 mixed with CC-CKR5-D3 (peptide 2047a) over that of MAb B4 for rsCD4 alone can be quantitated as a 15-fold improvement.

EXAMPLE 21

Monoclonal Antibody Directed Against a Host Cell Antigen Complex Comprising CD4 Developed Through Immunization of CD1 Mice with SUP-T SUP-T cells (NIH AIDS Research and Reference Reagent Program Catalog No. 100), a human lymphoma-derived T-cell line, were used to immunize CD1 mice. The initial administration was of $10\times10^6$ cells in Complete Freunds Adjuvant, delivered intraperitoneally. This was followed by multiple boosts of $5–10\times10^6$ cells administered intraperitoneally on a biweekly schedule, as described in Example 3. The last two boosts were given with Complete Freunds and Incomplete Freunds. Otherwise, the boosts were of washed cells delivered in phosphate-buffered-saline (PBS). Splenectomies were performed following the final immunization. Mononuclear splenocytes were prepared, fused to NS-1 mouse myeloma cells, hybridomas were obtained and cloned as described in Example 3.

Hybridoma supernatants were then screened for reactivity by rsCD4 ELISA, and for enhanced reactivity on an rsCD4/p2047a ELISA. Peptide 2047a (p2047a) is the CC-CKR5 domain 3 peptide described in Examples 19, 20 and Table 21. The rsCD4/p2047a ELISA was performed in microtiter wells coated with rsCD4 at 0.25 µg/mL and p2047a at 1 µg/mL, as optimized in Example 20. One of the hybridomas secreted antibodies, designated as B13, which displayed an $A_{492}$ of 0.353 on the rsCD4 ELISA and an $A_{492}$ of 1.526 by rsCD4/p2047a ELISA. That is, B13 displayed enhanced rsCD4/p2047a reactivity as compared to rsCD4 reactivity by ELISA. Hybridoma B13 was then subjected to 10 further cycles of subcloning by dilution and screening. Each cycle yielded clones that secreted rsCD4 reactive monoclonal antibody with enhanced rsCD4/p2047a reactivity by ELISA. Monoclonal antibody B13 (MAb B13) was characterized as belonging to isotype IgG2a, the same isotype as MAb B4.

MAb B13 was further analyzed by the competitive indirect immunofluorescence assay described in Example 11 to demonstrate the ability of B13 to inhibit the binding of MAb B4 to the host cell antigen complex comprising CD4. Biotinylated MAb B4 was incubated with SUP-T target cells that had been preincubated either with a B13 supernatant or mouse anti-CD4 antiserum. Control cells were stained to an FITC staining intensity of 3+ at a positive rate of 95%. In contrast, greater than 95% of the SUP-T cells were stained to an intensity of 1.5 to 2.0 following preincubation in anti-CD4, and no staining of cells was observed following preincubation with B13 supernatant. It can be concluded that like MAb B4, B13 binds specifically with the host cell antigen complex comprising CD4.

The similarity of MAb B13 to MAb B4 was also demonstrated by a comparison of neutralizing activity against primary HIV-1 isolates of diverse clades. Neutralization activities of MAb B13 were compared with those of MAb B4 on primary isolates representing HIV-1 clades A, B, C, D, and E. Viruses, host cells, and the MT-2 Microplaque Neutralization Assay were as described in Example 13. The similarity between the cross-clade neutralization activities of B13 and B4 are shown in Table 24.

TABLE 24

Neutralization of HTV-1 Primary Isolates of Clades A, B, C, D, E by MAb B13 (MT-2 Microplaque Neutralization Assay)

| | Neutralization Activity (µg/mL) | | | | | | | | | | | |
|---|---|---|---|---|---|---|---|---|---|---|---|---|
| | UG 029 PBL (Clade A) | | 23135 PBL (Clade B) | | ZIM 748 (Clade C) | | UG 046 (Clade D) | | UG 266 PBL (Clade D) | | TH 036 PBL (Clade E) | |
| Antibody | 50% | 90% | 50% | 90% | 50% | 90% | 50% | 90% | 50% | 90% | 50% | 90% |
| MAb B13 | 1.07 | 4.35 | 0.42 | 1.2 | 0.12 | 0.76 | 1.23 | 10.5 | 1.5 | 14.3 | 0.3* | 0.6* |
| MAb B4 | 0.45 | 0.78 | 0.13 | 0.35 | 0.12 | 0.25 | 0.28 | 3.73 | 0.65 | 10.2 | 0.08* | 0.5* |

*Input virus for Th 036 was low. This generally gives an apparent higher neutralization activity than would have been obtained had input virus been comparable to the others. Therefore, these results are a qualitative demonstration of neutralization activity against TH 036 and should not be compared quantitatively to the results for the other HIV-1 isolates.

I claim:

1. A process for producing an antibody to a host cell antigen complex comprising CD4/chemokine receptor comprising:
    a. Using as the immunogen CD4-expressing T cells selected from the group consisting of:
        i. normal T lymphocytes selected from the group consisting of peripheral blood mononuclear T cells, thymocytes and splenocytes; and
        ii. lymphoma or leukemia-derived T cell line cells selected from the group consisting of SUP-T and HPB-ALL;
    b. Separating out and washing the CD4-expressing T cells in PBS;
    c. Immunizing intraperitoneally an animal selected from the group consisting of BALB/c mice, CD1 mice, transgenic mice, rats, or rhesus monkeys with 5–10× $10^6$ of the separated and PBS-washed T cells in PBS or complete Freund's adjuvant, followed by multiple intraperitoneal boosts at weekly or bi-monthly intervals with 5–10×$10^6$ separated and PBS-washed T cells without adjuvant for a total of three to six months, with the last boost administered intravenously three days prior to fusion to form hybridomas;
    d. Testing the serum of the immunized animal for the presence of antibodies that bind to rsCD4;
    e. Performing splenectomy on the immunized animal the serum of which tested positive in step d to obtain splenocytes;
    f. Fusing the splenocytes to cells of an immortal malignant cell line to form hybridomas, cloning the hybridomas and selecting the hybridomas secreting antibodies, which have the following characteristics:
        i. Binding to rsCD4;
        ii. Binding to HPB-ALL cells in an immunofluorescence assay where the binding pattern is in the shape of "caps" when examined with a high resolution fluorescence microscope;
        iii. Blocking the binding of HIV gp120 to CD4-expressing cells;
        iv. Binding to CD4-expressing cells previously bound with HIV gp120; and
        v. Neutralizing HIV primary isolates in an in vitro microplaque assay at a concentration of <10 μg/mL for 50% neutralization and 0.1–35 μg/mL for 90% neutralization.

2. A process according to claim 1 wherein neutralization of HIV primary isolates in an in vitro microplaque assay is at a concentration of 0.01–10 μg/mL for 50% neutralization.

3. A process according to claim 1 or 2 wherein the characteristics of the secreted antibodies further comprise
    vi. Providing passive immunity from infection by primary isolates of HIV or SIV to primates or hu-PBL/SCID mice, at an $ED_{50}$ of <50 mg/kg.

4. A process according to claim 2 wherein the characteristics of the secreted antibodies further comprise
    viii. Preferential binding to rsCD4/chemokine receptor over rsCD4.

5. A process according to claim 4 wherein the chemokine receptor is the CC-CKR5 chemokine receptor.

6. A process according to claim 5 wherein the CC-CKR5 chemokine receptor is represented by a CC-CKR5 Domain 3 peptide.

7. A process according to claim 1 or 2 wherein the CD4-expressing cells are SUP-T cells.

8. A process according to claim 3 wherein the CD4-expressing cells are SUP-T cells.

9. A process according to claim 4 wherein the CD4-expressing cells are SUP-T cells.

10. A process according to claim 5 wherein the CD4-expressing cells are SUP-T cells.

11. A process according to claim 6 wherein the CD4-expressing cells are SUP-T cells.

12. A process according to claim 1 or 2 wherein the CD4-expressing cells are HPB-ALL cells.

13. A process according to claim 2 wherein the CD4-expressing cells are HPB-ALL cells.

14. A process according to claim 4 wherein the CD4-expressing cells are HPB-ALL cells.

15. A process according to claim 5 wherein the CD4-expressing cells are HPB-ALL cells.

16. A process according to claim 6 wherein the CD4-expressing cells are HPB-ALL cells.

17. A process according to claim 1 or 2 wherein the animal is BALB/c or CD1 mice.

18. A process according to claim 3 wherein the animal is BALB/c or CD1 mice.

19. A process according to claim 4 wherein the animal is BALB/c or CD1 mice.

20. A process according to claim 5 wherein the animal is BALB/c or CD1 mice.

21. A process according to claim 6 wherein the animal is BALB/c or CD1 mice.

22. A process according to claim 1 or 2 wherein the animal is a transgenic mouse containing transgenic human sequences encoding a human heavy and a human light chain.

23. A process according to claim 3 wherein the animal is a transgenic mouse containing transgenic human sequences encoding a human heavy and a human light chain.

24. A process according to claim 4 wherein the animal is a transgenic mouse containing transgenic human sequences encoding a human heavy and a human light chain.

25. A process according to claim 5 wherein the animal is a transgenic mouse containing transgenic human sequences encoding a human heavy and a human light chain.

26. A process according to claim 6 wherein the animal is a transgenic mouse containing transgenic human sequences encoding a human heavy and a human light chain.

27. An antibody produced by the process according to claim 1 having the following characteristics:
   i. Binding to rsCD4;
   ii. Binding to HPB-ALL cells in an immunofluorescence assay where the binding pattern is in the shape of "caps" when examined with a high resolution fluorescence microscope;
   iii. Blocking the binding of HIV gp120 to CD4-expressing cells;
   iv. Binding to CD4-expressing cells previously bound with HIV gp120; and
   v. Neutralizing HIV primary isolates in an in vitro microplaque assay at a concentration of <10 μg/mL for 50% neutralization and 0.1–35 μg/mL for 90% neutralization.

28. An antibody produced by the process according to claim 27 wherein neutralization of HIV primary isolates in an in vitro microplaque assay is at a concentration of 0.01–10 μg/mL for 50% neutralization.

29. An antibody produced by the process according to claim 27 or 28 wherein the characteristics of the secreted antibodies further comprise
   vi. Providing passive immunity from infection by primary isolates of HIV or SIV to primates or hu-PBL/SCID mice, at an $ED_{50}$ of <50 mg/kg.

30. An antibody produced by the process according to claim 29 wherein the characteristics of the secreted antibodies further comprise
   viii. Preferential binding to rsCD4/chemokine receptor over rsCD4.

31. An antibody produced by the process according to claim 30 wherein the chemokine receptor is CC-CKR5.

32. An antibody produced by the process according to claim 31 wherein the chemokine receptor is represented by a CC-CKR5 D3 peptide.

33. A hybridoma secreting an antibody of claim 27.
34. A hybridoma secreting an antibody of claim 28.
35. A hybridoma secreting an antibody of claim 29.
36. A hybridoma secreting an antibody of claim 30.
37. A hybridoma secreting an antibody of claim 31.
38. A hybridoma secreting an antibody of claim 32.

39. An antibody having the following characteristics:
   i. Binding to rsCD4;
   ii. Binding to HPB-ALL cells in an immunofluorescence assay where the binding pattern is in the shape of "caps" when examined with a high resolution fluorescence microscope;
   iii. Blocking the binding of HIV gp120 to CD4-expressing cells;
   iv. Binding to CD4-expressing cells previously bound with HIV gp120; and
   v. Neutralizing HIV primary isolates in an in vitro microplaque assay at a concentration of <10 μg/mL for 50% neutralization and 0.1–35 μg/mL for 90% neutralization.

40. An antibody according to claim 39 wherein neutralization of HIV primary isolates in an in vitro microplaque assay is at a concentration of 0.01–10 μg/mL for 50% neutralization.

41. An antibody according to claim 39 or 40 further characterized by:
   vi. Providing passive immunity from infection by primary isolates of HIV or SIV to primates or to hu-PBL/SCID mice, at an $ED_{50}$ of <50 mg/kg.

42. An antibody according claim 41 further characterized by:
   viii. Preferential binding to rsCD4/chemokine receptor over rsCD4.

43. An antibody according to claim 42 wherein the chemokine receptor is CC-CKR5.

44. An antibody according to claim 43 wherein the CC-CKR5 chemokine receptor is represented by a CC-CKR5 D3 peptide.

45. A hybridoma secreting an antibody of claim 39 or 40.
46. A hybridoma secreting an antibody of claim 41.
47. A hybridoma secreting an antibody of claim 42.
48. A hybridoma secreting an antibody of claim 43.
49. A hybridoma secreting an antibody of claim 44.

50. A pharmaceutical preparation comprising an antibody according to claim 39 or 40.
51. A pharmaceutical preparation comprising an antibody according to claim 41.
52. A pharmaceutical preparation comprising an antibody according to claim 42.
53. A pharmaceutical preparation comprising an antibody according to claim 43.
54. A pharmaceutical preparation comprising an antibody according to claim 44.

55. A chimeric antibody wherein the variable binding region is obtained from an antibody having the following characteristics:

i. Binding to rsCD4;
ii. Binding to HPB-ALL cells in an immunofluorescence assay where the binding pattern is in the shape of "caps" when examined with a high resolution fluorescence microscope;
iii. Blocking the binding of HIV gp120 to CD4-expressing cells;
iv. Binding to CD4-expressing cells previously bound with HIV gp120; and
v. Neutralizing HIV primary isolates in an in vitro microplaque assay at a concentration of <10 μg/mL for 50% neutralization and 0.1–35 μg/mL for 90% neutralization.

56. A chimeric antibody according to claim 55 wherein neutralization of HIV primary isolates in an in vitro microplaque assay is at a concentration of 0.01–10 pg/mL for 50% neutralization.

57. A chimeric antibody according to claim 55 or 56 further characterized by:
vi. Providing passive immunity from infection by primary isolates of HIV or SIV in primates or in hu-PBL/SCID mice, at an $ED_{50}$ of <50 mg/kg.

58. A chimeric antibody according to claim 57 wherein the antibody is further characterized by:
viii. Preferential binding to rsCD4/chemokine receptor over rsCD4.

59. A chimeric antibody according to claim 58 wherein the chemokine receptor is CC-CKR5.

60. A chimeric antibody according to claim 1 wherein the CC-CKR5 chemokine receptor is represented by a CC-CKR5 D3 peptide.

61. A humanized antibody wherein the variable binding region is obtained from an antibody having the following characteristics:
i. Binding to rsCD4;
ii. Binding to HPB-ALL cells in an immunofluorescence assay where the binding pattern is in the shape of "caps" when examined with a high resolution fluorescence microscope;
iii. Blocking the binding of HIV gp120 to CD4-expressing cells;
iv. Binding to CD4-expressing cells previously bound with HIV gp120; and
v. Neutralizing HIV primary isolates in an in vitro microplaque assay at a concentration of <10 μg/mL for 50% neutralization and 0.1–35 μg/mL for 90% neutralization.

62. A humanized antibody according to claim 61 wherein neutralization of HIV primary isolates in an in vitro microplaque assay is at a concentration of 0.01–10 μg/mL for 50% neutralization.

63. A humanized antibody according to claim 61 or 62 further characterized by:
vi. Providing passive immunity from infection by primary isolates of HIV or SIV in primates or in hu-PBL/SCID mice, at an $ED_{50}$ of <50 mg/kg.

64. A humanized antibody according to claim 62 wherein the antibody is further characterized by:
viii. Preferential binding to rsCD4/chemokine receptor over rsCD4.

65. A humanized antibody according to claim 64 wherein the chemokine receptor is CC-CKR5.

66. A humanized antibody according to claim 65 wherein the CC-CKR5 chemokine receptor is represented by a CC-CKR5 D3 peptide.

67. A humanized antibody according to claim 61 or 62 produced recombinantly.

68. A humanized antibody according to claim 63 produced recombinantly.

69. A humanized antibody according to claim 64 produced recombinantly.

70. A humanized antibody according to claim 65 produced recombinantly.

71. A humanized antibody according to claim 66 produced recombinantly.

72. A fragment of an antibody according to claim 27 or 28 wherein the fragment is selected from the group consisting of Fab', F(ab')$_2$ and F(v).

73. A fragment of an antibody according to claim 29 wherein the fragment is selected from the group consisting of Fab', F(ab')$_2$ and F(v).

74. A fragment of an antibody according to claim 30 wherein the fragment is selected from the group consisting of Fab', F(ab')$_2$ and F(v).

75. A fragment of an antibody according to claim 31 wherein the fragment is selected from the group consisting of Fab', F(ab')$_2$ and F(v).

76. A fragment of an antibody according to claim 32 wherein the fragment is selected from the group consisting of Fab', F(ab')$_2$ and F(v).

77. A fragment of an antibody according to claim 39 wherein the fragment is selected from the group consisting of Fab', F(ab')$_2$ and F(v).

78. A fragment of an antibody according to claim 40 wherein the fragment is selected from the group consisting of Fab', F(ab')$_2$ and F(v).

79. A fragment of an antibody according to claim 41 wherein the fragment is selected from the group consisting of Fab', F(ab')$_2$ and F(v).

80. A fragment of an antibody according to claim 42 wherein the fragment is selected from the group consisting of Fab', F(ab')$_2$ and F(v).

81. A fragment of an antibody according to claim 43 wherein the fragment is selected from the group consisting of Fab', F(ab')$_2$ and F(v).

82. A fragment of an antibody according to claim 44 wherein the fragment is selected from the group consisting of Fab', F(ab')$_2$ and F(v).

83. A fragment of an antibody according to claim 55 wherein the fragment is selected from the group consisting of Fab', F(ab')$_2$ and F(v).

84. A fragment of an antibody according to claim 56 wherein the fragment is selected from the group consisting of Fab', F(ab')$_2$ and F(v).

85. A fragment of an antibody according to claim 57 wherein the fragment is selected from the group consisting of Fab', F(ab')$_2$ and F(v).

86. A fragment of an antibody according to claim 58 wherein the fragment is selected from the group consisting of Fab', F(ab')$_2$ and F(v).

87. A fragment of an antibody according to claim 59 wherein the fragment is selected from the group consisting of Fab', F(ab')$_2$ and F(v).

88. A fragment of an antibody according to claim 60 wherein the fragment is selected from the group consisting of Fab', F(ab')$_2$ and F(v).

89. A fragment of an antibody according to claim 61 wherein the fragment is selected from the group consisting of Fab', F(ab')$_2$ and F(v).

90. A fragment of an antibody according to claim 62 wherein the fragment is selected from the group consisting of Fab', F(ab')$_2$ and F(v).

91. A fragment of an antibody according to claim 63 wherein the fragment is selected from the group consisting of Fab', F(ab')$_2$ and F(v).

92. A fragment of an antibody according to claim 64 wherein the fragment is selected from the group consisting of Fab', F(ab' )$_2$ and F(v).

93. A fragment of an antibody according to claim 65 wherein the fragment is selected from the group consisting of Fab', F(ab' )$_2$ and F(v).

94. A fragment of an antibody according to claim 66 wherein the fragment is selected from the group consisting of Fab', F(ab' )$_2$ and F(v).

* * * * *